(12) United States Patent
Wang et al.

(10) Patent No.: US 7,923,219 B2
(45) Date of Patent: Apr. 12, 2011

(54) UBIQUITIN E3 LIGASE

(75) Inventors: Hengbin Wang, Hoover, AL (US); Yi Zhang, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 318 days.

(21) Appl. No.: 11/915,610

(22) PCT Filed: Jun. 1, 2006

(86) PCT No.: PCT/US2006/021159
§ 371 (c)(1),
(2), (4) Date: May 22, 2008

(87) PCT Pub. No.: WO2006/130720
PCT Pub. Date: Dec. 7, 2006

(65) Prior Publication Data
US 2008/0248458 A1    Oct. 9, 2008

Related U.S. Application Data

(60) Provisional application No. 60/686,769, filed on Jun. 2, 2005, provisional application No. 60/750,564, filed on Dec. 15, 2005.

(51) Int. Cl.
*C12Q 1/37* (2006.01)
(52) U.S. Cl. .......................................... 435/23
(58) Field of Classification Search ............... 435/23, 435/4
See application file for complete search history.

(56) References Cited

U.S. PATENT DOCUMENTS

| | | | |
|---|---|---|---|
| 6,737,244 B2 | 5/2004 | Issakani et al. | |
| 6,740,495 B1 | 5/2004 | Issakani et al. | |
| 6,919,184 B2 * | 7/2005 | Issakani et al. | 435/7.92 |
| 2004/0137597 A1 | 7/2004 | Davydov et al. | |
| 2005/0009871 A1 | 1/2005 | Ramesh et al. | |
| 2005/0032139 A1 | 2/2005 | Issakani et al. | |

FOREIGN PATENT DOCUMENTS

| WO | WO 2004/052392 A2 | 6/2004 |
|---|---|---|
| WO | WO 2004/052392 A3 | 6/2004 |

OTHER PUBLICATIONS

Wang et al. Role of Histone H2A Ubiquitination in Polycomb Silencing. Nature vol. 413, Oct. 2004, 873-878.*
Capili A. et al. Structure of the C-Terminal RING Finger . . . J Molecular Biology 340(5)1117-1129, Jul. 23, 2004.*
Kenten J. et al. Assays for High Throughput Screening of E2 and E3 Ubiquitin Ligases. Methods in Enzymology 399:682-700, 2005.*
Wang H. et al. Role of Histone H2A Ubiquitination of Polycomb Silencing. Nature 431:873-878, Oct. 14, 2004.*
Francis et al.; "Reconstitution of a Functional Core Polycomb Repressive Complex," *Molecular Cell*, vol. 8 (Sep. 2001), p. 545-556.
J. Horn et al., "RING protein Trim32 associated with skin carcinogenesis has anti-apoptotic and E3-ubiquitin ligase properties," *Carcinogenesis*, vol. 25, No. 2 (2004), p. 157-167.
Joazeiro et al., "RING Finger Proteins: Mediators of Ubiquitin Ligase Activity," *Cell*, vol. 102 (Sep. 1, 2000), p. 549-552.
Kenten et al., "Assays for High-Throughput Screening of E2 and E3 Ubiquitin Ligases," *Methods in Enzymology*, vol. 399 (2005), p. 682-701.
Levine et al, "The Core of the Polycomb Repressive Complex Is Compositionally and Functionally Conserved in Files and Humans," *Molecular and Cellular Biology*, vol. 22, No. 17 (Sep. 2002), p. 6070-6078.
Napoles et al., "Polycomb Group Proteins Ring1A/B Link Ubiquitylation of Histone H2A to Heritable Gene Silencing and X Inactivation," *Developmental Cell*, vol. 7 (Nov. 2004), p. 663-675.
Otte et al., "Gene repression by Polycomb group protein complexes: a distinct complex for every occasion?" *Current Opinion in Genetics & Development*, vol. 13 (2003), p. 448-454.
Passmore et al., "Getting into position: the catalytic mechanisms of protein ubiquitylation," *Biochem. J.*, vol. 379, (2004), p. 513-525.
Ringrose et al., "Epigenetic Regulation of Cellular Memory by the Polycomb and Trithorax Group Proteins," *Annu. Rev. Genet.*, vol. 38 (2004), p. 413-43.
Satijn et al, "RING1 is Associatd with the Polycomb Group Protein Complex and Acts as a Transcriptional Repressor," *Molecular and Cellular Biology*, vol. 17, No. 7 (Jul. 1997), p. 4105-4113.
Schloβherr et al., "Gene inactivation in *Drosophila* mediated by the Polycomb gene product or by position-effect variegation does not involve major changes in the accessibility of the chromatin fibre," *Mol Ge Genet*, vol. 243 (1994), p. 453-462.
Schoorlemmer et al., "Ring1A is a transcriptional repressor that interacts with the Polycomb-M33 protein and is expressed at rhombomere boundaries in the mouse hindbrain," *The EMBO Journal*, vol. 15, No. 19 (1997), p. 5930-5942.
Shao et al., "Stabilization of Chromatin Structure by PRC1, a Polycomb Complex," *Cell*, vol. 98 (Jul. 9, 1999), p. 37-46.
Wang et al., "Hierarchical Recruitment of Polycomb Group Silencing Complexes," *Molecular Cell*, vol. 14 (Jun. 4, 2004), 637-646.
Wang et al., "Role of histone H2A ubiquitination in Polycomb silencing," *Nature*, vol. 431 (Oct. 14, 2004), p. 873-878.
Zhang, "No exception to reversibility," *Nature*, vol. 431 (Oct. 7, 2004), p. 637-639.
Zhang, "Role of histone modifications in polycomb silencing and cellular memory," Abstract presented at the Cold Spring Harbor 69th Symposium, (Jun. 2-7, 2004), 1 page.

(Continued)

*Primary Examiner* — Ralph Gitomer

(74) *Attorney, Agent, or Firm* — Myers Bigel Sibley & Sajovec, P.A.

(57) ABSTRACT

The present invention provides a native or reconstituted complex comprising Bmi1 and/or Ring1 and/or Ring2, wherein the complex has ubiquitin E3 ligase activity. Optionally, the complex further comprises HPH2 and/or HPC3. Also disclosed are methods of producing the reconstituted complex, methods of identifying compounds that modulate the ubiquitin E3 ligase activity of the native or reconstituted complex, and methods of identifying candidate compounds for treating cancer. Kits for determining modulation of protein ubiquitination and/or for ubiquitinating a target substrate are further provided.

19 Claims, 21 Drawing Sheets

OTHER PUBLICATIONS

Zhang, "Role of histone methylation and ubiquitination in PcG silencing," Oral presentation, Cold Spring Harbor 69th Symposium: Epigenetics (Jun. 6, 2004), 30 pages.

NCBI Accession No. NM_007552 *Mus musculus Bmi1 polycomb ring finger oncogene*, created Apr. 1, 2000.

NCBI Accession No. NM_005180 *Homo sapiens BMI1 polycomb finger oncogene*, created May 24, 1999.

NCBI Accession No. NP_005171 *Polycomb group ring finger 4* (*Homo sapiens*), created May 24, 1999.

NCBI Accession No. NP_031578 *Bmi1 polycomb ring finger oncogene*, created Apr. 11, 2000.

International Search Report and the Written Opinion of the International Searching Authority for PCT Application No. PCT/US06/21159, mailed Feb. 6, 2007.

Extended European Search Report for European Application No. 06784518.0, Mailed Jul. 30, 2008.

Cao, R et al., "Role of Bmi-1 and Ring1A in H2A Ubiquitylation and Hox Gene Silencing", Molecular Cell, Cell Press, Cambridge, MA, US, 20(6):845-854, Dec. 22, 2005. XP-002460133.

Hamer, Karien M. et al., "A Panel of Monoclonal Antibodies Against Human Polycomb Group Proteins", Hybridoma and Hybridomics, Mary Ann Liebert, New York, N.Y., US, 21(4): 245-252, Aug. 1, 2002. XP008015767.

Wei, Jianhua et al.,"Role of Bmi1 in H2A Ubiquitylation and Hox Gene Silencing", Journal of Biological Chemistry, 281(32): 22537-22544, Aug. 2006. XP002488667.

Zhang et al. "Mechanism of Polycomb Group Gene Silencing" *Cold Spring Harbor Symposia on Quantitative Biology* LXIX:1-9 (2004).

Zhang et al. "Mechanism of Polycomb Group Gene Silencing" *Cold Spring Harbor Symposia on Quantitative Biology* LXIX:1-9 (Oct. 25, 2004).

* cited by examiner

| | | | | | | |
|---|---|---|---|---|---|---|
| hRING2 51 | CPICLDMLKN | TMTTKECLHR | FCADCIITA | RSGHKECPIC | 90 | (SEQ ID NO:197) |
| hRING1 48 | CPICLDMLKN | TMTTKECLHR | FCSDCIVTA | RSGHKECPIC | 87 | (SEQ ID NO:198) |
| dRING 46 | CPICLDMLKK | TMTTKECLHR | FCSDCIVTA | RSGHKECPIC | 85 | (SEQ ID NO:199) |
| hBMI1 18 | CVLCGGYFID | ATIIECLHS | FCKTCIVRY | ET-SKYCPIC | 56 | (SEQ ID NO:200) |
| CONSENSUS | CPICLDMLKX | TMTTKECLHR | FCXDCIVTA | RSGHKECPIC | | (SEQ ID NO:201) |

FIG. 3A

H2A ²⁰AGLQFPVGR²⁸ (SEQ ID NO:5)
⁸¹HLQLAIRNDEELNK⁹⁴ (SEQ ID NO:35)

Ub ²⁹IQDKEGIPPDQQR⁴¹ (SEQ ID NO:36)
⁶³ESTLHLVLR⁷¹ (SEQ ID NO:6)

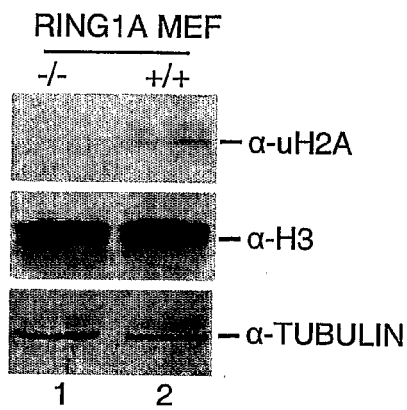 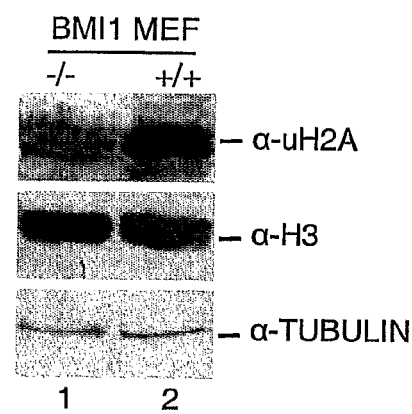
FIG. 8A  FIG. 8B
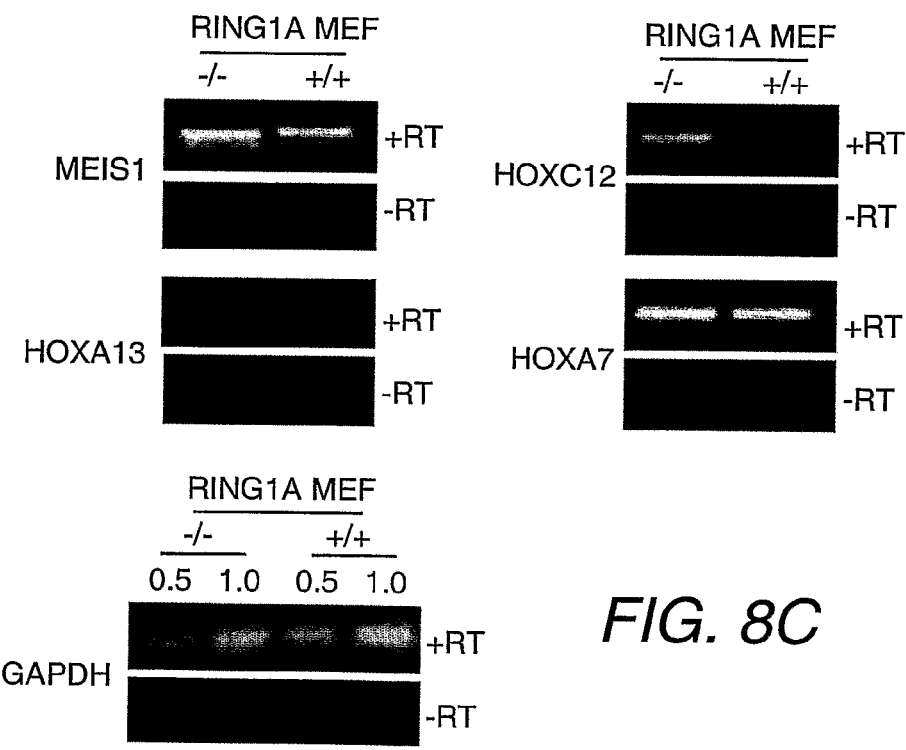
FIG. 8C

SEQUENCE LISTING

<160> NUMBER OF SEQ ID NOS: 203

<210> SEQ ID NO 1
<211> LENGTH: 7
<212> TYPE: PRT
<213> ORGANISM: Homo sapiens

<400> SEQUENCE: 1

Lys Thr Glu Ser His His Lys
1               5

<210> SEQ ID NO 2
<211> LENGTH: 4
<212> TYPE: PRT

-continued

```
<213> ORGANISM: Homo sapiens

<400> SEQUENCE: 2

Lys Arg Gly Gly
1

<210> SEQ ID NO 3
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 3
agaacaccat gactacaaat tcaagagatt tgtagtcatg gtgttct            47

<210> SEQ ID NO 4
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 4
ggctagagct tgataataat tcaagagatt attatcaagc tctagcc            47

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide

<400> SEQUENCE: 5

Asp Tyr Lys Asp Asp Asp Asp Lys
1               5

<210> SEQ ID NO 6
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 6
tgcagcggag cgagcccc                                            18

<210> SEQ ID NO 7
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 7
tcaacaggga tgagcgcgtc gtg                                      23

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
ggattccggt ctagggagtc                                          20
```

```
<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 9
cagccaatac agggtaggtg a                                              21

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
atgaactcct ttctggaata                                                20

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 11
cgtactctcc aactttcc                                                  18

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
agaactgtgg agctggccta                                                20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
ggtcgattgt ggtgagtgtg                                                20

<210> SEQ ID NO 14
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 14
atgccagtca gcagccata                                                 19

<210> SEQ ID NO 15
<211> LENGTH: 18
<212> TYPE: DNA
<213> ORGANISM: Artificial Sequence
<220> FEATURE:
<223> OTHER INFORMATION: Synthetic oligonucleotide
```

-continued

```
<400> SEQUENCE: 15
tgtacttcat gcggcggt                                                 18

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 16
tccagttata acggaggcga ac                                            22

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 17
gaatgggtgt ggaagcacca g                                             21

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 18
cgcaagctgc acattagtca c                                             21

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 19
gccatactca tgcttttcag c                                             21

<210> SEQ ID NO 20
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 20
ctgataaaga cctcagtg                                                 18

<210> SEQ ID NO 21
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 21
tcaggtagcg gttgaagtg                                                19

<210> SEQ ID NO 22
<211> LENGTH: 22
<212> TYPE: DNA
```

```
<213> ORGANISM: Artificial Sequence
<220> FEATURE:
<223> OTHER INFORMATION: Synthetic oligonucleotide

<400> SEQUENCE: 22
ctctgcagtg acctcgccaa ag                                          22

<210> SEQ ID NO 23
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 23
cttgtcagca gctgtggatt c                                           21

<210> SEQ ID NO 24
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 24
acggcaggta tatgcgct                                               18

<210> SEQ ID NO 25
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 25
gaaccagatc ttgacctgc                                              19

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
gtgagttctg gggcagaggc                                             20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
agttccaaag gcgaaaatgc                                             20

<210> SEQ ID NO 28
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 28
catatcccta ctcctccaac ctgc                                        24
```

<210> SEQ ID NO 29
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 29
cccaccgtgc tatagaaatt gg                                    22

<210> SEQ ID NO 30
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 30
ccgacaagta catggacac                                        19

<210> SEQ ID NO 31
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 31
tataggagct ggcgtctga                                        19

<210> SEQ ID NO 32
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 32 ccttttttaga gtacccactt tg                                   22

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
gcatctccag cggcttcctt                                       20

<210> SEQ ID NO 34
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 34
cggcgcctcc acccttcaga gacc                                  24

<210> SEQ ID NO 35
<211> LENGTH: 23
<212> TYPE: DNA
<213> ORGANISM: Artificial Sequence
<220> FEATURE:
<223> OTHER INFORMATION: Synthetic oligonucleotide

```
<400> SEQUENCE: 35
ctttcggtga ggtccagcaa ggc                                           23

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
ccgcacctac cagtaccact                                               20

<210> SEQ ID NO 37
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 37
ggagctgttt tcagcttgg                                                19

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
ttcacgtgag cacggtaaac                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
gttgggcaac ttgtggtctt                                               20

<210> SEQ ID NO 40
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 40
gctcttacgg ctacaattac aatg                                          24

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
gctgtagcca gactcatact                                               20

<210> SEQ ID NO 42
<211> LENGTH: 20
<212> TYPE: DNA
```

```
<213> ORGANISM: Artificial Sequence
<220> FEATURE:
<223> OTHER INFORMATION: Synthetic oligonucleotide

<400> SEQUENCE: 42
cgtcctccta ttacccacca                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
cacttctgct cctcggtctc                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
aaccgagttc cttcaacatg                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
cgagtcaggt agcgattgta                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
ttctacggct acgaccctct                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
cgtgcgatac ctcgatcctc                                              20

<210> SEQ ID NO 48
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 48
cgatcataag tcacgagagc g                                            21
```

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
tccttctcta gctccagcgt                                         20

<210> SEQ ID NO 50
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 50
cgatcataag tcacgagagc g                                       21

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
tccttctcta gctccagcgt                                         20

<210> SEQ ID NO 52
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 52
tggatgacca aactgcacat gagc                                    24

<210> SEQ ID NO 53
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 53
caagttgttg gcaatctcta tgcg                                    24

<210> SEQ ID NO 54
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 54
accttaggac ataacacaca ga                                      22

<210> SEQ ID NO 55
<211> LENGTH: 22
<212> TYPE: DNA
<213> ORGANISM: Artificial Sequence
<220> FEATURE:
<223> OTHER INFORMATION: Synthetic oligonucleotide -continued

```
<400> SEQUENCE: 55
acttcatgcg gcggttctgg aa                                              22

<210> SEQ ID NO 56
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 56
ccacgtccaa gacttcttcc accacggc                                        28

<210> SEQ ID NO 57
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 57
cacttcatcc ttcgattctg gaacc                                           25

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
acgtggactc gctcatctct                                                 20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 59
gccgtaaggg tgatagacca                                                 20

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
tgttggcagg cctctgtcct                                                 20

<210> SEQ ID NO 61
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 61
ctccaattcc agcgtctggt gt                                              22

<210> SEQ ID NO 62
<211> LENGTH: 20
<212> TYPE: DNA
```

```
<213> ORGANISM: Artificial Sequence
<220> FEATURE:
<223> OTHER INFORMATION: Synthetic oligonucleotide

<400> SEQUENCE: 62
cttcgacaac gcctactgcg                                               20

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 63
gtctgtcagg ttcagcatcc                                               20

<210> SEQ ID NO 64
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 64
tgcgctcggc ttcaagtacg                                               20

<210> SEQ ID NO 65
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 65
tggcgtgtga tgaactcgtt gac                                           23

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 66
tgtcgcacaa cgtgaacctg                                               20

<210> SEQ ID NO 67
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 67
cttcagctgc accttggtat ag                                            22

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 68
cacagcactt tcgagtggat                                               20
```

-continued

<210> SEQ ID NO 69
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 69
tgggtgtcat tcagctgtaa                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 70
cagatcttcc cctggatgaa                                              20

<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 71
tacttcatgc gacggttctg                                              20

<210> SEQ ID NO 72
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 72
cgatgaggga actcattgct                                              20

<210> SEQ ID NO 73
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 73
tgccctcctt actcaccatc                                              20

<210> SEQ ID NO 74
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 74
ggatacgata acttacagag ac                                           22

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 75
tagggtttgg aagcgactgt                                              20

<210> SEQ ID NO 76
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 76
cactacggga ttaagcctga aacc                                         24

<210> SEQ ID NO 77
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 77
tttgggtcaa gttgctgctg c                                            21

<210> SEQ ID NO 78
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 78
cctatggaat gcaaacctgt gg                                           22

<210> SEQ ID NO 79
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 79
atatccaggg acaggaacct cg                                           22

<210> SEQ ID NO 80
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 80
ctttgatcag ttctacgag                                               19

<210> SEQ ID NO 81
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 81
cagacggtcc ctgttcagt                                               19

<210> SEQ ID NO 82
<211> LENGTH: 20
<212> TYPE: DNA
```

```
<213> ORGANISM: Artificial Sequence
<220> FEATURE:
<223> OTHER INFORMATION: Synthetic oligonucleotide

<400> SEQUENCE: 82
accaggtcaa gttctatacg                                            20

<210> SEQ ID NO 83
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 83
caatctgctg ctttgtgtag                                            20

<210> SEQ ID NO 84
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 84
agaagtacat ggacgtgtcg                                            20

<210> SEQ ID NO 85
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 85
gttacttgtc tctccgaaag                                            20

<210> SEQ ID NO 86
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 86
ttattacagt aggtgaggag ttgaac                                     26

<210> SEQ ID NO 87
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 87
ttttcttcta gctccttccc catac                                      25

<210> SEQ ID NO 88
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 88
ccattaaaga agggagtttg cttgac                                     26
```

<210> SEQ ID NO 89
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 89
tgatgtggga acttgagttt ggtg                                    24

<210> SEQ ID NO 90
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 90
tatacattga tttggaagaa agttgc                                  26

<210> SEQ ID NO 91
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 91
caagttagac aagaggactg agg                                     23

<210> SEQ ID NO 92
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 92
acttggactt ccctctcaga cag                                     23

<210> SEQ ID NO 93
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 93
gcagtacaag tgtaggctat ctcc                                    24

<210> SEQ ID NO 94
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 94
ccagtcctag ttaggcaaca gagag                                   25

<210> SEQ ID NO 95
<211> LENGTH: 25
<212> TYPE: DNA
<213> ORGANISM: Artificial Sequence
<220> FEATURE:
<223> OTHER INFORMATION: Synthetic oligonucleotide

```
<400> SEQUENCE: 95
tgcttttgag acaggagacc catac                                      25

<210> SEQ ID NO 96
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 96
acaggatacc cctttctgac cc                                         22

<210> SEQ ID NO 97
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 97
aagtcacagc atttgtagca ggag                                       24

<210> SEQ ID NO 98
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 98
ccataccacc ctagctcaga aag                                        23

<210> SEQ ID NO 99
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 99
cggggaaacc cagcagagtc                                            20

<210> SEQ ID NO 100
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 100
ttccttcagt tcagttaaat gattcc                                     26

<210> SEQ ID NO 101
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 101
cgggcgatgg tcacactc                                              18

<210> SEQ ID NO 102
<211> LENGTH: 25
<212> TYPE: DNA
```

```
<213> ORGANISM: Artificial Sequence
<220> FEATURE:
<223> OTHER INFORMATION: Synthetic oligonucleotide

<400> SEQUENCE: 102
cctacatctt catctggtcc tttgc                                          25

<210> SEQ ID NO 103
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 103
ggctggctga gagggttgg                                                 19

<210> SEQ ID NO 104
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 104
ggccaagttc accggaccc                                                 19

<210> SEQ ID NO 105
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 105
gtgctgatgt tcacacagac tctc                                           24

<210> SEQ ID NO 106
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 106
agagagacac cgcagccc                                                  18

<210> SEQ ID NO 107
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 107
gattctgact gagcaaaagg aaagg                                          25

<210> SEQ ID NO 108
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 108 ggtatcccctt ttgtatgctg aaatgg                                        26
```

```
<210> SEQ ID NO 109
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 109
gcttaatttg gccgacgcaa ag                                              22

<210> SEQ ID NO 110
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 110
cgttgcccgt ccctttaaat ctcc                                            24

<210> SEQ ID NO 111
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 111
ccgccgctgc cgctctc                                                    17

<210> SEQ ID NO 112
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 112
tgcagcggag cgagcccc                                                   18

<210> SEQ ID NO 113
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 113
tcaacaggga tgagcgcgtc gtg                                             23

<210> SEQ ID NO 114
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 114
agtcaggtgt actgctccaa gg                                              22

<210> SEQ ID NO 115
<211> LENGTH: 25
<212> TYPE: DNA
<213> ORGANISM: Artificial Sequence
<220> FEATURE:
<223> OTHER INFORMATION: Synthetic oligonucleotide
```

<400> SEQUENCE: 115
aggttcttat acttccccaa atccc                                     25

<210> SEQ ID NO 116
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 116
caggagctgt caaccaccag atac                                      24

<210> SEQ ID NO 117
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 117
tcagatcaga gtggaaccca aagc                                      24

<210> SEQ ID NO 118
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 118
agcattgggt ctactcttcc tg                                        22

<210> SEQ ID NO 119
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 119
atggaatgcc tacatatgaa cagtc                                     25

<210> SEQ ID NO 120
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 120
cttcacttct ctagctcata agacag                                    26

<210> SEQ ID NO 121
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 121
acgccagcca gaatctactt c                                         21

<210> SEQ ID NO 122
<211> LENGTH: 22
<212> TYPE: DNA

```
<213> ORGANISM: Artificial Sequence
<220> FEATURE:
<223> OTHER INFORMATION: Synthetic oligonucleotide

<400> SEQUENCE: 122
ttctcagtgc ctgaagaagt cc                                          22

<210> SEQ ID NO 123
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 123
catctaattg tctcctggga tttctg                                      26

<210> SEQ ID NO 124
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 124
tttggagccc gtatattgac g                                           21

<210> SEQ ID NO 125
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 125
aaagattgac tccaccaagg tttc                                        24

<210> SEQ ID NO 126
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 126
tagagcagat acctaccttt taacc                                       25

<210> SEQ ID NO 127
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 127
taactggtct tcaatttgtt ttactc                                      26

<210> SEQ ID NO 128
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 128
gtggctggtt tgtttgtttg tttg                                        24
```

```
<210> SEQ ID NO 129
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 129
aggaattcac aataggatgg cactc                                    25

<210> SEQ ID NO 130
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 130
attaaataag tggtggctga aattgc                                   26

<210> SEQ ID NO 131
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 131
ttagcacaac agggttccta cac                                      23

<210> SEQ ID NO 132
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 132
ccagcaagca ggaggaggac                                          20

<210> SEQ ID NO 133
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 133
cgccggtagc tgctcacttc                                          20

<210> SEQ ID NO 134
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 134
ctgaaggagc tagagaagga gtacg                                    25

<210> SEQ ID NO 135
<211> LENGTH: 24
<212> TYPE: DNA
<213> ORGANISM: Artificial Sequence
<220> FEATURE:
<223> OTHER INFORMATION: Synthetic oligonucleotide
```

```
<400> SEQUENCE: 135
tttggtagga atgactgggc tctc                                          24

<210> SEQ ID NO 136
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 136
caaattactc agttcttgcc tgttcc                                        26

<210> SEQ ID NO 137
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 137
acacttagca ttgtggctgg ag                                            22

<210> SEQ ID NO 138
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 138
tcaaggtgag gttgggaact agg                                           23

<210> SEQ ID NO 139
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 139
caagcaataa aatcaaggcc aaacc                                         25

<210> SEQ ID NO 140
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 140
tgactcttca gggcaggata ctatg                                         25

<210> SEQ ID NO 141
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 141
tgcctctgtc aaatggtgct agg                                           23

<210> SEQ ID NO 142
<211> LENGTH: 25
<212> TYPE: DNA
```

<213> ORGANISM: Artificial Sequence
<220> FEATURE:
<223> OTHER INFORMATION: Synthetic oligonucleotide

<400> SEQUENCE: 142
gctgtactca tttctttgtc ccatc        25

<210> SEQ ID NO 143
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 143
aattcttcag gttctttgtc tctcag        26

<210> SEQ ID NO 144
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 144
gcctcattct acactcaact ctgg        24

<210> SEQ ID NO 145
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 145
gcttgggatg gttcctttct catag        25

<210> SEQ ID NO 146
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 146
agtcttgtgc aagctcctga gg        22

<210> SEQ ID NO 147
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 147
gctctggtgc ccttgtgttt g        21

<210> SEQ ID NO 148
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 148
ctccttggaa acagaagttc tagttc        26

```
<210> SEQ ID NO 149
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 149
aggcgggttc tgagtggg                                                    18

<210> SEQ ID NO 150
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 150
tccaagagca gacgtgtatc tatcg                                            25

<210> SEQ ID NO 151
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 151
cgcagcaagg cttcccagg                                                   19

<210> SEQ ID NO 152
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 152
agagagtttc tagggctga taacc                                             25

<210> SEQ ID NO 153
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 153
tctcctcgcc tagtgaatta ctgag                                            25

<210> SEQ ID NO 154
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 154
gggaaaatgt cagagttggc agtc                                             24

<210> SEQ ID NO 155
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 155
tgatggctgg ggaaggaggg                                              20

<210> SEQ ID NO 156
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 156
acagtaatgc ttgtgtcctt acagg                                        25

<210> SEQ ID NO 157
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 157
aaactctccc cgcacattca tc                                           22

<210> SEQ ID NO 158
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 158
cgctgttgac ccacgatgat g                                            21

<210> SEQ ID NO 159
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 159
gcacaaaccc ctcttccttc tg                                           22

<210> SEQ ID NO 160
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 160
tgccaagtct gaaacctaga gatg                                         24

<210> SEQ ID NO 161
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 161
gactcattga ttgcacatga acatc                                        25

<210> SEQ ID NO 162
<211> LENGTH: 26
<212> TYPE: DNA
```

```
<213> ORGANISM: Artificial Sequence
<220> FEATURE:
<223> OTHER INFORMATION: Synthetic oligonucleotide

<400> SEQUENCE: 162
atgaaattca gcgatggtat gacatg                                        26

<210> SEQ ID NO 163
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 163
ctacaaaacg cagacagaat cacag                                         25

<210> SEQ ID NO 164
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 164
tcacctacgt tcgttcatat tctctc                                        26

<210> SEQ ID NO 165
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 165
acagcaaagg agattaccct acaac                                         25

<210> SEQ ID NO 166
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 166
agtttctgct ggggctgac                                                19

<210> SEQ ID NO 167
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 167
aaaccgttgg aatttacaat atctcc                                        26

<210> SEQ ID NO 168
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 168
ctaattaaag agggacgggc tgtg                                          24
```

<210> SEQ ID NO 169
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 169
gaaggtgtct cctgtgtgga tattc                                    25

<210> SEQ ID NO 170
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 170
ggctgccttc gctgtcctac                                          20

<210> SEQ ID NO 171
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 171
gtccttaccg ctggctgaga g                                        21

<210> SEQ ID NO 172
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 172
cgtcttgcta gtttaggcag gg                                       22

<210> SEQ ID NO 173
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 173
attactacta ctactactcc cacccc                                   26

<210> SEQ ID NO 174
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 174
ctactatgga aggtagtgtt gaggc                                    25

<210> SEQ ID NO 175
<211> LENGTH: 21
<212> TYPE: DNA
<213> ORGANISM: Artificial Sequence
<220> FEATURE:
<223> OTHER INFORMATION: Synthetic oligonucleotide

```
<400> SEQUENCE: 175
accaaggcaa gcttagtctg g                                              21

<210> SEQ ID NO 176
<211> LENGTH: 9
<212> TYPE: PRT
<213> ORGANISM: Homo sapiens

<400> SEQUENCE: 176

Ala Gly Leu Gln Phe Pro Val Gly Arg
1               5

<210> SEQ ID NO 177
<211> LENGTH: 9
<212> TYPE: PRT
<213> ORGANISM: Homo sapiens

<400> SEQUENCE: 177

Glu Ser Thr Leu His Leu Val Leu Arg
1               5

<210> SEQ ID NO 178
<211> LENGTH: 11
<212> TYPE: PRT
<213> ORGANISM: Homo sapiens

<400> SEQUENCE: 178

Thr Trp Glu Leu Ser Leu Tyr Glu Leu His Arg
1               5                   10

<210> SEQ ID NO 179
<211> LENGTH: 17
<212> TYPE: PRT
<213> ORGANISM: Homo sapiens

<400> SEQUENCE: 179

Thr Pro Gln Glu Ala Ile Met Asp Gly Thr Glu Ile Ala Val Ser Pro
1               5                   10                  15

Arg

<210> SEQ ID NO 180
<211> LENGTH: 14
<212> TYPE: PRT
<213> ORGANISM: Homo sapiens

<400> SEQUENCE: 180

Ser Leu Arg Pro Asp Pro Asn Phe Asp Ala Leu Ile Ser Lys
1               5                   10

<210> SEQ ID NO 181
<211> LENGTH: 14
<212> TYPE: PRT
<213> ORGANISM: Homo sapiens

<400> SEQUENCE: 181

Ile Tyr Pro Ser Arg Glu Glu Tyr Glu Ala His Gln Asp Arg
1               5                   10

<210> SEQ ID NO 182
<211> LENGTH: 16
<212> TYPE: PRT
<213> ORGANISM: Homo sapiens

<400> SEQUENCE: 182
```

```
Leu His Asn Gln Gln Ala Leu Ser Ser Ser Ile Glu Glu Gly Leu Arg
1               5                   10                  15

<210> SEQ ID NO 183
<211> LENGTH: 8
<212> TYPE: PRT
<213> ORGANISM: Homo sapiens

<400> SEQUENCE: 183

Thr Arg Pro Leu Leu Asn Ile Arg
1               5

<210> SEQ ID NO 184
<211> LENGTH: 11
<212> TYPE: PRT
<213> ORGANISM: Homo sapiens

<400> SEQUENCE: 184

Tyr Arg Val Arg Pro Thr Cys Lys Arg Met Lys
1               5                   10

<210> SEQ ID NO 185
<211> LENGTH: 14
<212> TYPE: PRT
<213> ORGANISM: Homo sapiens

<400> SEQUENCE: 185

Val Arg Pro Thr Cys Lys Arg Met Lys Ile Ser His Gln Arg
1               5                   10

<210> SEQ ID NO 186
<211> LENGTH: 10
<212> TYPE: PRT
<213> ORGANISM: Homo sapiens

<400> SEQUENCE: 186

Ser Ser Leu Leu Val Gly Asn Leu Lys Lys
1               5                   10

<210> SEQ ID NO 187
<211> LENGTH: 9
<212> TYPE: PRT
<213> ORGANISM: Homo sapiens

<400> SEQUENCE: 187

Tyr Ala Gln Gly Phe Leu Pro Glu Lys
1               5

<210> SEQ ID NO 188
<211> LENGTH: 9
<212> TYPE: PRT
<213> ORGANISM: Homo sapiens

<400> SEQUENCE: 188

Arg Val Gly Leu Phe His Ser Asp Arg
1               5

<210> SEQ ID NO 189
<211> LENGTH: 10
<212> TYPE: PRT
<213> ORGANISM: Homo sapiens

<400> SEQUENCE: 189

Asp Leu Glu Leu Pro Asp Met His Met Arg
1               5                   10
```

<210> SEQ ID NO 190
<211> LENGTH: 11
<212> TYPE: PRT
<213> ORGANISM: Homo sapiens

<400> SEQUENCE: 190

Glu Asp His Leu Met Ser Ala Met Asn Ile Lys
1               5                   10

<210> SEQ ID NO 191
<211> LENGTH: 11
<212> TYPE: PRT
<213> ORGANISM: Homo sapiens

<400> SEQUENCE: 191

Thr Trp Glu Leu Ser Leu Tyr Glu Leu Gln Arg
1               5                   10

<210> SEQ ID NO 192
<211> LENGTH: 17
<212> TYPE: PRT
<213> ORGANISM: Homo sapiens

<400> SEQUENCE: 192

Thr Pro Gln Glu Ala Ile Thr Asp Gly Leu Glu Ile Val Val Ser Pro
1               5                   10                  15

Arg

<210> SEQ ID NO 193
<211> LENGTH: 14
<212> TYPE: PRT
<213> ORGANISM: Homo sapiens

<400> SEQUENCE: 193

Ile Tyr Pro Ser Arg Asp Glu Tyr Glu Ala His Gln Glu Arg
1               5                   10

<210> SEQ ID NO 194
<211> LENGTH: 16
<212> TYPE: PRT
<213> ORGANISM: Homo sapiens

<400> SEQUENCE: 194

His Asn Asn Gln Gln Ala Leu Ser His Ser Ile Glu Glu Gly Leu Lys
1               5                   10                  15

<210> SEQ ID NO 195
<211> LENGTH: 12
<212> TYPE: PRT
<213> ORGANISM: Homo sapiens

<400> SEQUENCE: 195

Thr Ser Gly Asn Ala Thr Val Asp His Leu Ser Lys
1               5                   10

<210> SEQ ID NO 196
<211> LENGTH: 13
<212> TYPE: PRT
<213> ORGANISM: Homo sapiens

<400> SEQUENCE: 196

Val Asn Lys Pro Met Glu Leu Tyr Tyr Ala Pro Thr Lys
1               5                   10

```
<210> SEQ ID NO 197
<211> LENGTH: 39
<212> TYPE: PRT
<213> ORGANISM: Homo sapiens

<400> SEQUENCE: 197

Cys Pro Ile Cys Leu Asp Met Leu Lys Asn Thr Met Thr Thr Lys Glu
1               5                   10                  15

Cys Leu His Arg Phe Cys Ala Asp Cys Ile Ile Thr Ala Arg Ser Gly
            20                  25                  30

His Lys Glu Cys Pro Thr Cys
        35

<210> SEQ ID NO 198
<211> LENGTH: 39
<212> TYPE: PRT
<213> ORGANISM: Homo sapiens

<400> SEQUENCE: 198

Cys Pro Ile Cys Leu Asp Met Leu Lys Asn Thr Met Thr Thr Lys Glu
1               5                   10                  15

Cys Leu His Arg Phe Cys Ser Asp Cys Ile Val Thr Ala Arg Ser Gly
            20                  25                  30

His Lys Glu Cys Pro Thr Cys
        35

<210> SEQ ID NO 199
<211> LENGTH: 39
<212> TYPE: PRT
<213> ORGANISM: Drosophila melanogaster

<400> SEQUENCE: 199

Cys Pro Ile Cys Leu Asp Met Leu Lys Lys Thr Met Thr Thr Lys Glu
1               5                   10                  15

Cys Leu His Arg Phe Cys Ser Asp Cys Ile Val Thr Ala Arg Ser Gly
20                  25                  30

His Lys Glu Cys Pro Thr Cys
35

<210> SEQ ID NO 200
<211> LENGTH: 38
<212> TYPE: PRT
<213> ORGANISM: Homo sapiens

<400> SEQUENCE: 200

Cys Val Leu Cys Gly Gly Tyr Phe Ile Asp Ala Thr Thr Ile Ile Glu
1               5                   10                  15

Cys Leu His Ser Phe Cys Lys Thr Cys Ile Val Arg Tyr Glu Thr Ser
            20                  25                  30

Lys Tyr Cys Pro Ile Cys
        35

<210> SEQ ID NO 201
<211> LENGTH: 39
<212> TYPE: PRT
<213> ORGANISM: Artificial Sequence
<220> FEATURE:
<223> OTHER INFORMATION: Synthetic Ring domain consensus sequence
<220> FEATURE:
<221> NAME/KEY: MISC_FEATURE
<222> LOCATION: (10)..(10)
<223> OTHER INFORMATION: Xaa denotes a polar amino acid residue
<220> FEATURE:
<221> NAME/KEY: MISC_FEATURE
```

```
<222> LOCATION: (23)..(23)
<223> OTHER INFORMATION: Xaa denotes any amino acid residue

<400> SEQUENCE: 201

Cys Pro Ile Cys Leu Asp Met Leu Lys Xaa Thr Met Thr Thr Lys Glu
1               5                   10                  15

Cys Leu His Arg Phe Cys Xaa Asp Cys Ile Val Thr Ala Arg Ser Gly
            20                  25                  30

His Lys Glu Cys Pro Thr Cys
        35

<210> SEQ ID NO 202
<211> LENGTH: 21
<212> TYPE: PRT
<213> ORGANISM: Homo sapiens

<400> SEQUENCE: 202

Asn Ile Gln Ala Val Leu Leu Pro Lys Lys Thr Glu Ser His His His
1               5                   10                  15

Lys Ala Gln Ser Lys
            20

<210> SEQ ID NO 203
<211> LENGTH: 15
<212> TYPE: PRT
<213> ORGANISM: Drosophila melanogaster

<400> SEQUENCE: 203

Asn Ile Gln Ala Val Leu Leu Pro Lys Lys Thr Glu Lys Lys Ala
1               5                   10                  15
```

UBIQUITIN E3 LIGASE

RELATED APPLICATION INFORMATION

This application is a 35 U.S.C. §371 national phase application of PCT International Application No. PCT/US2006/021159, having an international filing date of Jun. 1, 2006 and claims the benefit of U.S. provisional application Ser. No. 60/686,769, filed Jun 2, 2005 and U.S. provisional application Ser. No. 60/750,564, filed Dec. 15, 2005, the disclosures of which are incorporated herein by reference in their entireties.

GOVERNMENT INTEREST

This invention was made, in part, with government support under grant number GM68804 from the National Institutes of Health. The U.S. Government has certain rights in the invention.

FIELD OF THE INVENTION

The present invention concerns a ubiquitin E3 ligase and methods of identifying modulators thereof.

BACKGROUND OF THE INVENTION

Covalent modification of histones play important roles in regulating chromatin dynamics and transcription (Jenuwein et al., (2001) *Science* 293:1074-80; Zhang et al., (2001) *Genes Dev* 15:2343-60). One example of histone modification is ubiquitination, which mainly occurs on histones H2A and H2B (Zhang, (2003) *Genes Dev* 17:2733-40). Although recent studies have uncovered the enzymes involved in histone H2B ubiquitination (Robzyk et al., (2000) *Science* 287: 501-4; Hwang et al., (2003) *Mol Cell* 11: 261-6; Wood et al., (2003) *Mol Cell* 11:267-74) and a "cross-talk" between H2B ubiquitination and histone methylation (Sun et al., (2002) *Nature* 418:104-8; Dover et al., (2002) *J. Biol. Chem.* 277: 28368-71), the responsible enzymes and the functions of H2A ubiquitination are unknown.

Ligation of ubiquitin involves a series of enzymatic reactions. First, ubiquitin itself is activated with ATP by the ubiquitin-activating enzyme (E1), then transferred to a ubiquitin carrier protein (E2), and finally it is transferred to ubiquitin ligase (E3). E3 enzyme catalyzes the covalent modification of lysine residues of the target protein with activated ubiquitin (Chau et al. (1989) Science 243:1576-1583). Recently, an additional conjugation factor, named E4, has been shown to be important in the ubiquitination process in conjunction with E1, E2, and E3 (Koegl et al. (1999) Cell 96(5):635-44).

The E1 and E2 ubiquitin ligases are structurally related and well characterized enzymes. There are several species of E2, some of which act in preferred pairs with specific E3 enzymes. E3 enzymes contain two separate activities: a ubiquitin ligase activity to conjugate ubiquitin to substrates, and a targeting activity to physically bring the ligase and substrate together. Substrate specificity of different E3 enzymes is the major determinant that confers specificity for different target proteins.

The inventors now report the purification and functional characterization of a ubiquitin E3 ligase complex.

SUMMARY OF THE INVENTION

The present invention is based, in part, on the isolation and reconstitution of a complex that has histone H2A ubiquitin E3 ligase activity ("H2A E3 ligase" activity). The inventors have demonstrated that histone H2A ubiquitination is involved in homeotic box (i.e., Hox) gene silencing and is implicated in chromatin changes that are linked to cancer, X-inactivation, germline development and/or stem cell pluripotency. Thus, the invention also provides reagents and methods for identifying compounds for the modulation of ubiquitin E3 ligase activity, Hox gene silencing, X-inactivation, genomic imprinting, stem cell pluripotency and/or germline development and/or for identifying compounds that are candidates for the treatment of cancer.

Thus, as a first aspect, the invention provides a method of identifying a compound that modulates ubiquitin E3 ligase activity of Bmi1 or Ring2, the method comprising:

contacting Bmi1 or Ring2 with a protein substrate in the presence of a test compound; and detecting the level of ubiquitination of the protein substrate under conditions sufficient to provide ubiquitination of the protein substrate, wherein a change in ubiquitination of the protein substrate as compared with the level of ubiquitination of the protein substrate in the absence of the test compound indicates that the test compound is a modulator of the ubiquitin E3 ligase activity of Bmi1 or Ring2.

The invention also provides a method of identifying a compound that modulates ubiquitin E3 ligase activity of a complex comprising (a) Bmi1 and/or (b) Ring2, the method comprising:

contacting the complex with a protein substrate in the presence of a test compound; and detecting the level of ubiquitination of the protein substrate under conditions sufficient to provide ubiquitination of the protein substrate, wherein a change in ubiquitination of the protein substrate as compared with the level of ubiquitination of the protein substrate in the absence of the test compound indicates that the test compound is a modulator of the ubiquitin E3 ligase activity of the complex.

The invention further provides a method of identifying a candidate compound for treating cancer, the method comprising:

contacting BMi1 or Ring2 with a histone H2A substrate in the presence of a test compound; and detecting the level of ubiquitination of the histone H2A substrate under conditions sufficient to provide histone H2A ubiquitination, wherein a reduction in histone H2A ubiquitination as compared with the level of histone H2A ubiquitination in the absence of the test compound indicates that the test compound is a candidate compound for the treatment of cancer.

Still further, the invention provides a method of identifying a candidate compound for treating cancer, the method comprising:

contacting a complex comprising (a) Ring2 and/or (b) Bmi1 with a histone H2A substrate in the presence of a test compound; and detecting the level of histone H2A ubiquitination under conditions sufficient to provide histone H2A ubiquitination, wherein a reduction in histone H2A ubiquitination as compared with the level of histone H2A ubiquitination in the absence of the test compound indicates that the test compound is a candidate compound for the treatment of cancer.

As another aspect, the invention provides a reconstituted mammalian complex comprising Bmi1 and/or Ring2, wherein the reconstituted complex has ubiquitin E3 ligase activity.

As yet another aspect, the invention provides a reconstituted mammalian complex comprising: (a) Bmi1 and Ring2 and/or Ring1; or (b) Bmi1 and Ring1, wherein the reconstituted complex has ubiquitin E3 ligase activity.

As still another aspect, the invention provides an isolated mammalian complex comprising Bmi1 and/or Ring2, wherein the complex does not comprise HPH1, HPH3 or SCMH1; and further wherein the isolated complex has ubiquitin E3 ligase activity.

The invention further provides an isolated mammalian complex comprising: (a) Bmi1 and Ring2 and/or Ring1; or (b) Bmi1 and Ring1, wherein the complex does not comprise HPH1, HPH3 and/or SCMH1; and further wherein the isolated complex has ubiquitin E3 ligase activity.

Also provided are methods and host cells for making the reconstituted complexes of the invention.

As a further aspect, the invention provides a method of modulating protein ubiquitination of a protein substrate, comprising contacting a cell with a compound that modulates ubiquitin E3 ligase activity identified according to the methods described herein.

As another aspect, the invention provides a kit for determining modulation of protein ubiquitination, the kit comprising:
 (a) Bmi1, Ring2 or a reconstituted complex of the invention or nucleic acid encoding any of the foregoing; and
 (b) written instructions for methods for determining modulation of the ubiquitin E3 ligase activity, and optionally additional reagents or apparatus for carrying out methods for determining modulation of ubiquitin E3 ligase activity.

As still a further aspect, the invention provides a kit for ubiquitinating a target protein substrate, the kit comprising:
 (a) Bmi1, Ring2 or a reconstituted complex of the invention or nucleic acid encoding any of the foregoing; and
 (b) written instructions for methods for ubiquitinating a target protein substrate, and optionally additional reagents or apparatus for carrying out methods for ubiquitinating a target protein substrate.

As yet another aspect, the invention provides a method of ubiquitinating a target protein substrate, the method comprising contacting a protein substrate with Bmi1 or Ring2 or a complex comprising Bmi1 and/or Ring2 under conditions that permit the ubiquitination of the protein substrate by the complex.

These and other aspects of the invention are set forth in more detail in the detailed description below.

BRIEF DESCRIPTION OF THE DRAWINGS

FIG. 1A, Ubiquitin ligase assay using HeLa nuclear proteins fractionated on DE52 and P11 columns. Numbers on top of the panels indicate the salt concentration (M) for step elution. NE and NP represent nuclear extracts and nuclear pellet, respectively. Molecular weight markers are indicated at the left of the panel. Left and right panels use histone octamer and oligonucleosome substrates, respectively. FIG. 1B, The ligase activity depends on the presence of ATP, E1, E2, ubiquitin, nucleosomal histones (NUC.), and proteins present in the 0.5 M P11 nuclear pellet fraction. Molecular weight markers are indicated at the left of the panel. FIG. 1C, Mass spectrometry analysis of the ubiquitinated protein revealed the presence of histone H2A and ubiquitin. A peptide that contains amino acids from both ubiquitin and H2A identifies lysine 119 as the ubiquitination site.

FIG. 2A, Schematic representation of the steps used to purify the H2A ubiquitination ligase complex. Numbers represent the salt concentrations (mM) at which the E3 ligase activity elutes from the columns. FIG. 2B, The H2A ubiquitin ligase activity assay (top panel) and western blot analysis (bottom two panels) of the protein fractions derived from the gel-filtration S300 column. The elution profile of the protein markers is indicated on top of the panel. Antibodies used for the western blot are indicated. FIG. 2C, Silver stained SDS-polyacrylamide gel (top panel), H2A ubiquitin ligase activity assay (second panel) and western blot analysis (bottom two panels) of the fractions derived from the MONOQ™ column. The candidate proteins that co-fractionated with the E3 ligase activity are indicated by *. The positions of the protein size markers on SDS-polyacrylamide gel electrophoresis (PAGE) are indicated to the left of the panel. FIG. 2D, Silver stained SDS-polyacrylamide gels containing samples derived from input (In), flow-through (Ft), and Bound (B) proteins immunoaffinity purified with rabbit IgG and Ring1 antibodies. The identities of the proteins co-immunoprecipitating with Ring1 are indicated. Peptides derived from each protein band are also indicated. Numbers represent the amino acid number of the respective proteins. NS indicates nonspecific-binding proteins that are also present in the control IP (lane 3). FIG. 2E, The same samples presented in FIG. 2D were analyzed by H2A ubiquitin ligase activity assay (top panel) and western blot analysis (bottom two panels). Antibodies used are indicated.

FIGS. 3A-3E show that Ring2 is the catalytic subunit and is required for H2A ubiquitination in vivo. FIG. 3A, Diagram of the human Ring1, Ring2, their *Drosophila* homolog dRing, and human Bim1. A sequence alignment of the ring finger domain of these proteins is shown. Amino acids that are completely conserved are boxed. The two Ring2 mutants used in FIG. 3B are indicated by *. Numbers represent the amino acid number. FIG. 3B, Ubiquitin ligase activity (bottom panel) of recombinant proteins (top panel, lanes 2-6, 8 and 9) and native hPRC1L (lane 7). FIG. 3C, Estimation of the Ring2 knock-down level in the KD1 and KD2 cell lines relative to the mock knock-down cells transfected with empty vector. Tubulin was used as a loading control. Antibodies used are indicated on the left of the panel. FIG. 3D, Sequence alignment between ubiquitinated human H2A (hH2A) and *Drosophila* H2A (dH2A). Amino acids that are completely conserved are boxed. Ubiquitinated Lys119 is indicated. FIG. 3E, Ring2 knock-down results in morphological change and cell growth inhibition. Top panels show morphological changes of control and knock-down HeLa cells. Bottom panel shows the growth curve of control and knock-down HeLa cells. Viable cells were counted by trypan blue staining at different times after initial seeding of $3 \times 10^4$ cells.

FIG. 4A, Schematic representation of the Ubx promoter and bxd $PRE_D$ regions. The regions amplified by PCR in the ChIP assays are depicted as horizontal lines. FIG. 4B, Western blot analysis (left panel) of histone extracts from SL2 cells using a well-characterized monoclonal antibody (E6C5) against uH2A (Vassilev, et al. (1995) *J. Cell Sci.* 108(Pt 3):1205-15). Right Panel, COOMASSIE® stained SDS-PAGE of a parallel gel containing the same sample as in the left panel and mass spectrometric analysis of the indicated band. The identified peptides confirm that the protein is ubiquitinated H2A . FIG. 4C, ChIP results showing the wild-type distributions of dRing and ubiquitinated H2A in wing imaginal discs. FIG. 4D, ChIP results showing the distribution of dRing, and ubiquitinated H2A at the $PRE_D$ region in normal SL2 cells. FIG. 4E, Western blot showing dRing levels in SL2 RNAi cells. FIG. 4F, ChIPs of SL2 cells transfected with GFP double-stranded RNA (left panels) or dRing double-stranded RNA (right panels). Antibodies used in immunoprecipitations and the PCR amplified regions are indicated to the left and above, respectively (FIG. 4C, FIG. 4D, and FIG. 4F). Rp, RpII140 promoter; mock, crude rabbit preimmune-antiserum; Gen, genomic DNA. FIG. 4G, dRing knock-down leads to derepression of Ubx. Levels of Ubx transcripts in cells transfected with GFP or dRing double-stranded RNA was evaluated by RT-PCR. FIG. 4E and FIG. 4G, SL2 cells transfected twice with GFP or dRing double-stranded RNA. RpII140 expression serves as a control. RT+, reverse transcriptase included in the reaction; RT−, reverse transcriptase omitted.

FIG. 5A, GST pull-down assays using equal amounts of GST-fusion proteins and in vitro translated $S^{35}$-labeled proteins indicated on right. "In" represents 10% of the total Input. FIG. 5B, Schematic representation of the interactions detected in FIG. 5A.

FIG. 6A, Schematic representation of the steps involved in PRC1 reconstitution. FIG. 6B, Silver staining of a polyacrylamide-SDS gel (top panel), and ubiquitin ligase activity assay (bottom panel) of the fractions derived from the S6 gel-filtration column. The positions of the protein size markers are indicated to the left of the panel. The four components of the recombinant PRC1 complex are indicated by FIGS. 7A-7B show characterization of individual components in the PRC1 complex.

FIGS. 8A-8C show that Bmi1 and Ring1A are both important for H2A ubiquitination in vivo and knock-out of individual components results in derepression of several Hox genes. FIG. 8A, Western blot analysis of ubiquitinated H2A extracted from wild-type and Ring1A knock-out MEF cells with an antibody specific for ubiquitinated H2A. Equal loading was confirmed by western blot using anti-H3 and anti-tubulin antibodies. FIG. 8B, Western blot analysis of ubiquitinated H2A extracted from wild-type and Bmi1 knock-out MEF cells with antibody specific for ubiquitinated H2A. Equal loading was confirmed by western blot using anti-H3 and anti-tubulin antibodies. FIG. 8C, RT-PCR analysis of Hox genes expression in Ring1A knock-out and wild-type MEF cells. GAPDH was used as a control. For each gene, "−RT" serves as control to exclude the genomic DNA amplification. HoxA7 shows no change, while C12, A13 and Meis1 show increased expression in Ring1A −/− cells.

FIG. 10A, Silver stained gels reveal the purity of the different Ring1B-containing subcomplexes. FIG. 10B, Bmi1 stimulates the ubiquitin E3 ligase activity of Ring1B in vitro. The amounts of Ring1B in different lanes are quantified by western blotting using an anti-Ring 1B antibody (top panel). Although lanes 1 and 2 contain similar amounts of Ring1B, lane 2 has higher enzymatic activity. Lanes 4 and 6 have similar amounts of Ring1B, but lane 6 exhibited much higher E3 ligase activity.

FIG. 12A, ChIP analysis across the HoxC13 gene using an antibody against Bmi-1 in wild-type (top two panels) and Bmi-1 null (bottom two panels) MEFs. The diagram on top of the panel represents the entire HoxC13 gene where the two exons are indicated by two boxes. FIG. 12B, ChIP analysis of the HoxC13 promoter (region A) and a down-stream region (region B) of the HoxC13 gene as indicated in the diagram. Each region covers about 500 bps. Antibodies against Ring1B, Ring1A, Bmi-1, SUZ12, ubiquitylated H2A, trimethyl-H3-K27, and an IgG control were used in the ChIP assays using wild-type (top panels) and Bmi-1 null (bottom panels) MEF cells. ChIP results were revealed by ethidium bromide staining of agarose gels containing PCR amplified ChIP DNA.

FIG. 13A, Ring1A and Ring1B have similar elution profiles on a SUPEROSE-6 column with protein extracts prepared from wild-type or Bmi-1 null MEFs. The elution profile of the protein markers is indicated at the top of the panel. FIG. 13B, Silver staining of an SDS-gel containing the reconstituted Mel-18 containing complex. Mel-18 co-purifies with the other components as a stable protein complex. FIG. 13C, Comparison of the E3 ligase activity of the four-component complexes reconstituted with Ring1A, Ring1B, Pc3 plus Bmi-1 or Mel-18. Western blot (top panel) serves to quantify the complex amounts. FIG. 13D, Comparison of the E3 ligase activity of Ring1B/Bmi1-1, Ring1B/Mel-18 with Ring1B alone. Western blot (top panel) serves to quantify the protein amounts.

FIG. 14A, Semi-quantitative RT-PCR analysis of HOXC13 expression in mock and SUZ12 knock-down cells. GAPDH was used as a control for equal RNA amounts. A quantification of the results is shown on the right panel. FIG. 14B, ChIP analysis of promoter (region A) and a downstream region (region B) analogous to the regions analyzed in FIG. 12. ChIP was performed with mock knockdown (top panels) and SUZ12 knock-down cells (bottom panels) using antibodies indicated.

DETAILED DESCRIPTION OF THE INVENTION

Figures 1A, 1B:
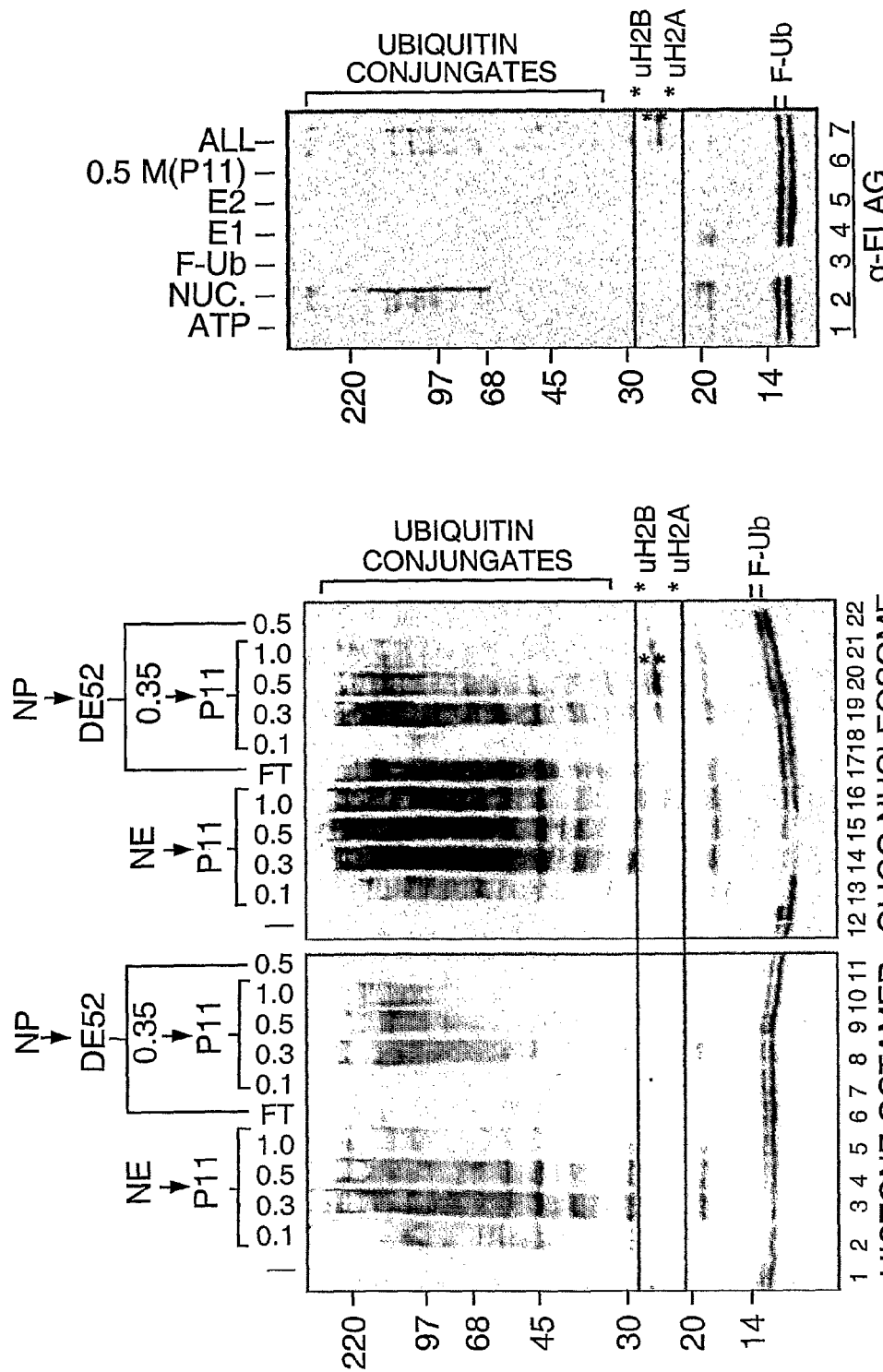
FIGS. 1A-1C show the identification of an H2A ubiquitin ligase activity in HeLa cells.

The present invention will now be described in more detail with reference to the accompanying drawings, in which embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning" A Laboratory Manual 2nd Ed. (Cold Spring Harbor, N.Y., 1989); F. M. Ausubel et al. Current Protocols in Molecular Biology (Green Publishing Associates, Inc. and John Wiley & Sons, Inc., New York).

Chromatin structure plays a role in gene regulation and epigenetic inheritance. Post-translational modifications of histones are involved in the establishment and maintenance of higher-order chromatin structure. Further, it has been reported that the tails of certain core histones can be modified by acetylation, methylation, phosphorylation, ribosylation and ubiquitination. The present invention is based, in part, on the isolation and reconstitution of a protein complex that exhibits histone H2A ubiquitin E3 ligase ("H2A E3 ligase") activity.

I. Isolation and Reconstitution of a Ubiquitin E3 Ligase

The inventors have isolated and reconstituted a complex having histone H2A ubiquitin E3 ligase (hereinafter "H2A E3 ligase") activity that includes the Ring1, Ring2 and Bmi1 proteins. Ring2 and Bmi1 have both been demonstrated to possess catalytic activity as H2A E3 ligases.

Accordingly, as one aspect, the present invention provides an isolated native complex having ubiquitin E3 ligase activity (e.g., histone or H2A E3 ligase activity). Generally, the complex comprises the catalytic subunit(s) Bmi1 and/or Ring2. In particular embodiments, the isolated native complex comprises, consists essentially of, or consists of Ring1, Ring2 and Bmi1, and optionally HPH2 and/or HPC3, wherein the isolated complex has ubiquitin E3 ligase activity. In other embodiments, the isolated native complex comprises, consists essentially of, or consists of Ring1, Ring2 and optionally, Bmi1 or HPC3. The complex can further optionally comprise, consist essentially of, or consist of HPH2. In other embodiments, the isolated native complex comprises, consists essentially of, or consists of Bmi1 and Ring2 and, optionally Ring1 or HPC3. The complex can further optionally comprise, consist essentially of, or consist of HPH2. In still further embodiments, the isolated native complex comprises, consists essentially of, or consists of Bmi1 and Ring1, and optionally Ring2 or HPC3. The complex can further optionally comprise, consist essentially of or consist of HPH2. Alternatively, the complex can comprise, consist essentially of, or consist of Ring1, Ring2, Bmi1 and HPC3. The complex can further optionally comprise, consist essentially of or consist of HPH2.

By "consisting essentially of" it is meant that the complex does not include any other components that materially affect the ubiquitin E3 ligase activity (e.g., the histone or histone H2A E3 ligase activity) of the complex.

An "isolated" protein or complex as used herein means a protein/complex that is separated or substantially free from at least some of the other components of the cell or organism, for example, the cellular structural components or other proteins or nucleic acids commonly found associated with the protein/complex. In particular embodiments, the "isolated" protein or complex is at least about 0.5%, 1%, 5%, 10%, 25%, 50%, 60%, 70%, 75%, 80%, 85%, 90%, 95%, 97%, 98%, 99% or more pure (w/w). In other embodiments, an "isolated" protein or complex indicates that at least about a 5-fold, 10-fold, 25-fold, 100-fold, 1000-fold, 10,000-fold, 100,000-fold, 1,000,000-fold or more enrichment of the protein/complex (w/w) is achieved as compared with the starting material.

The native complex can be isolated from any suitable source, including cells, tissue, or whole organisms, and the native or reconstituted complex is generally from Drosophila or a higher organism, including fish (e.g., zebrafish), avians and mammals such as mice, rats, dogs, cats, goats, sheep, cattle, horses, pigs, rabbits, monkeys and other non-human primates, and humans.

According to other embodiments, the present invention provides a reconstituted complex having ubiquitin E3 ligase activity. Generally, the complex comprises the catalytic subunit(s) Bmi1 and/or Ring2. In particular embodiments, the reconstituted complex comprises, consists essentially of, or consists of Bmi1 and/or Ring1 and/or Ring2, wherein the reconstituted complex has ubiquitin E3 ligase activity. In other embodiments, the reconstituted complex comprises, consists essentially of, or consists of Ring1, Ring2 and optionally, Bmi1 or HPC3. The complex can further optionally comprise, consist essentially of, or consist of HPH2. In further embodiments, the reconstituted complex comprises, consists essentially of, or consists of Ring1, Ring2 and Bmi1, and optionally HPC3 and/or HPH2. In other embodiments, the reconstituted complex comprises, consists essentially of, or consists of Bmi1 and Ring2 and, optionally, Ring1 or HPC3. The complex can further optionally comprise, consist essentially of or consist of HPH2. In still further embodiments, the reconstituted complex can comprise, consist essentially of, or consist of Bmi1 and Ring1, and, optionally Ring2 or HPC3. The complex can further optionally comprise, consist essentially of or consist of HPH2. Alternatively, the complex can comprise, consist essentially of, or consist of Ring1, Ring2, Bmi1, and HPC3. The complex can further optionally comprise, consist essentially of or consist of HPH2.

As used herein, "reconstituted" refers to a complex that is formulated from recombinant proteins. As used herein, "recombinant" refers to a product formed using recombinant nucleic acid technology, i.e., created utilizing genetic engineering techniques.

In embodiments of the invention, the reconstituted complex of the present invention has enzyme activity comparable to the enzyme activity of a native complex (e.g., at least about 70%, 80%, 90%, 95% or more of the activity of the native complex).

The function of ubiquitin E3 ligases are well-known in the art. In particular embodiments, the complex of the invention has histone ubiquitin E3 ligase activity, optionally histone H2A E3 ligase activity. By "H2A E3 ligase" is meant an E3 ligase that transfers ubiquitin to H2A to produce a covalently modified ubiquitinated H2A. In representative embodiments, the native or reconstituted H2A E3 ligase ubiquitinates H2A at lysine 119 (H2A-K119). Optionally, the native or reconstituted complex has histone ubiquitin E3 ligase activity that is substantially specific for H2A or H2A-K119, meaning that substantially all of the observed histone ubiquitin E3 ligase activity is directed to H2A or H2A-K119, respectively (e.g., at least about 75%, 80%, 85%, 90%, 95%, 98% or more). In some embodiments of the invention, there is no, or essentially no, detectable ubiquitination on histone substrates other than H2A or H2A-K119. In still other embodiments, insignificant levels of ubiquitination (e.g., less than about 5% or 10%) is detected at other histone sites, e.g., histone H2B.

The native or reconstituted complexes of the invention are distinguishable from the complexes described by Levine et al., (2002) *Mol. Cell. Biology* 22:6070-6078 (dPRC1 and hPRC-H) and Francis et al., *Mol. Cell.* 8:545-556 (functional core of dPRC1), which complexes are specifically disclaimed herein. Thus, the native or reconstituted complex is not a complex as described in these publications.

In some embodiments of the invention, the native or reconstituted complex consists essentially of, or consists of mammalian proteins, optionally human proteins. In other embodiments, the native or reconstituted complex consists essentially of or consists of insect proteins. In still other embodiments, the native and/or reconstituted complex does not comprise *Drosophila* proteins.

In other embodiments, the native or reconstituted complex does not comprise Pc, HPH1, HPH3, HPC2, M33, SNF2H, SCMH1 (Scm), Mel18, Mph 1/2, HSP70, an HSC protein (e.g., HSC70), Zeste, a TAF protein (e.g., dTAFII), YY1 and/or β-tubulin or their homologs from other species. In representative embodiments, the complex does not comprise HPH2 or homologs thereof from other species (e.g., ph). In representative embodiments, the complex does not comprise HPC3 or homologs thereof from other species (e.g., Pc). In other representative embodiments, the complex does not comprise HPH1, HPH3 and/or SCMH1 or homologs thereof from other species.

As used herein, the term "homolog" has its ordinary meaning in the art, e.g., a gene or protein from another species that is similar in structure and evolutionary origin.

The terms "Ring1," "Ring2," "Bmi1," "HPH2" and "HPC3" as used herein encompass homologs from any organism and are not intended to be limited to human or mammalian proteins. In particular embodiments, Ring1, Ring2, Bmi1, HPC3 and/or HPH2 can be mammalian (e.g., human, simian or other non-human primate, rat, mouse, feline, canine, bovine, equine, ovine, caprine, lagomorph, etc.) proteins, avian proteins, fish proteins (e.g., zebrafish) or *Drosophila* proteins (e.g., dRing1 is a homolog for mammalian Ring1 and Ring2; Psc is a homolog of Bmi1; ph is a homolog of HPH2; Pc is a homolog of HPC3) or any combination thereof. A "combination thereof" with respect to the proteins described above indicates that at least one protein can be derived from one organism and at least one protein can be derived from a different organism. For example, Ring1 can be a mammalian protein and Bmi1 can be a *Drosophila* protein (i.e., Psc).

Thus, in some aspects of the invention, the native or reconstituted complex comprises dRing1 and/or Psc. In particular embodiments, the complex comprises, consists essentially of, or consists of dRing1 and Psc, Pc and/or ph. Alternatively, the complex can comprise, consist essentially of, or consist of Psc and ph; Psc and Pc; or Psc, ph and Pc.

In particular embodiments, the Bmi1 protein is methylated at the amino acid residue(s) corresponding to K88 and/or K92 of the mouse or human Bmi1 protein. Methylated protein can be made by any method known in the art, for example, by expression in insect (e.g., Sf9) or mammalian cells.

Further, as understood by those skilled in the art, the terms "Ring1" and "Ring2" are used interchangeably herein with the terms "Ring1A" and "Ring1B," respectively.

It will further be understood by those of skill in the art that the terms "Ring1," "Ring2," "Bmi1," "HPC3" and "HPH2" (including non-mammalian homologs thereof) can encompass a functional or biologically active variant, isoform, derivative, fragment or the like as understood by those skilled in the art. As used herein, "variant" refers to an amino acid sequence that is altered by one or more amino acids. The variant may have "conservative" changes, wherein a substituted amino acid has similar structural or chemical properties. In particular, such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; Gln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function.

Alternatively, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE™ software.

As used herein, "derivative" refers a component that has been subjected to a chemical modification. Derivatization of a protein component can involve the replacement of a hydrogen by an acetyl, acyl, alkyl, amino, formyl, or morpholino group. Derivative molecules can retain the biological activities of the naturally occurring molecules but can confer advantages such as longer lifespan or enhanced activity.

In particular embodiments, a biologically active variant, isoform or derivative of any of the protein components of the reconstituted complex has at least about 60%, 70%, 75%, 80%, 85%, 90%, 95% 98% or more amino acid sequence similarity or identity with the amino acid sequence of a naturally-occurring protein.

Further, in particular embodiments, a "functional" variant, isoform or derivative retains at least one biological activity normally associated with the component of interest (e.g., H2A E3 ligase or, more specifically H2A-K119 E3 ligase, activity). In particular embodiments, the "functional" variant, isoform or derivative retains at least about 40%, 50%, 60%, 75%, 85%, 90%, 95% or more biological activity normally associated with the naturally occurring component (e.g., H2A E3 ligase or, more specifically H2A-K119 E3 ligase, activity) or can even have a greater level of biological activity.

As used herein, the term "fragment" refers to a portion of the component that retains at least one biological activity normally associated with that component (e.g., H2A E3 ligase or, more specifically H2A-K119 E3 ligase, activity) and can have at least about 50%, 70%, 80%, 90% or more of the biological activity as compared with the full-length protein or even has a greater level of biological activity. For example, in particular embodiments, a fragment of Ring1, Ring2 or Bmi1 comprises the RING (catalytic) domain. In representative embodiments, the fragment retains the ability to participate in complex formation. In other representative embodiments, the fragment comprises at least about 50, 100, 150, 200, 250 or 500 consecutive amino acids of the full-length protein.

In other embodiments, a Bmi1 fragment or variant comprises the lysine residues corresponding to K88 and/or K92 of the mouse or human protein.

Isoforms or variants of the components of the complex are known in the art, see, e.g., GenBank Accession Nos. NM_198040 and NP_932157 (HPH2, human variant 1); GenBank Accession Nos. NM_004427 and NP_004418 (HPH2, human variant 2); GenBank Accession Nos. NM_080055 and NP_524794 (ph-d [distal], *Drosophila melanogaster*); and GenBank Accession Nos. NM_057523 and NP_476871 (ph-p [proximal], *Drosophila melanogaster*).

In some embodiments of the invention, two or more components of the complex can be provided as fusion proteins comprising all or a functional portion of the two or more components, for example, a Ring1/Ring2 fusion, a Ring2/Bmi1 fusion, and the like.

The complexes of the invention can have ubiquitin E3 ligase activity toward any suitable protein substrate. In some embodiments of the invention, the complex has histone ubiquitin E3 ligase, optionally H2A E3 ligase activity (e.g., H2A-K119 E3 ligase activity), and the substrate is a histone or histone H2A, respectively.

In some embodiments, the native or reconstituted complex has a substrate preference for histones (e.g., H2A) in nucleosome form as compared with free histone substrates. In some embodiments, the complex has a preference for mononucleosome, dinucleosome and/or oligonucleosome substrates. Thus, the histone substrate can be a core histone or histone complex (i.e., free or essentially free of DNA such as a histone octamer) and/or a nucleosome substrate (e.g., a mononucleosome, a dinucleosome or an oligonucleosome).

The histone (e.g., H2A) substrate can be from any suitable source, generally from yeast, Drosophila or higher organisms, including fish (e.g., zebrafish), avians and mammals such as mice, rats, dogs, cats, goats, sheep, cattle, horses, pigs, rabbits, monkeys and other non-human primates, and humans.

The present invention further provides methods of producing the inventive reconstituted complexes, the methods comprising, consisting essentially of, or consisting of providing one or more host cells comprising heterologous nucleic acid sequences encoding the proteins of the reconstituted complex and culturing the host cell under conditions sufficient for expression of the proteins and production of the reconstituted complex.

"Consisting essentially of" as used herein with respect to the methods of the invention indicates that the method includes no additional material steps beyond those specified.

In particular embodiments, the method comprises, consists essentially of, or consists of: providing one or more host cells comprising (a) a heterologous nucleic acid sequence encoding a Ring2 protein; and/or (b) a heterologous nucleic acid sequence encoding a Bmi1 protein; and culturing the one or more host cells under conditions sufficient for expression of the proteins and production of the reconstituted complex. In some embodiments, the one or more host cells further comprise (c) a heterologous nucleic acid sequence encoding a Ring1 protein and/or (d) a heterologous nucleic acid sequence encoding a HPH2 protein and/or (e) a heterologous nucleic acid sequence encoding a HPC3 protein.

The method can comprise, consist essentially of, or consist of: providing one or more host cells comprising (a) a heterologous nucleic acid sequence encoding a Ring2 protein and (b) a heterologous nucleic acid sequence encoding a Bmi1 protein; and/or (c) a heterologous nucleic acid sequence encoding a Ring1 protein; and culturing the one or more host cells under conditions sufficient for expression of the proteins and production of the reconstituted complex. In some embodiments, the one or more host cells further comprise (d) a heterologous nucleic acid sequence encoding a HPH2 protein and/or (e) a heterologous nucleic acid sequence encoding a HPC3 protein.

Alternatively, the method can comprise, consist essentially of, or consist of: providing one or more host cells comprising (a) a heterologous nucleic acid sequence encoding a Bmi1 protein; and a (b) a heterologous nucleic acid sequence encoding a Ring1 protein and/(c) a heterologous nucleic acid sequence encoding a Ring2 protein; and culturing the one or more host cells under conditions sufficient for expression of the proteins and production of the reconstituted complex. In some embodiments, the one or more host cells further comprise (d) a heterologous nucleic acid sequence encoding a HPH2 protein and/or (e) a heterologous nucleic acid sequence encoding a HPC3 protein.

The different protein components of the complex can be expressed in one cell. Alternatively, the components can be expressed in two or more cells (e.g., each component expressed in a different cell).

As used herein, "nucleic acid" encompasses both RNA and DNA, including cDNA, genomic DNA, synthetic (e.g., chemically synthesized) DNA and chimeras of RNA and DNA. The nucleic acid may be double-stranded or single-stranded. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

The term "heterologous nucleic acid" is a well-known term of art and would be readily understood by one of skill in the art to be a nucleic acid that is not normally present within the host cell into which it has been introduced and/or is a nucleic acid that is expressed under the control of regulatory elements that are not normally present within the host cell. A heterologous nucleic acid of this invention can also be a nucleic acid that is present in an amount, or expressed in an amount, that is not normally the amount present in the cell into which the nucleic acid has been introduced. Additionally, the heterologous nucleic acids encoding the components of the reconstituted complex can be associated with appropriate expression control sequences, e.g., transcription/translation control signals and polyadenylation signals.

It will be appreciated that a variety of promoter/enhancer elements can be used depending on the level and tissue-specific expression desired. The promoter can be constitutive or inducible (e.g., the metallothionein promoter or a hormone inducible promoter), depending on the pattern of expression desired. The promoter can be native or foreign and can be a natural or a synthetic sequence. By foreign, it is intended that the promoter is not found in the wild-type host into which the promoter is introduced. The promoter is chosen so that it will function in the target cell(s) of interest. Moreover, specific initiation signals are generally provided for efficient translation of inserted protein coding sequences. These translational control sequences, which can include the ATG initiation codon and adjacent sequences, can be of a variety of origins, both natural and synthetic. In embodiments of the invention wherein the heterologous nucleic acids encoding the components of the reconstituted complex comprise an additional sequence to be transcribed, the transcriptional units can be operatively associated with separate promoters or with a single upstream promoter and one or more downstream internal ribosome entry site (IRES) sequences (e.g., the picornavirus EMC IRES sequence).

Suitable host cells are well-known in the art. See e.g., Goeddel, *Gene Expression Technology*: Methods in Enzymology 185, Academic Press, San Diego, Calif. (1990). For example, the host cell can be a prokaryotic or eukaryotic cell. Further, it is well-known that proteins can be expressed in bacterial cells such as *E. coli*, insect cells (e.g., the baculovirus expression system), yeast cells, plant cells or mammalian cells (e.g. human, rat, mouse, bovine, porcine, ovine, caprine, equine, feline, canine, lagomorph, simian and the like). The host cell can be a cultured cell such as a cell of a primary or immortalized cell line. The host cell can be a cell in a microorganism, animal or plant being used essentially as a bioreactor. In particular embodiments of the present invention, the host cell is any insect cell that allows for replication of expression vectors. For example, the host cell can be from *Spodoptera frugiperda*, such as the Sf9 or Sf21 cell lines, drosophila cell lines, or mosquito cell lines, e.g., *Aedes albopictus* derived cell lines. Use of insect cells for expression of heterologous proteins is well documented, as are methods of introducing nucleic acids, such as vectors, e.g., insect-cell compatible vectors (such as baculovirus vectors), into such cells and methods of maintaining such cells in culture. See, for example, Methods in Molecular Biology, ed. Richard, Humana Press, NJ (1995); O'Reilly et al., Baculovirus Expression Vectors, A Laboratory Manual, Oxford Univ. Press (1994); Samulski et al., J. Vir. 63:3822-8 (1989); Kajigaya et al., Proc. Nat'l. Acad. Sci. USA 88: 4646-50 (1991); Ruffing et al., J. Vir. 66:6922-30 (1992); Kimbauer et al., Vir. 219:37-44 (1996); Zhao et al., Vir. 272:382-93 (2000); and Samulski et al., U.S. Pat. No. 6,204,059. In particular embodiments of the present invention, the insect cell is an Sf9 cell.

In some embodiments, the method of producing the reconstituted complex further comprises isolating the expressed reconstituted complex from the cultured host cell or a culture medium from the cultured host cell (i.e., conditioned medium). As known in the art, the reconstituted complex can be isolated according to well-known protein isolation and purification techniques that can involve a combination of procedures and iterations of the same in an effort to obtain the desired amount of protein and level of purity.

Accordingly, in some embodiments, the method of producing the reconstituted complex comprises binding the expressed reconstituted complex to a solid support. The solid support can be an inorganic and/or organic particulate support material comprising sand, silicas, silicates, silica gel, glass, glass beads, glass fibers, alumina, zirconia, titania, nickel, and suitable polymer materials including, but not limited to, agarose, polystyrene, polyethylene, polyethylene glycol, polyethylene glycol grafted or covalently bonded to polystyrene (also termed PEG-polystyrene), in any suitable form known to those of skill in the art such as a particle, bead, gel, filter or plate. The solid support can comprise a moiety, as known to those skilled in the art, that can be used to bind to the expressed reconstituted complex, e.g., nickel, a peptide antigen, avidin, an antibody or an enzyme substrate (e.g. glutathione) directed to the expressed reconstituted complex. The moiety can recognize the enzyme complex itself or, alternatively, a purification tag associated with the complex. Detection can be facilitated by coupling or tagging (i.e., physically linking) the desired protein or antibody directed to the protein to an appropriate detectable substance, including commercially available detectable substances. Examples of detectable substances include, but are not limited to, various antibodies, enzymes, peptide and/or protein tags, prosthetic groups, fluorescent materials, luminescent materials, bioluminescent materials, and radioactive materials. Antibodies directed against the components of the complex are known in the art, e.g., antibodies directed against Ring1 (Schoorlemmer et al., (1997) *EMBO J.* 16:5930-5942), Bmi1 (available from Upstate). Examples of suitable enzymes include, but are not limited to, glutathione S-transferase (GST), horseradish peroxidase, alkaline phosphatase, β-galactosidase, or acetyl cholinesterase. Examples of peptide and/or protein tags include, but are not limited to, a polyhistidine peptide tag, the FLAG peptide tag, maltose binding protein (MBP), thioredoxin (Trx) and calmodulin binding peptide. Examples of suitable prosthetic group complexes include, but are not limited to, streptavidin/biotin and avidin/biotin. Examples of suitable fluorescent materials include, but are not limited to, umbelliferone, fluorescein, fluorescein isothiocyanate, rhodamine, dichlorotriazinylamine fluorescein, dansyl chloride or phycoerythrin. An example of a luminescent material includes luminal. Examples of bioluminescent materials include, but are not limited to, luciferase, luciferin, and aequorin. Examples of suitable radioactive material include, but are not limited to, $^{125}I$, $^{131}I$, $^{35}I$ and $^{3}H$. In particular embodiments, the expressed reconstituted complex comprises a purification tag (e.g., any one or more of the components can be tagged). In some embodiments, the reconstituted complex produced by the methods of the invention has a purity level of at least about 40%, 50%, 60%, 70%, 80%, 90%, 95%, 97%, 98%, 99% or more (w/w).

In further embodiments of the present invention, the one or more host cells can be stably transformed with the heterologous nucleic acid sequences encoding the proteins described above. "Stable transformation" as used herein generally refers to the integration of the heterologous nucleic acid sequences into the genome of the host cell in contrast to "transient transformation" wherein the heterologous nucleic acid sequences introduced into the host cell do not integrate into the genome of the host cell. The term "stable transformant" can further refer to stable expression of an episome (e.g. Epstein-Barr Virus (EBV)).

In particular embodiments, the one or more host cells is stably transformed with a heterologous nucleic acid sequence encoding one or more of the components of the complex (as described above).

In some embodiments, the one or more host cells comprise one or more delivery vectors comprising the heterologous nucleic acid sequences encoding the proteins in the complex. As used herein, "delivery vector" refers to a viral or non-viral vector that comprises one or more heterologous nucleic acid sequences (i.e., transgenes), e.g., two, three, four, five or more heterologous nucleic acid sequences. In particular embodiments, the heterologous nucleic acids are delivered by separate vectors, and the one or more vectors comprise, consist essentially of, or consist of: (i) a vector comprising a heterologous nucleic acid sequence encoding a Ring2 protein; and/or (ii) a separate vector comprising a heterologous nucleic acid sequence encoding a Bmi1 protein. In particular embodiments, the one or more host cells additionally comprise, consist essentially of, or consist of (iii) a separate vector comprising a heterologous nucleic acid sequence encoding a Ring1 protein and/or (iv) a further separate vector comprising a heterologous nucleic acid sequence encoding a HPH2 protein and/or (v) a further separate vector comprising a heterologous nucleic acid sequence encoding an HPC3 protein.

The one or more vectors can comprise, consist essentially of, or consist of: (i) a vector comprising a heterologous nucleic acid sequence encoding a Ring2 protein; and (ii) a separate vector comprising a heterologous nucleic acid sequence encoding a Bmi1 protein; and/or (iii) a separate vector comprising a heterologous nucleic acid sequence encoding a Ring1 protein. Alternatively, the one or more vectors can comprise, consist essentially of, or consist of: (i) a vector comprising a heterologous nucleic acid sequence encoding a Bmi1 protein; and (ii) a separate vector comprising a heterologous nucleic acid sequence encoding a Ring1 protein and/or (iii) a separate vector comprising a heterologous nucleic acid sequence encoding a Ring2 protein. In particular embodiments, the one or more host cells additionally comprise, consist essentially of, or consist of a further separate vector comprising a heterologous nucleic acid sequence encoding a HPH2 protein and/or a further separate vector comprising a heterologous nucleic acid sequence encoding an HPC3 protein.

In representative embodiments, methods of producing the reconstituted complex further comprise transforming the host cell with the one or more vectors. The components of the reconstituted complex can each be expressed from a separate vector. Alternatively, a single vector can encode one or more of the components of the reconstituted complex.

Suitable vectors include virus vectors (e.g., baculovirus, retrovirus, alphavirus, vaccinia virus, adenovirus, adeno-associated virus, or herpes simplex virus), lipid vectors, polylysine vectors, synthetic polyamino polymer vectors that are used with nucleic acid molecules, such as plasmids, and the like. Delivery vectors are described in more detail in Section IV.

In further embodiments, the present invention provides a host cell comprising heterologous nucleic acid sequences encoding one or more of the proteins of the reconstituted complex. In particular embodiments, the heterologous nucleic acid sequences comprise, consist essentially of, or consist of (a) a heterologous nucleic acid sequence encoding a Ring2 protein and/or (b) a heterologous nucleic acid sequence encoding a Bmi1 protein and/or (c) a heterologous nucleic acid sequence encoding a Ring1 protein and, optionally, (d) a heterologous nucleic acid sequence encoding a HPH2 protein and/or (e) a heterologous nucleic acid sequence encoding a HPC3 protein.

The heterologous nucleic acid sequences can comprise, consist essentially of, or consist of (a) a heterologous nucleic acid sequence encoding a Ring2 protein and (b) a heterologous nucleic acid sequence encoding a Bmi1 protein and/or (c) a heterologous nucleic acid sequence encoding a Ring1 protein Alternatively, the heterologous nucleic acid sequences can comprise, consist essentially of, or consist of (a) a heterologous nucleic acid sequence encoding a Bmi1 protein and (b) a heterologous nucleic acid sequence encoding a Ring1 protein and/or (d) a heterologous nucleic acid sequence encoding a Ring2 protein. Optionally, the host cell can further comprises, consist essentially of, or consist of a heterologous nucleic acid sequence encoding a HPH2 protein and/or a heterologous nucleic acid sequence encoding a HPC3 protein.

Suitable host cells are described above. In some embodiments, the host cell is an insect cell or a mammalian cell. In particular embodiments, the insect cell is an Sf9 cell.

Further, the host cell can be stably transformed with the heterologous nucleic acid sequences encoding the proteins of the reconstituted complex. In some embodiments, the host cell comprises one or more delivery vectors comprising the heterologous nucleic acid sequences as described above. In further embodiments, the one or more vectors comprise, consist essentially of, or consist of (i) a vector comprising a heterologous nucleic acid sequence encoding a Ring2 protein, and (ii) a separate vector comprising a heterologous nucleic acid sequence encoding a Bmi1 protein, and optionally, (iii) a further separate vector comprising a heterologous nucleic acid sequence encoding a Ring1 protein and/or (iv) a further separate heterologous nucleic acid sequence encoding a HPH2 protein and/or (v) a further separate heterologous nucleic acid sequence encoding a HPC3 protein.

The one or more vectors can comprise, consist essentially of, or consist of (i) a vector comprising a heterologous nucleic acid sequence encoding a Ring2 protein, and (ii) a separate vector comprising a heterologous nucleic acid sequence encoding a Bmi1 protein, and/or (iii) a further separate vector comprising a heterologous nucleic acid sequence encoding a Ring1 protein and optionally, (iv) a further separate heterologous nucleic acid sequence encoding a HPH2 protein and/or (v) a further separate heterologous nucleic acid sequence encoding a HPC3 protein.

Alternatively, the one or more vectors can comprise, consist essentially of, or consist of (i) a vector comprising a heterologous nucleic acid sequence encoding a Bmi1 protein, and (ii) a separate vector comprising a heterologous nucleic acid sequence encoding a Ring1 protein, and/or (iii) a separate vector comprising a heterologous nucleic acid sequence encoding a Ring2 protein, and optionally, (iv) a further separate heterologous nucleic acid sequence encoding a HPH2 protein and/or (v) a further separate heterologous nucleic acid sequence encoding a HPC3 protein.

Suitable vectors are described herein. According to embodiments of the present invention, the vector is a baculovirus vector.

Nucleic acid and amino acid sequences of Ring1, Ring2, Bmi1, HPH2 and HPC3 are known in the art, see e.g., GenBank Accession Nos. NM_002931 and NP_002922 (Ring1, human); GenBank Accession Nos. NM_009066 and NP_033092 (Ring1A, mouse); GenBank Accession Nos. NM_007212 and NP_009143 (Ring2, human); GenBank Accession Nos. NM_011277 and NP_035407 (Ring1B, mouse); GenBank Accession Nos. NM_058161 and NP_477509 (dRing1, Drosophila melanogaster); GenBank Accession Nos. NM_005180 and NP_005171 (Bmi1, human); GenBank Accession Nos. NM_007552 and NP_031578 (Bmi1, mouse); GenBank Accession Nos. NM_079001 and NP_523725 (Psc, Drosophila melanogaster); GenBank Accession Nos. NM_198040 and NP_932157 (HPH2, human variant 1); GenBank Accession Nos. NM_004427 and NP_004418 (HPH2, human variant 2); GenBank Accession Nos. NM_080055 and NP_524794 (ph-d [distal], Drosophila melanogaster); GenBank Accession Nos. NM_057523 and NP_476871 (ph-p [proximal], *Drosophila melanogaster*); GenBank Accession Nos. AF174482 and AAG09180 (HPC3, human); GenBank Accession Nos. NM_013926 and NP_038954 (polycomb protein [Pc3], mouse); GenBank Accession Nos. NM_205616 and NP_991179 (chromobox homolog 8 [cbx8], *Danio rerio*); GenBank Accession Nos. XM_582905 and XP_582905 (polycomb protein [Pc3], *Bos taurus*); GenBank Accession Nos. XM_845656 and XP_850749 (polycomb protein [Pc3], *Canis familiaris*); and GenBank Accession Nos. NM_001034078 and NP_001029250 (chromobox homolog 8[cbx8], *Rattus norvegicus*).

II. Screening Methods

The present invention further provides methods of identifying compounds that modulate the ubiquitin E3 ligase activity (e.g., histone or H2A E3 ligase activity) of Bmi1, Ring2 or a native or reconstituted complex as described herein or modulate binding Bmi1, Ring2 or the native or reconstituted complex to a protein substrate, such as a histone or H2A (e.g., as free histone or in nucleosome form). As used herein, "modulate," "modulates" or "modulation" refers to enhancement (e.g., an increase) or inhibition (e.g., a reduction) in the specified activity. The term "enhancement," "enhance," "enhances" or "enhancing" or grammatical variations thereof refers to an increase in the specified parameter (e.g., at least about a 1.1-fold, 1.25-fold, 1.5-fold, 2-fold, 3-fold, 4-fold, 5-fold, 6-fold, 8-fold, 10-fold, twelve-fold, fold, fifteen-fold, fifty-fold, one hundred-fold or more increase). The term "inhibit" or "reduce" or grammatical variations thereof as used herein refers to a decrease or diminishment in the specified activity of at least about 10%, 25%, 35%, 40%, 50%, 60%, 75%, 80%, 90%, 95% or more. In particular embodiments, the inhibition or reduction results in no or essentially no (i.e., an insignificant amount, e.g., less than about 10% or even 5%) detectable activity.

In particular embodiments, the invention is practiced to identify a compound that modulates the histone ubiquitin E3 ligase activity, the H2A E3 ligase activity, or more specifically, the H2A-K119 ubiquitin E3 ligase activity of the native or reconstituted complex described herein.

The complex can be a reconstituted or native complex as described herein, with the exception that the native or reconstituted complex can also be a complex as described by Levine et al., (2002) *Mol. Cell. Biology* 22:6070-6078 (dPRC1 and hPRC-H) and/or Francis et al., *Mol. Cell.* 8:545-556 (functional core of dPRC1).

Any suitable assay for determining modulation of ubiquitin E3 ligase activity can be used to identify compounds that modulate the ubiquitin E3 ligase activity (e.g., histone or H2A E3 ligase activity). In particular embodiments, the invention provides a method of identifying a compound that modulates the ubiquitin E3 ligase activity of the native or reconstituted complex, the method comprising, consisting essentially of, or consisting of contacting the complex with a protein substrate (e.g., a histone H2A substrate) in the presence of a test compound, and detecting the level of ubiquitination of the protein substrate under conditions sufficient to provide ubiquitination of the protein substrate, wherein a change in ubiquitination of the protein substrate as compared with the level of ubiquitination of the protein substrate in the absence of the test compound indicates that the test compound is a modulator of the ubiquitin E3 ligase activity of the complex. In particular embodiments, the method comprises identifying a compound that modules the histone or H2A (e.g., H2A-K119) ubiquitin E3 ligase activity of the complex.

Any method of detecting modulation of ubiquitin E3 ligase activity can be used, for example by, contacting the complex with a test compound in the presence of a protein substrate (e.g., a histone or H2A), E1, E2 and a labeled ubiquitin (e.g., FLAG-ubiquitin or a radiolabeled ubiquitin). Protein ubiquitination can be detected by detecting the labeled ubiquitin bound to the protein substrate. Alternatively, an antibody that is specific for the ubiquitinated protein can be used (e.g., an antibody directed against H2A ubiquitinated at K119). For example, the well-characterized monoclonal antibody (E6C5) is specific for ubiquitinated H2A (Vassilev, et al. (1995) *J. Cell Sci.* 108(Pt 3):1205-15). In one exemplary assay, the protein substrate can be bound to a surface (e.g., the bottom of a multi-well plate, a filter, a matrix or a bead). The surface can be contacted with the reagents as described above. The association of the labeled ubiquitin with the bound protein substrate can be detected to determine the level of ubiquitination.

An ELISA assay utilizing an antibody that is specific for the ubiquitinated form of the protein substrate (e.g., ubiquitinated H2A) is particularly well-suited for high though-put screening protocols. A protein substrate can be bound to a multi-well plate and ubiquitinated protein detected with an antibody that is specific for the ubiquitinated protein.

As used herein, the term "ubiquitin" encompasses the naturally-occurring 76-amino acid protein as well as variants and modified forms thereof, as long as the variant or modified ubiquitin functions substantially similarly to ubiquitin and can be used to detect ubiquitination in a ubiquitin E3 ligase assay.

H2A E3 ligase activity can be assessed by detecting ubiquitination of H2A or an artificial or synthetic H2A substrate.

Any suitable end-point for measuring ubiquitin E3 ligase activity can be used. For example, the screening methods can be practiced using the native or reconstituted complexes as the E3 enzyme in the ubiquitin ligase assays described in U.S. Pat. Nos. 6,737,244 and 6,740,495 (both to Issakani et al. and assigned to Rigel Pharmaceuticals).

To illustrate, a method of identifying a compound that modulates ubiquitin E3 ligase activity (e.g., histone or H2A ubiquitin E3 ligase activity) can comprise, consist essentially of or consist of: combining ubiquitin, E1, E2, E3 and a candidate ubiquitin ligase modulator, and measuring the amount of ubiquitin bound to E3. This method does not require a specific target protein (e.g., H2A) to be ubiquitinated. In a representative embodiment, a protein substrate (e.g., H2A) is specifically excluded from the assay mix.

In one embodiment of this assay, ubiquitin is in the form of tag1-ubiquitin. In another embodiment, E3 is in the form of tag2-E3. In these embodiments tag1 may be a label or a partner of a binding pair. In one embodiment, tag1 is a fluorescent label, in which case measuring the amount of ubiquitin bound to E3 may be by measuring luminescence.

In another embodiment, tag1 is a member of a binding pair chosen from the group antigen, biotin and calmodulin binding protein. In this latter embodiment, the partner of a binding pair may be labeled by indirect labeling, which may be by a fluorescent label or a label enzyme. The label enzyme may be horseradish peroxidase, alkaline phosphatase or glucose oxidase. When the indirect labeling is by a fluorescent label, measuring the amount of ubiquitin bound to E3 may be by measuring luminescence. In the case that the indirect labeling is by a label enzyme, said enzyme may be reacted with a substrate which produces a fluorescent product, in which case, measuring the amount of ubiquitin bound to E3 may be by measuring luminescence. In one embodiment of the method above, tag1 is a FLAG antigen. In this embodiment, indirect labeling may be by an anti-FLAG antibody.

In one aspect of the above method, tag2 is a surface binding molecule, which may be His-tag. In this latter case, the assaying may be performed in a multi-well plate comprising a surface substrate comprising nickel.

In a different embodiment of this method, when tag1 is a fluorescent label, the combining step further includes combining tag3-ubiquitin. Tag3 may be the second member of a fluorescence resonance energy transfer (FRET) pair with tag1 or it may be a quencher of tag1. In this embodiment, measuring the amount of ubiquitin bound to E3 may be by measuring fluorescent emission, which may involve measuring the fluorescent emission spectrum. The method may further comprise comparing the measured fluorescent emission spectrum with the fluorescent emission spectrum of unbound tag1- and tag3-ubiquitin. When measuring the amount of ubiquitin bound to E3 is by measuring the fluorescent emission spectrum, this measuring may be continuous or at specific time points following the original combining of materials.

As another alternative, a method of identifying a compound that modulates ubiquitin E3 ligase activity comprises, consists essentially of, or consists of combining tag1-ubiquitin, a candidate modulator, E1, E2 and tag2-E3 and measuring the amount of tag1-ubiquitin bound to tag2-E3. In another embodiment, this method further comprises combining tag1-ubiquitin, a candidate modulator, E1 and tag2-E2 and measuring the amount of tag1-ubiquitin bound to the tag2-E2. In a representative embodiment, a protein substrate (e.g., H2A) is specifically excluded from the method.

According to this method, tag1 may be a label or a partner of a binding pair. If tag1 is a label, it may be a fluorescent label, in which case, measuring the amount of bound tag1-ubiquitin may be by measuring luminescence. If tag1 is a partner of a binding pair, the potential binding pair partners, labeling options and subsequent measuring options are substantially as described for tag1 above.

In the above method, tag2 and tag3 may be surface substrate binding molecules. Options for such molecules and conditions for performing the method are as described above.

As a further alternative, a method of identifying a compound that modulates ubiquitin E3 ligase activity (e.g., histone or H2A ubiquitin E3 ligase activity) comprises, consists essentially of, or consists of combining tag1-ubiquitin and tag2-ubiquitin, a candidate modulator compound, E1, E2 and E3 under conditions in which ubiquitination can take place and measuring the amount or rate of ubiquitination. In this embodiment, tag1 and tag2 constitute a FRET pair or tag1 is a fluorescent label and tag2 is a quencher of tag1. In a representative embodiment of this method, measuring is by measuring the fluorescent emission spectrum from the combination, for example, continuously or at specific time points following combining the components. These measurements may be compared to the fluorescent emission spectrum of unbound tag1 and tag2 ubiquitin.

As another possibility, another assay method comprises, consists essentially of, or consists of combining a candidate ubiquitination modulator, tag1-ubiquitin and tag2-ubiquitin, E1, E2 and E3 under conditions in which ubiquitination can take place and measuring the amount or rate of ubiquitination. In this embodiment, tag1 and tag2 constitute a FRET pair or tag1 is a fluorescent label and tag2 is a quencher of tag1. In a representative embodiment of this method, measuring is by measuring the fluorescent emission spectrum from the combination, for example, continuously or at specific time points following combining the components. These measurements may be compared to the fluorescent emission spectrum of unbound tag1 and tag2 ubiquitin.

In the latter two assays described, the ubiquitin may be in the form tag1,3-ubiquitin and tag2,3-ubiquitin, wherein tag3 is a member of a binding pair, for example FLAG. In another embodiment of these assays, E3 may be in the form of tag4-E3, wherein tag4 is a surface substrate-bonding molecule.

Thus, in an exemplary embodiment, the method of identifying a compound that modulates ubiquitin E3 ligase activity (e.g., histone or H2A ubiquitin E3 ligase activity) comprises, consists essentially of, or consists of: a) combining: i) tag1-ubiquitin; ii) ubiquitin activating enzyme (E1); iii) ubiquitin conjugating enzyme (E2); iv) tag2-ubiquitin ligase (E3); and a (v) test compound; and b) measuring the amount of the tag1-ubiquitin bound to the ubiquitin ligase (E3), whereby the amount of the tag1-ubiquitin bound to the ubiquitin ligase (E3) indicates the ubiquitin ligase activity.

As another illustration, the assay comprises, consists essentially of, or consists of: a) combining, under conditions that favor ubiquitination activity: i) tag1-ubiquitin; ii) a test compound; iii) ubiquitin activating enzyme (E1); iv) ubiquitin conjugating enzyme (E2); and v) tag2-ubiquitin ligase (E3); b) measuring the amount of tag1-ubiquitin bound to the tag2-ubiquitin ligase (E3), whereby a difference in bound ubiquitin as compared with a reaction performed in the absence of the test compound indicates that the test compound is a ubiquitination modulator. In representative embodiments, the assay further comprises: c) combining, under conditions that favor ubiquitination activity: i) tag1-ubiquitin; ii) a test compound; iii) ubiquitin activating enzyme (E1); and iv) tag3-ubiquitin conjugating enzyme (E2); and d) measuring the amount of tag1-ubiquitin bound to the tag3-ubiquitin conjugating enzyme (E2), whereby a difference in bound ubiquitin as compared with a reaction performed in the absence of the test compound indicates that the test compound is a ubiquitination modulator.

Another possible assay comprises, consists essentially of, or consists of: a) combining, under conditions that favor ubiquitination activity: i) tag1-ubiquitin and tag2-ubiquitin, wherein tag1 and tag2 constitute a FRET pair or tag1 is a fluorescent label and tag2 is a quencher of tag1; ii) ubiquitin activating enzyme (E1); iii) ubiquitin conjugating enzyme (E2); iv) ubiquitin ligase (E3); and v) a candidate ubiquitination modulator; and b) measuring the amount or rate of ubiquitination, whereby a difference in the amount or rate of ubiquitination as compared with a reaction performed in the absence of the candidate modulator indicates that the candidate is a ubiquitination modulator. In representative assays, the combining step of (a) further comprises combining vi) a protein substrate (e.g., a histone or H2A).

A native or reconstituted complex as described herein with respect to screening methods can be used as the E3 enzyme in the foregoing assays.

In particular embodiments of the inventive screening methods, a reduction in ubiquitin E3 ligase activity (e.g., as determined by detecting ubiquitination of a protein substrate) as compared with the level of ubiquitin E3 ligase activity detected in the absence of the test compound indicates that the test compound is an inhibitor of the ubiquitin E3 ligase activity of the native or reconstituted complex. "Inhibitor" as used herein refers to the ability of the test compound to reduce the specified activity as compared to the level of activity in the absence of the test compound. In some embodiments, the test compound decreases or diminishes ubiquitin E3 ligase activity by at least about 10%, 25%, 35%, 40%, 50%, 60%, 75%, 80%, 90%, 95% or more as compared to the level of ubiquitin E3 ligase activity in the absence of the test compound. In particular embodiments, there is no or essentially no (at most, an insignificant amount, e.g., less than about 10% or even 5%) detectable activity.

In other embodiments, an increase in ubiquitin E3 ligase activity compared with the level of ubiquitin E3 ligase activity detected in the absence of the test compound indicates that the test compound is an activator of the ubiquitin E3 ligase activity of the native or reconstituted complex. "Activator" as used herein refers to the ability of the test compound to increase or prevent a reduction of the specified activity as compared to the level of activity in the absence of the test compound. In some embodiments, there is at least about a 1.1-fold, 1.25-fold, 1.5-fold, 2-fold, 3-fold, 4-fold, 5-fold, 6-fold, 8-fold, 10-fold, twelve-fold, fifteen-fold, fifty-fold, one hundred-fold or more increase in ubiquitin E3 ligase activity.

Inhibitors or activators identified in the first round of screening can optionally be analyzed individually in an assay to determine the $IC_{50}$ and specificity using ubiquitin E3 ligase assays as disclosed herein. Compounds having a low $IC_{50}$ and exhibiting specificity for the complexes disclosed herein can be further analyzed in tissue culture and/or in whole organism to determine their in vivo effects on ubiquitin E3 ligase activity, cell growth (e.g., by trypsinization and trypan-blue staining) and/or toxicity.

Test compounds that can be screened in accordance with the methods provided herein encompass numerous chemical classes including, but not limited to, synthetic or semi-synthetic chemicals, purified natural products, proteins, antibodies, peptides, peptide aptamers, nucleic acids, oligonucleotides, carbohydrates, lipids, or other small or large organic or inorganic molecules. Small molecules are desirable because such molecules are more readily absorbed after oral administration and have fewer potential antigenic determinants. Non-peptide agents or small molecule libraries are generally prepared by a synthetic approach, but recent advances in biosynthetic methods using enzymes may enable one to prepare chemical libraries that are otherwise difficult to synthesize chemically. Small molecule libraries can also be obtained from various commercial entities, for example, SPECS and BioSPEC B.V. (Rijswijk, the Netherlands), Chembridge Corporation (San Diego, Calif.), Comgenex USA Inc., (Princeton, N.J.), Maybridge Chemical Ltd. (Cornwall, UK), and Asinex (Moscow, Russia).

The method of identifying a compound that modulates the ubiquitin E3 ligase activity of the native or reconstituted complex can be a cell-based or cell-free method. Cell based methods can be carried out in cultured cells or in whole organisms. In representative embodiments, the method provides high throughput screening capabilities to identify modulators of the complex. For example, a cell-based, high throughput screening assay for use in accordance with the methods disclosed herein includes that described by Stockwell, et al. ((1999) Chem. Bio. 6:71-83), wherein biosynthetic processes such as DNA synthesis and post-translational processes are monitored in a miniaturized cell-based assay. For example, cultured cells can be contacted with the test compound and labeled ubiquitin for a time sufficient for ubiquitination of the protein substrate with the labeled ubiquitin. Ubiquitination of the protein can then be determined using any method known in the art. According to this embodiment, the enzyme complex can be the native complex or the reconstituted complex (e.g., the cell can be genetically modified to express the recombinant protein components of the complex).

As another illustration, a cell-based assay to identify modulators of endogenous ubiquitin E3 ligase activity can encompass the use of a reporter gene (such as luciferase, Green Fluorescent Protein, β-glucuronidase, β-galactosidase, and the like) operably linked to an upstream regulatory region of a target gene, such as a Hox gene, known to be targeted by the endogenous complex. Cells expressing the reporter construct can be exposed to the test compound and reporter gene expression can be monitored. To confirm that the modulator is specifically targeting the complex, a secondary in vitro screen can be employed using the native or reconstituted complex. Alternatively, components of the reconstituted complex can be expressed in a cell that lacks an endogenous complex and used to directly screen for modulators.

High throughput, cell-free methods for screening small molecule libraries for candidate protein-binding molecules are well-known in the art and can be employed to identify molecules that bind to at least one component of the complex and modulate the ubiquitin E3 ligase activity and/or binding to a protein substrate (e.g., a histone or H2A). For example, a protein substrate (e.g., free histones or nucleosomal histone substrates) can be coated on a multi-well plate or other suitable surface and a reaction mix containing the complex added to the protein substrate. Prior to, concurrent with, or subsequent to the addition of the complex, a test compound can be added to the well or surface containing the substrate (e.g., filter, well, matrix, bead, etc.). The reaction mixture can be washed with a solution that substantially reflects physiological conditions to remove unbound or weakly bound test compounds. Alternatively, the test compound can be immobilized and a solution of complex can be contacted with the well, matrix, filter, bead or other surface. The ability of a test compound to modulate binding of the complex to the protein substrate can be determined by labeling (e.g., radio-labeling or chemiluminescence) or competitive ELISA assays.

Library screening can be performed in any format that allows rapid preparation and processing of multiple reactions. Stock solutions of the test agents as well as assay components are prepared manually and all subsequent pipetting, diluting, mixing, washing, incubating, sample readout and data collecting is done using commercially available robotic pipetting equipment, automated work stations, and analytical instruments for detecting the signal generated by the assay, e.g., binding to a protein substrate and/or ubiquitination of a protein substrate (e.g., histone or H2A).

A variety of other reagents can be included in the screening assay of the instant invention. These include reagents like salts, ATP, neutral proteins, e.g., albumin, detergents, etc. which can be used to facilitate optimal protein-protein binding and/or enzymatic activity and/or reduce non-specific or background interactions. Also, reagents that otherwise improve the efficiency of the assay, such as protease inhibitors, nuclease inhibitors, anti-microbial agents, and the like may be used. The mixture of components can be added in any order that provides for the requisite binding and/or enzymatic activity.

The methods described above can further be practiced to identify a compound that modulates the ubiquitin E3 ligase activity of Bmi1 and/or Ring1 and/or Ring2, which may or may not be present as part of a complex. The Bmi1, Ring1 or Ring2 protein can be a native protein or a recombinant protein. Modification of the screening methods described above with respect to the native and reconstituted complexes for use in identifying compounds that modulate the ubiquitin E3 ligase activity of Bmi1 and/or Ring1 and/or Ring2 will be apparent to those skilled in the art.

The present invention also provides methods of identifying a candidate compound for treating hyperproliferative disorders such as tumors, cancers, and/or neoplastic disorders and/or pre-malignant and/or non-neoplastic and/or non-malignant hyperproliferative disorders, the methods comprising, consisting essentially of, or consisting of identifying a compound that modulates (e.g., enhances or inhibits) the H2A E3 ligase activity of a native or reconstituted complex. The complex can be a reconstituted or native complex as described herein, with the exception that the native or reconstituted complex can also be a complex as described by Levine et al., (2002) *Mol. Cell. Biology* 22:6070-6078 (dPRC1 and hPRC-H) and/or Francis et al., *Mol. Cell.* 8:545-556 (functional core of dPRC1).

In particular embodiments, the method comprises, consists essentially of, or consists of: contacting a native or reconstituted complex comprising Bmi1 and/or Ring1 and/or Ring2 and, optionally, HPH2 and/or HPC3 with an H2A substrate in the presence of a test compound, and detecting the level of H2A ubiquitination under conditions sufficient to provide H2A ubiquitination, wherein a change (e.g., increase or reduction) in H2A ubiquitination as compared with the level of H2A ubiquitination in the absence of the test compound indicates that the test compound is a candidate compound for the treatment of hyperproliferative disorders such as tumors, cancers, and/or neoplastic disorders and/or premalignant and/or non-neoplastic and/or non-malignant hyperproliferative disorders. In particular embodiments, the method comprises detecting the level of H2A-K119 ubiquitination.

The present invention also encompasses methods of identifying a candidate compound for treating cancer. Exemplary cancers include malignant disorders such as breast cancers; osteosarcomas; angiosarcomas; fibrosarcomas and/or other sarcomas; leukemias; lymphomas; sinus tumors; ovarian, cervical, uretal, bladder, prostate and/or other genitourinary cancers; colon, esophageal and/or stomach cancers and/or other gastrointestinal cancers; lung cancers; myelomas; pancreatic cancers; liver cancers; kidney cancers; endocrine cancers; skin cancers; and/or central nervous system (e.g., brain) and/or peripheral nervous system tumors, malignant and/or benign, including gliomas and/or neuroblastomas. By the terms "treating cancer" or "treatment of cancer," it is intended that the severity of the cancer is reduced or the cancer is at least partially eliminated and/or that the spread of the cancer is slowed and/or reduced.

In practicing methods of identifying compounds to treat hyperproliferative disorders, in particular cancer, H2A E3 ligase activity can be determined by any method known to those in the art as described above with respect to methods of identifying compounds that modulate H2A E3 ligase activity.

Also contemplated are methods of identifying a candidate compound for the treatment of hyperproliferative disorders such as tumors, cancers, and/or neoplastic disorders and/or pre-malignant and/or non-neoplastic and/or non-malignant hyperproliferative disorders, the method comprising, consisting essentially of, or consisting of identifying a compound that modulates (e.g., enhances or inhibits) the H2A E3 ligase activity (e.g., catalytic activity or enhancing activity) of Bmi1 and/or Ring1 and/or Ring2. In particular embodiments, the method comprises, consists essentially of, or consists of: contacting Bmi1 and/or Ring1 and/or Ring2 with an H2A substrate in the presence of a test compound, and detecting the level of H2A ubiquitination under conditions sufficient to provide H2A ubiquitination, wherein a change (e.g., reduction) in H2A ubiquitination as compared with the level of H2A ubiquitination in the absence of the test compound indicates that the test compound is a candidate compound for the treatment of hyperproliferative disorders such as tumors, cancers, and/or neoplastic disorders and/or premalignant and/or non-neoplastic and/or non-malignant hyperproliferative disorders. In particular embodiments, the method comprises detecting the level of H2A-K119 ubiquitination. The Bmi1, Ring1 or Ring2 protein can be a native protein or a recombinant protein.

The native and reconstituted complexes described herein are also implicated in Hox gene silencing, X-inactivation, genomic imprinting, stem cell pluripotency and/or germline development. Those skilled in the art will understand that the methods described above can be practiced to identify compounds that modulate Hox gene silencing, X-inactivation, genomic imprinting, stem cell pluripotency and/or germline development. For example, in some embodiments, compounds that enhance the H2A E3 ligase activity of the complex are identified as compounds that enhance Hox gene silencing, and compounds that inhibit H2A E3 ligase activity are identified as compounds that inhibit Hox gene silencing.

III. Additional Uses, Subjects, Pharmaceutical Formulations and Kits

In addition to the screening methods described above, the reconstituted or native complexes described herein can be used as a research reagent, e.g., to study the function of the complex or to study histone function. Further, the reconstituted and native complexes described in connection with screening methods can be used in methods of ubiquitinating a protein substrate (e.g., histone or H2A).

The present invention further provides methods of modulating ubiquitination of a protein substrate (for example, histone, H2A or H2A-K119 ubiquitination). In particular embodiments, the invention provides methods of modulating ubiquitination of a protein substrate, comprising, consisting essentially of or consisting of contacting a cell with a modulator of the ubiquitin E3 ligase activity of a native or reconstituted complex identified according to the screening methods described above. In some embodiments, the cell is a cultured cell. In other embodiments, the cell is a cell in vivo in a subject.

Subjects for which implementation of the present invention is appropriate include, but are not limited to, avians and mammals, with mammals being preferred. The term "avian" as used herein includes, but is not limited to, chickens, ducks, geese, quail, turkeys and pheasants. In some embodiments, human subjects are preferred. Human subjects include subjects of both genders and at any stage of development (i.e., neonate, infant, juvenile, adolescent, adult). While some embodiments of the present invention are primarily concerned with implementation regarding human subjects, the invention can also be carried out on animal subjects, particularly mammalian subjects such as non-human primates, bovines, ovines, caprines, equines, felines, canines, lagomorphs, rats, mice, etc. The present invention is carried out on animals for veterinary purposes, for drug screening and/or drug development purposes.

In further embodiments, the present invention provides pharmaceutical preparations comprising an inhibitor of the native or reconstituted complexes described above and a pharmaceutically acceptable carrier. The present invention further provides the use of the inhibitor of the reconstituted complex described above or the screening assays described herein for the preparation of a medicament.

In further embodiments, the present invention provides a kit for determining modulation of protein ubiquitination, the kit comprising, consisting essentially of, or consisting of (a) Bmi1, Ring2 or a native or reconstituted complex as described herein in connection with the screening methods (or nucleic acid encoding any of the foregoing); and (b) written instructions for methods for determining modulation of the ubiquitin E3 ligase activity (e.g., by detecting a ubiquitinated protein substrate, such as H2A), and optionally additional reagents or apparatus for carrying out methods for determining modulation of ubiquitin E3 ligase activity. In particular embodiments, the method is directed to determining modulation of histone, H2A or H2A-K119 ubiquitination.

The invention also provides a kit for ubiquitinating a target protein substrate, the kit comprising: (a) Bmi1, Ring2 or a native or reconstituted complex as descried herein in connection with the screening methods (or nucleic acid encoding any of the foregoing); and (b) written instructions for methods for ubiquitinating a target protein substrate, and optionally additional reagents or apparatus for carrying out methods for ubiquitinating a target protein substrate. Optionally, the target protein substrate is a histone or H2A .

The kits of the invention can further comprise an E1 ligase and/or an E2 ligase (or nucleic acids encoding the same). The kit can further comprise a labeled ubiquitin and, optionally, a reagent for detecting the labeled ubiquitin (e.g., an antibody against a peptide tag, such as FLAG). As further options, the kit can comprise a protein substrate (e.g., a histone or H2A as either free histone or in a nucleosome form), ATP, buffers, salts and/or other stock reagents for carrying out the inventive methods.

IV. Delivery Vectors

Any viral vector that is known in the art can be used in the present invention. Examples of such viral vectors include, but are not limited to vectors derived from: Adenoviridae; Baculoviridae; Birnaviridae; Bunyaviridae; Caliciviridae, Capillovirus group; Carlavirus group; Carmovirus virus group; Group Caulimovirus; Closterovirus Group; Commelina yellow mottle virus group; Comovirus virus group; Coronaviridae; PM2 phage group; Corcicoviridae; Group Cryptic virus; group Cryptovirus; Cucumovirus virus group Family ([PHgr]6 phage group; Cysioviridae; Group Carnation ringspot; Dianthovirus virus group; Group Broad bean wilt; Fabavirus virus group; Filoviridae; Flaviviridae; Furovirus group; Group Geminivirus; Group Giardiavirus; Hepadnaviridae; Herpesviridae; Hordeivirus virus group; Illarvirus virus group; Inoviridae; Iridoviridae; Leviviridae; Lipothrixviridae; Luteovirus group; Marafivirus virus group; Maize chlorotic dwarf virus group; icroviridae; Myoviridae; Necrovirus group; Nepovirus virus group; Nodaviridae; Orthomyxoviridae; Papovaviridae; Paramyxoviridae; Parsnip yellow fleck virus group; Partitiviridae; Parvoviridae; Pea enation mosaic virus group; Phycodnaviridae; Picomaviridae; Plasmaviridae; Prodoviridae; Polydnaviridae; Potexvirus group; Potyvirus; Poxviridae; Reoviridae; Retroviridae; Rhabdoviridae; Group Rhizidiovirus; Siphoviridae; Sobemovirus group; SSV 1-Type Phages; Tectiviridae; Tenuivirus; Tetraviridae; Group Tobamovirus; Group Tobravirus; Togaviridae; Group Tombusvirus; Group Torovirus; Totiviridae; Group Tymovirus; and plant virus satellites.

Protocols for producing recombinant viral vectors and for using viral vectors for nucleic acid delivery can be found in *Current Protocols in Molecular Biology*, Ausubel, F. M. et al. (eds.) Greene Publishing Associates, (1989) and other standard laboratory manuals (e.g., Vectors for Gene Therapy. In: *Current Protocols in Human Genetics*. John Wiley and Sons, Inc.: 1997).

In certain embodiments of the present invention, the delivery vector is a baculovirus vector.

The term "baculovirus" as used herein is intended to encompass all baculoviruses. Baculoviruses are divided into three subfamilies, including non-occluded baculoviruses (NOVs), granulosis viruses (GVs) and nuclear polyhedrosis viruses (NPVs). Although certain GVs and NOVs have been carefully studied, NPVs are the most thoroughly characterized of the baculovirus subfamilies. Examples of NPVs include *Autographa californica* NPV, *Spodoptera exigua* NPV, *Heliothis armigera* NPV, *Helicoverpa zea* NPV, *Spodoptera frugiperda* NPV, *Trichoplusia ni* NPV, *Mamestra brassicae* NPV, *Lymantria dispar* NPV, *Spodoptera litturalis* NPV, *Syngrapha facifera* NPV, *Choristoneura fumiferana* NPV, *Anticarsia gemmatalis* NPV, and *Heliothis virescens* NPV.

Standard procedures for engineering baculoviruses having various foreign genetic elements are well known in the art. Procedures for introducing recombinant baculoviruses into insects or cells thereof are also well known. See, e.g., Pfeifer et al., 1997, Gene 188:183-190; and Clem et al., 1994, J Virol 68:6759-6762. Baculoviruses expressing mammalian RbAp48 are described in Cao et al. *Mol. Cell* 15:57-67 (2004) and Zhang et al. *Genes Dev* 13:1924-1935 (1999).

The term "adenovirus" as used herein is intended to encompass all adenoviruses, including the Mastadenovirus and Aviadenovirus genera. To date, at least forty-seven human serotypes of adenoviruses have been identified (see, e.g., FIELDS et al., VIROLOGY, volume 2, chapter 67 (3d ed., Lippincott-Raven Publishers). Preferably, the adenovirus is a serogroup C adenovirus, still more preferably the adenovirus is serotype 2 (Ad2) or serotype 5 (Ad5).

The various regions of the adenovirus genome have been mapped and are understood by those skilled in the art (see, e.g., FIELDS et al., VIROLOGY, volume 2, chapters 67 and 68 (3d ed., Lippincott-Raven Publishers). The genomic sequences of the various Ad serotypes, as well as the nucleotide sequence of the particular coding regions of the Ad genome, are known in the art and can be accessed, e.g., from GenBank and NCBI (see, e.g., GenBank Accession Nos. J0917, M73260, X73487, AF108105, L19443, NC 003266 and NCBI Accession Nos. NC 001405, NC 001460, NC 002067, NC 00454).

Those skilled in the art will appreciate that the inventive adenovirus vectors can be modified or "targeted" as described in Douglas et al., (1996) *Nature Biotechnology* 14:1574; U.S. Pat. No. 5,922,315 to Roy et al.; U.S. Pat. No. 5,770,442 to Wickham et al.; and/or U.S. Pat. No. 5,712,136 to Wickham et al.

An adenovirus vector genome or rAd vector genome will typically comprise the Ad terminal repeat sequences and packaging signal. An "adenovirus particle" or "recombinant adenovirus particle" comprises an adenovirus vector genome or recombinant adenovirus vector genome, respectively, packaged within an adenovirus capsid. Generally, the adenovirus vector genome is most stable at sizes of about 28 kb to 38 kb (approximately 75% to 105% of the native genome size). In the case of an adenovirus vector containing large deletions and a relatively small heterologous nucleic acid of interest, "stuffer DNA" can be used to maintain the total size of the vector within the desired range by methods known in the art.

Normally, adenoviruses bind to a cell surface receptor (CAR) of susceptible cells via the knob domain of the fiber protein on the virus surface. The fiber knob receptor is a 45 kDa cell surface protein which has potential sites for both glycosylation and phosphorylation. (Bergelson et al., (1997), *Science* 275:1320-1323). A secondary method of entry for adenovirus is through integrins present on the cell surface. Arginine-Glycine-Aspartic Acid (RGD) sequences of the adenoviral penton base protein bind integrins on the cell surface.

The adenovirus genome can be manipulated such that it encodes and expresses a nucleic acid of interest but is inactivated in terms of its ability to replicate in a normal lytic viral life cycle. See, for example, Berkner et al. (1988) *BioTechniques* 6:616; Rosenfeld et al. (1991) *Science* 252:431-434; and Rosenfeld et al. (1992) *Cell* 68:143-155. Representative adenoviral vectors derived from the adenovirus strain Ad type 5 d1324 or other strains of adenovirus (e.g., Ad2, Ad3, Ad7 etc.) are known to those skilled in the art.

Recombinant adenoviruses can be advantageous in certain circumstances in that they are not capable of infecting non-dividing cells and can be used to infect a wide variety of cell types, including epithelial cells. Furthermore, the virus particle is relatively stable and amenable to purification and concentration, and can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., as occurs with retroviral DNA). Moreover, the carrying capacity of the adenoviral genome for foreign DNA is large relative to other delivery vectors (Haj-Ahmand and Graham (1986) *J. Virol.* 57:267).

In particular embodiments, the adenovirus genome contains a deletion therein, so that at least one of the adenovirus genomic regions does not encode a functional protein. For example, first-generation adenovirus vectors are typically deleted for the E1 genes and packaged using a cell that expresses the E1 proteins (e.g., 293 cells). The E3 region is also frequently deleted as well, as there is no need for complementation of this deletion. In addition, deletions in the E4, E2a, protein IX, and fiber protein regions have been described, e.g., by Armentano et al, (1997) *J. Virology* 71:2408, Gao et al., (1996) *J. Virology* 70:8934, Dedieu et al., (1997) *J. Virology* 71;4626, Wang et al., (1997) *Gene Therapy* 4:393, U.S. Pat. No. 5,882,877 to Gregory et al. (the disclosures of which are incorporated herein in their entirety). Preferably, the deletions are selected to avoid toxicity to the packaging cell. Wang et al., (1997) *Gene Therapy* 4:393, has described toxicity from constitutive co-expression of the E4 and E1 genes by a packaging cell line. Toxicity can be avoided by regulating expression of the E1 and/or E4 gene products by an inducible, rather than a constitutive, promoter. Combinations of deletions that avoid toxicity or other deleterious effects on the host cell can be routinely selected by those skilled in the art.

As further examples, in particular embodiments, the adenovirus is deleted in the polymerase (pol), preterminal protein (pTP), IVa2 and/or 100K regions (see, e.g., U.S. Pat. No. 6,328,958; PCT publication WO 00/12740; and PCT publication WO 02/098466; Ding et al., (2002) *Mol. Ther.* 5:436; Hodges et al., *J. Virol.* 75:5913; Ding et al., (2001) *Hum Gene Ther* 12:955; the disclosures of which are incorporated herein by reference in their entireties for the teachings of how to make and use deleted adenovirus vectors for gene delivery).

The term "deleted" adenovirus as used herein refers to the omission of at least one nucleotide from the indicated region of the adenovirus genome. Deletions can be greater than about 1, 2, 3, 5, 10, 20, 50, 100, 200, or even 500 nucleotides. Deletions in the various regions of the adenovirus genome can be about at least 1%, 5%, 10%, 25%, 50%, 75%, 90%, 95%, 99%, or more of the indicated region. Alternately, the entire region of the adenovirus genome is deleted. Preferably, the deletion will prevent or essentially prevent the expression of a functional protein from that region. In general, larger deletions are preferred as these have the additional advantage that they will increase the carrying capacity of the deleted adenovirus for a heterologous nucleotide sequence of interest. The various regions of the adenovirus genome have been mapped and are understood by those skilled in the art (see, e.g., FIELDS et al., VIROLOGY, volume 2, chapters 67 and 68 (3d ed., Lippincott-Raven Publishers).

Those skilled in the art will appreciate that typically, with the exception of the E3 genes, any deletions will need to be complemented in order to propagate (replicate and package) additional virus, e.g., by transcomplementation with a packaging cell.

The present invention can also be practiced with "gutted" adenovirus vectors (as that term is understood in the art, see e.g., Lieber et al., (1996) *J. Virol.* 70:8944-60) in which essentially all of the adenovirus genomic sequences are deleted.

Adeno-associated viruses (AAV) have also been employed as nucleic acid delivery vectors. For a review, see Muzyczka et al. *Curr. Topics in Micro. and Immunol.* (1992) 158:97-129). AAV are parvoviruses and have small icosahedral virions, 18-26 nanometers in diameter and contain a single stranded genomic DNA molecule 4-5 kilobases in size. The viruses contain either the sense or antisense strand of the DNA molecule and either strand is incorporated into the virion. Two open reading frames encode a series of Rep and Cap polypeptides. Rep polypeptides (Rep50, Rep52, Rep68 and Rep78) are involved in replication, rescue and integration of the AAV genome, although significant activity can be observed in the absence of all four Rep polypeptides. The Cap proteins (VP1, VP2, VP3) form the virion capsid. Flanking the rep and cap open reading frames at the 5' and 3' ends of the genome are 145 basepair inverted terminal repeats (ITRs), the first 125 basepairs of which are capable of forming Y- or T-shaped duplex structures. It has been shown that the ITRs represent the minimal cis sequences required for replication, rescue, packaging and integration of the AAV genome. Typically, in recombinant AAV vectors (rAAV), the entire rep and cap coding regions are excised and replaced with a heterologous nucleic acid of interest.

AAV are among the few viruses that can integrate their DNA into non-dividing cells, and exhibit a high frequency of stable integration into human chromosome 19 (see, for example, Flotte et al. (1992) *Am. J. Respir. Cell. Mol. Biol.* 7:349-356; Samulski et al., (1989) *J Virol.* 63:3822-3828; and McLaughlin et al., (1989) *J. Virol.* 62:1963-1973). A variety of nucleic acids have been introduced into different cell types using AAV vectors (see, for example, Hermonat et al., (1984) *Proc. Natl. Acad. Sci. USA* 81:6466-6470; Tratschin et al., (1985) *Mol. Cell. Biol.* 4:2072-2081; Wondisford et al., (1988) *Mol. Endocrinol.* 2:32-39; Tratschin et al., (1984) *J. Virol.* 51:611-619; and Flotte et al., (1993) *J. Biol. Chem.* 268:3781-3790).

A rAAV vector genome will typically comprise the AAV terminal repeat sequences and packaging signal. An "AAV particle" or "rAAV particle" comprises an AAV vector genome or rAAV vector genome, respectively, packaged within an AAV capsid. The rAAV vector itself need not contain AAV genes encoding the capsid and Rep proteins. In particular embodiments of the invention, the rep and/or cap genes are deleted from the AAV genome. In a representative embodiment, the rAAV vector retains only the terminal AAV sequences (ITRs) necessary for integration, excision, replication.

Sources for the AAV capsid genes can include serotypes AAV-1, AAV-2, AAV-3 (including 3a and 3b), AAV-4, AAV-5, AAV-6, AAV-7, AAV-8, as well as bovine AAV and avian AAV, and any other virus classified by the International Committee on Taxonomy of Viruses (ICTV) as an AAV (see, e.g., FIELDS et al., VIROLOGY, volume 2, chapter 69 (4th ed., Lippincott-Raven Publishers).

Because of packaging limitations, the total size of the rAAV genome will preferably be less than about 5.2, 5, 4.8, 4.6, 4.5 or 4.2 kb in size.

Any suitable method known in the art can be used to produce AAV vectors expressing the nucleic acids encoding the components of the complex of this invention (see, e.g., U.S. Pat. Nos. 5,139,941; 5,858,775; 6,146,874 for illustrative methods). In one particular method, AAV stocks can be produced by co-transfection of a rep/cap vector encoding AAV packaging functions and the template encoding the AAV vDNA into human cells infected with the helper adenovirus (Samulski et al., (1989) *J. Virology* 63:3822).

In other particular embodiments, the adenovirus helper virus is a hybrid helper virus that encodes AAV Rep and/or capsid proteins. Hybrid helper Ad/AAV vectors expressing AAV rep and/or cap genes and methods of producing AAV stocks using these reagents are known in the art (see, e.g., U.S. Pat. Nos. 5,589,377; and 5,871,982, 6,251,677; and 6,387,368). Preferably, the hybrid Ad of the invention expresses the AAV capsid proteins (i.e., VP1, VP2, and VP3). Alternatively, or additionally, the hybrid adenovirus can express one or more of AAV Rep proteins (i.e., Rep40, Rep52, Rep68 and/or Rep78). The AAV sequences can be operatively associated with a tissue-specific or inducible promoter.

The AAV rep and/or cap genes can alternatively be provided by a packaging cell that stably expresses the genes (see, e.g., Gao et al., (1998) *Human Gene Therapy* 9:2353; Inoue et al., (1998) *J. Virol.* 72:7024; U.S. Pat. No. 5,837,484; WO 98/27207; U.S. Pat. No. 5,658,785; WO 96/17947).

Another vector for use in the present invention comprises Herpes Simplex Virus (HSV). Herpes simplex virions have an overall diameter of 150 to 200 nm and a genome consisting of one double-stranded DNA molecule that is 120 to 200 kilobases in length. Glycoprotein D (gD) is a structural component of the HSV envelope that mediates virus entry into host cells. The initial interaction of HSV with cell surface heparin sulfate proteoglycans is mediated by another glycoprotein, glycoprotein C (gC) and/or glycoprotein B (gB). This is followed by interaction with one or more of the viral glycoproteins with cellular receptors. It has been shown that glycoprotein D of HSV binds directly to Herpes virus entry mediator (HVEM) of host cells. HVEM is a member of the tumor necrosis factor receptor superfamily (Whitbeck et al., (1997), *J. Virol.;* 71:6083-6093). Finally, gD, gB and the complex of gH and gL act individually or in combination to trigger pH-independent fusion of the viral envelope with the host cell plasma membrane. The virus itself is transmitted by direct contact and replicates in the skin or mucosal membranes before infecting cells of the nervous system for which HSV has particular tropism. It exhibits both a lytic and a latent function. The lytic cycle results in viral replication and cell death. The latent function allows for the virus to be maintained in the host for an extremely long period of time.

HSV can be modified for the delivery of nucleic acids to cells by producing a vector that exhibits only the latent function for long-term gene maintenance. HSV vectors are useful for nucleic acid delivery because they allow for a large DNA insert of up to or greater than 20 kilobases; they can be produced with extremely high titers; and they have been shown to express nucleic acids for a long period of time in the central nervous system as long as the lytic cycle does not occur.

In other particular embodiments of the present invention, the delivery vector of interest is a retrovirus. Retroviruses normally bind to a virus-specific cell surface receptor, e.g., CD4 (for HIV); CAT (for MLV-E; ecotropic Murine leukemic virus E); RAM1/GLVR2 (for murine leukemia virus-A; MLV-A); GLVR1 (for Gibbon Ape leukemia virus (GALV) and Feline leukemia virus B (FeLV-B)). The development of specialized cell lines (termen "packaging cells") which produce only replication-defective retroviruses has increased the utility of retroviruses for gene therapy, and defective retroviruses are characterized for use in gene transfer for gene therapy purposes (for a review, see Miller, (1990) *Blood* 76:271). A replication-defective retrovirus can be packaged into virions which can be used to infect a target cell through the use of a helper virus by standard techniques.

Yet another suitable vector is a poxvirus vector. These viruses are very complex, containing more than 100 proteins, although the detailed structure of the virus is presently unknown. Extracellular forms of the virus have two membranes while intracellular particles only have an inner membrane. The outer surface of the virus is made up of lipids and proteins that surround the biconcave core. Poxviruses are antigenically complex, inducing both specific and cross-reacting antibodies after infection. Poxvirus receptors are not presently known, but it is likely that there exists more than one given the tropism of poxvirus for a wide range of cells. Poxvirus gene expression is well studied due to the interest in using vaccinia virus as a vector for expression of nucleic acids.

In addition to viral transfer methods, such as those illustrated above, non-viral methods can also be employed. Many non-viral methods of nucleic acid transfer rely on normal mechanisms used by mammalian cells for the uptake and intracellular transport of macromolecules. In particular embodiments, non-viral nucleic acid delivery systems rely on endocytic pathways for the uptake of the nucleic acid molecule by the targeted cell. Exemplary nucleic acid delivery systems of this type include liposomal derived systems, polylysine conjugates, and artificial viral envelopes.

Plasmid vectors can be used in the practice of the present invention. Naked plasmids can be introduced into muscle cells by injection into the tissue. Expression can extend over many months, although the number of positive cells is typically low (Wolff et al., (1989) *Science* 247:247). Cationic lipids have been demonstrated to aid in introduction of nucleic acids into some cells in culture (Felgner and Ringold, (1989) *Nature* 337:387). Injection of cationic lipid plasmid DNA complexes into the circulation of mice has been shown to result in expression of the DNA in lung (Brigham et al., (1989) *Am. J. Med. Sci.* 298:278). One advantage of plasmid DNA is that it can be introduced into non-replicating cells.

V. Expression Systems for the Reconstituted Complex and Components thereof

As indicated above, the components of the reconstituted complex can be produced in, and optionally purified from, cultured cells or organisms expressing one or more heterologous nucleic acids encoding the proteins of the complex for a variety of purposes (e.g., screening assays to identify compounds for modulating ubiquitin E3 ligase activity or for treating cancer, large-scale protein production and/or research purposes).

Generally, the heterologous nucleic acid is incorporated into an expression vector (viral or nonviral as described above). Expression vectors compatible with various host cells are well known in the art and contain suitable elements for transcription and translation of nucleic acids. Typically, an expression vector contains an "expression cassette," which includes, in the 5' to 3' direction, a promoter, a coding sequence encoding a Ring1, Ring2, Bmi1, HPC3 and/or HPH2 protein operatively associated with the promoter, and, optionally, a termination sequence including a stop signal for RNA polymerase and a polyadenylation signal for polyadenylase.

Expression vectors can be designed for expression of polypeptides in prokaryotic or eukaryotic cells. For example, polypeptides can be expressed in bacterial cells such as *E. coli*, insect cells (e.g., in the baculovirus expression system), yeast cells or mammalian cells. Some suitable host cells are discussed further in Goeddel, *Gene Expression Technology*: Methods in Enzymology 185, Academic Press, San Diego, Calif. (1990). Examples of vectors for expression in yeast S. cerevisiae include pYepSec1 (Baldari et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.). Baculovirus vectors available for expression of nucleic acids to produce proteins in cultured insect cells (e.g., Sf 9 cells) are described above and include the pAc series (Smith et al., (1983) *Mol. Cell. Biol.* 3:2156-2165) and the pVL series (Lucklow, V. A., and Summers, M. d. (1989) *Virology* 170:31-39).

Examples of mammalian expression vectors include pCDM8 (Seed, (1987) *Nature* 329:840) and pMT2PC (Kaufman et al. (1987), *EMBO J.* 6:187-195). When used in mammalian cells, the expression vector's control functions are often provided by viral regulatory elements. For example, commonly used promoters are derived from polyoma, adenovirus 2, cytomegalovirus and Simian Virus 40.

Vectors can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA) into a host cell, including calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al. (Molecular Cloning: A Laboratory Manual, 2nd Edition, Cold Spring Harbor Laboratory press (1989)), and other laboratory manuals.

When producing stably transformed cells, often only a small fraction of cells (in particular, mammalian cells) integrate a foreign DNA into their genome. In order to identify and select these integrants, a nucleic acid that encodes a selectable marker (e.g., resistance to antibiotics) can be introduced into the host cells along with the nucleic acid of interest. Preferred selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid can be identified by drug selection (e.g., cells that have incorporated the selectable marker gene will survive, while the other cells die).

Recombinant proteins can also be produced in a transgenic plant in which the isolated nucleic acid encoding the protein is inserted into the nuclear or plastidic genome. Plant transformation is known as the art. See, in general, *Methods in Enzymology* Vol. 153 ("Recombinant DNA Part D") 1987, Wu and Grossman Eds., Academic Press and European Patent Application EP 693554.

Foreign nucleic acids can be introduced into plant cells or protoplasts by several methods. For example, nucleic acid can be mechanically transferred by microinjection directly into plant cells by use of micropipettes. Foreign nucleic acid can also be transferred into a plant cell by using polyethylene glycol which forms a precipitation complex with the genetic material that is taken up by the cell (Paszkowski et al. (1984) *EMBO J.* 3:2712-22). Foreign nucleic acid can be introduced into a plant cell by electroporation (Fromm et al. (1985) *Proc. Natl. Acad. Sci. USA* 82:5824). In this technique, plant protoplasts are electroporated in the presence of plasmids or nucleic acids containing the relevant genetic construct. Electrical impulses of high field strength reversibly permeabilize biomembranes allowing the introduction of the plasmids. Electroporated plant protoplasts reform the cell wall, divide, and form a plant callus. Selection of the transformed plant cells comprising the foreign nucleic acid can be accomplished using phenotypic markers.

Cauliflower mosaic virus (CaMV) can be used as a vector for introducing foreign nucleic acids into plant cells (Hohn et al. (1982) "Molecular Biology of Plant Tumors," Academic Press, New York, pp. 549-560; Howell, U.S. Pat. No. 4,407, 956). CaMV viral DNA is inserted into a parent bacterial plasmid creating a recombinant DNA molecule which can be propagated in bacteria. The recombinant plasmid can be further modified by introduction of the desired DNA sequence. The modified viral portion of the recombinant plasmid is then excised from the parent bacterial plasmid, and used to inoculate the plant cells or plants.

High velocity ballistic penetration by small particles can be used to introduce foreign nucleic acid into plant cells. Nucleic acid is disposed within the matrix of small beads or particles, or on the surface (Klein et al. (1987) *Nature* 327:70-73). Although typically only a single introduction of a new nucleic acid segment is required, this method also provides for multiple introductions.

A nucleic acid can be introduced into a plant cell by infection of a plant cell, an explant, a meristem or a seed with *Agrobacterium tumefaciens* transformed with the nucleic acid. Under appropriate conditions, the transformed plant cells are grown to form shoots, roots, and develop further into plants. The nucleic acids can be introduced into plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al. (1984) "Inheritance of Functional Foreign Genes in Plants," *Science* 233: 496498; Fraley et al. (1983) *Proc. Natl. Acad. Sci. USA* 80:4803).

The present invention is explained in greater detail in the following non-limiting Examples.

EXAMPLE 1

Identification of H2A E3 Ligase Activity

Methodology. The E3 ligase responsible for H2A ubiquitination was identified by developing an assay to monitor enzymatic activity. In this assay, histone octamers (5 µg) or oligonucleosomes (5 µg) were incubated with 20 µL protein fractions or recombinant proteins in a 36 µL reaction containing 50 mM Tris-HCl (pH 7.9), 5 mM $MgCl_2$, 2 mM NaF, 0.6 mM DTT, 2 mM ATP, 10 µM Okada acid, 0.1 µg ubiquitin-activating enzyme E1 (CALBIOCHEM®, LaJolla, Calif.), 0.6 µg ubiquitin-conjugating enzyme Ubc5c, 1 µg FLAG®-ubiquitin (Sigma, St. Louis, Mo.). After incubation at 37° C. for 1 hour, the reaction was terminated by addition of SDS-polyacrylamide gel electrophoresis (PAGE) loading buffer.

The proteins were resolved in 8-15% SDS-PAGE, blotted and detected with the anti-FLAG® antibody.

Results. Western blot analysis of the reactions containing E1, E2, ATP, FLAG®-ubiquitin (F-Ub) and HeLa nuclear protein fractions, revealed a positive, FLAG®-tagged signal around 25 kDa, the size of H2A plus F-Ub, indicating that a potential H2A E3 ligase activity was present in the corresponding fractions (lanes 19-21 of the rectangle area; FIG. 1A). The activity was nucleosomal histone specific, as parallel experiments using core histone octamers failed to detect such an activity (FIG. 1A, lanes 8-10). A weak activity potentially for H2B was also detected (FIG. 1A, lane 20). Since the 0.5 M P11 fraction derived from the nuclear pellet had the strongest activity, further analysis was conducted on this fraction. To verify the presence of an E3 ligase activity in the 0.5 M P11 fraction, the dependency of activity on each of the components in the reaction was tested. Results shown in FIG. 1B indicate that the appearance of the ubiquitinated protein bands around 25 kDa was dependent upon each component.

Figure 1C:
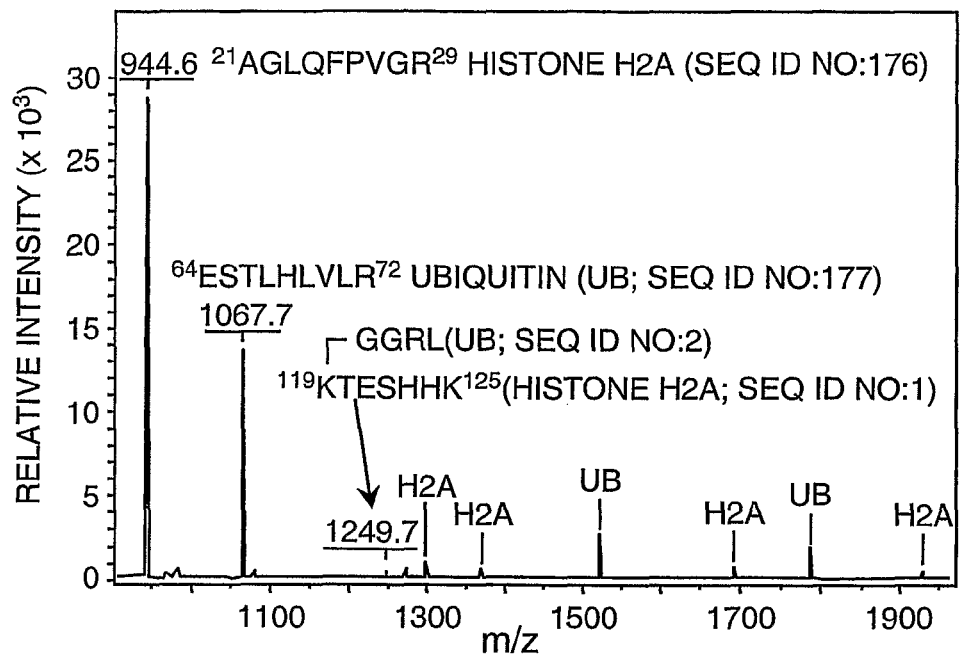

To ascertain whether the 25 kDa protein band was uH2A, a protein band corresponding to ubiquitinated H2A was excised and subjected to trypsin digestion and MALDI-TOF MS analysis (Devroe, et al. (2004) *J. Biol. Chem.* 279:24444-51). A peptide corresponding to residues 119-125 of uH2A (Lys*-Thr-Glu-Ser-His-His-Lys; SEQ ID NO:1) was identified (FIG. 1C). A peptide corresponding to the C-terminal ubiquitin (i.e., Lys-Arg-Gly-Gly; SEQ ID NO:2) attached to lysine 119 of H2A (indicated by * in SEQ ID NO:1) was also identified. In addition, an antibody against uH2A recognized the protein band specifically. Thus, an E3 ligase activity was identified that specifically ubiquitinates H2A at lysine 119, a known in vivo ubiquitination site (Nickel & Davie (1989) *Biochemistry* 28:964-8).

EXAMPLE 2

Purification of H2A E3 Ligase Activity

Methodology. HeLa nuclear proteins were separated into nuclear extract and nuclear pellet according to established methods (Wang, et al. (2001) *Mol. Cell* 8:1207-17). Nuclear pellet solubilization, fractionation on DEAE 52, P11 and DEAE 5PW columns were performed according to well-known methods (Cao, et al. (2002) *Science* 298:1039-43). Proteins bound to DEAE 5PW column were eluted with a 12-column volume linear gradient from 50 mM to 500 mM ammonium sulfate in buffer D [20 mM Tris-HCl (pH 7.9), 0.1 mM EDTA, 2 mM DTT, 0.2 mM PMSF, and 10% glycerol]. Fractions containing the ubiquitin ligase activity for H2A were eluted from the column between 70-150 mM ammonium sulfate. Active fractions were then combined and adjusted to 500 mM ammonium sulfate with saturated ammonium sulfate before loading onto a 22 mL Phenyl SEPHAROSE® column (Pharmacia, Piscataway, N.J.). The Phenyl SEPHAROSE® column was eluted with a 20-column volume linear gradient from 500 mM to 0 mM ammonium sulfate in buffer D. The H2A ubiquitin ligase activity eluted between 345-240 mM ammonium sulfate. Active fractions were pooled and concentrated to 5 mL before loading onto a 120 mL SEPHACRYL™ 300 gel filtration column (Pharmacia, Piscataway, N.J.). The ubiquitin ligase activity was eluted between 220-443 kDa. Active fractions were combined and dialyzed against buffer P [5 mM HEPES-KOH (pH 7.5), 40 mM KCl, 0.01% TRITON™ X-100, 0.01 mM CaCl$_2$, 0.5 mM PMSF, 1 mM DTT, and 10% glycerol] containing 10 mM potassium phosphate (BP10) and loaded onto a 5 mL hydroxyapatite column (BIO-RAD®, Hercules, Calif.). The bound proteins were eluted with a 20-column volume linear gradient from BP10 to BP600. The H2A ubiquitin ligase activity was eluted from the column between 340-550 mM potassium phosphate. Active fractions were combined and loaded onto a 1 mL MONOQ™ column (Pharmacia, Piscataway, N.J.) after dialysis against buffer C [40 mM HEPES-KOH (pH 7.9), 0.1 mM EDTA, 2 mM DTT, 0.2 mM PMSF, and 10% glycerol] containing 150 mM KCl. Bound proteins were eluted with a 20-column volume linear gradient from 150 mM to 500 mM KCl in buffer C. The H2A ubiquitin ligase activity was eluted between 220-320 mM KCl. To identify the proteins that co-eluted with the H2A ubiquitin ligase activity, active fractions between 29-32 were combined, dialyzed to BC50 and bound to a 200 µL P11 column before being eluted with BC600. The eluted proteins were resolved in 8-15% gradient SDS-PAGE. After COOMASSIE® staining and destaining, candidate polypeptides were excised and subjected to trypsin digestion and a combination of peptide mass fingerprinting using MALDI-TOF MS and MS sequencing using MALDI-TOF/TOF MS/MS (Devroe, et al. (2004) *J. Biol. Chem.* 279:24444-51; Sebastiaan Winkler, et al. (2002) *Methods* 26:260-9).

Figure 2A:
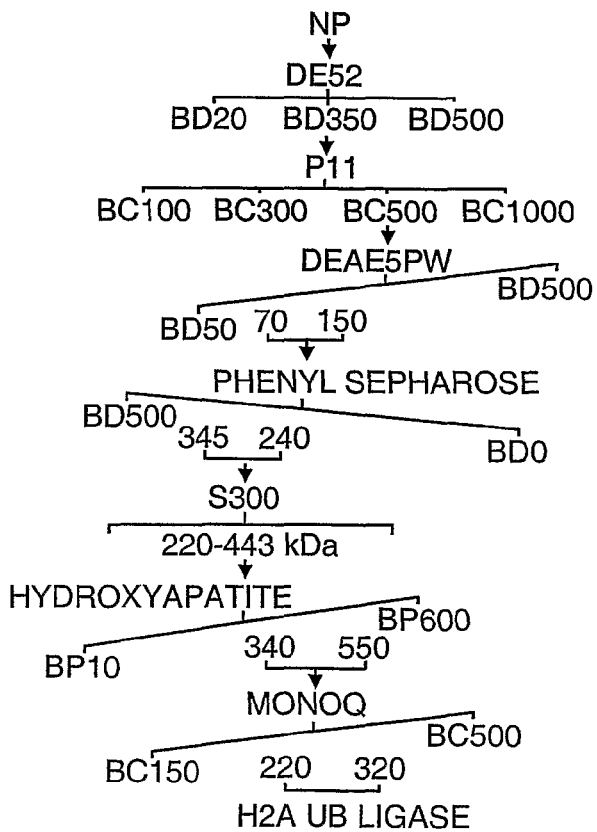
FIGS. 2A-2E show the purification and identification of the H2A ubiquitination ligase complex.
Figure 2B:
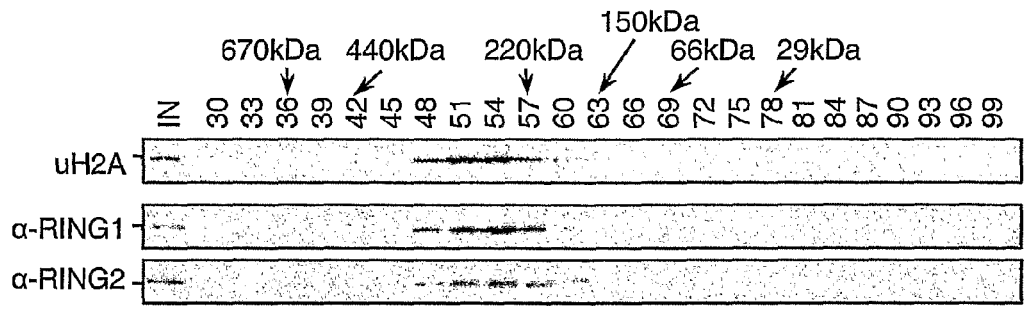
Figure 2C:
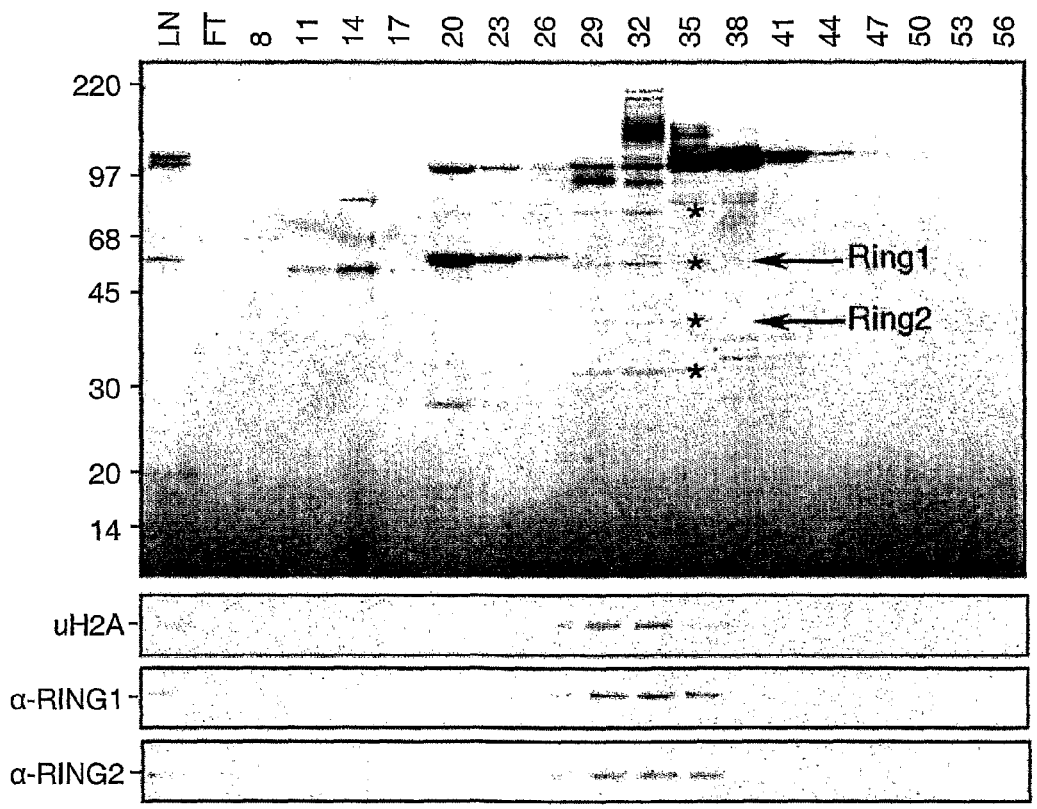

Results. H2A E3 ligase activity was monitored through the seven chromatography columns (FIG. 2A). After purification of the 0.5 M P11 fraction through DEAE 5PW and Phenyl SEPHAROSE® columns, the relative mass of the enzyme complex was determined on a S300 gel-filtration column and found to be about 250-300 kDa (FIG. 2B, top panel). Further purification on two additional columns identified four candidate protein bands (FIG. 2C, top panel, marked by *) which correlated with enzymatic activity (FIG. 2C, second panel). The limited amount of sample prevented further purification of the complex. Thus, MONOQ™ eluted samples were pooled between fractions 29-32. After concentration, the samples were resolved on SDS-PAGE and the four candidate protein bands were recovered for identification. Mass spectrometry analysis identified the middle two protein bands as Ring1 and Ring2 (Lee, et al. (2001) *FEBS Lett.* 503:61-4; Satijn, et al. (1997) *Mol. Cell Biol.* 17:4105-13), two human homologs of *Drosophila* PRC1 core component dRing/Sce (Sex combs extra) (Fritsch, et al. (2003) *Mech. Dev.* 120:949-54; Gorfinkiel, et al. (2004) *Mech. Dev.* 121:449-62; Francis, et al. (2001) *Mol. Cell* 8:545-56). Western blot analysis confirmed that both proteins co-fractionated with the ligase activity on the MONOQ™ column (FIG. 2C, bottom two panels), as well as on the S300 column (FIG. 2B, bottom two panels). However, the other two protein bands were not identified.

EXAMPLE 3

Purification and Identification of Histone H2A Ubiquitin Ligase Complex

Methodology. To define the composition of the E3 ligase complex, immunoaffinity purification was performed using an aliquot of hydroxyapatite input material and an antibody against Ring1. For immunopurification of the Ring1 complex, affinity purified Ring1 antibodies (Schoorlemmer, et al. (1997) *EMBO J.* 16:5930-42) were cross-linked to protein A agarose beads according to standard methods (Zhang, et al. (1998) *Cell* 95:279-89) and incubated at 4° C. for 4 hours with an aliquot of hydroxyapatite input dialyzed against BC50. After three washings with BC500 and two washings with BC50, beads were divided into four aliquots for ubiquitin ligase assays, western blot analysis, silver stain analysis, and protein identification (5-fold more than the other aliquots).

Protein identification was performed as described above. Parallel experiments with rabbit IgG was also performed.

Figure 2D:
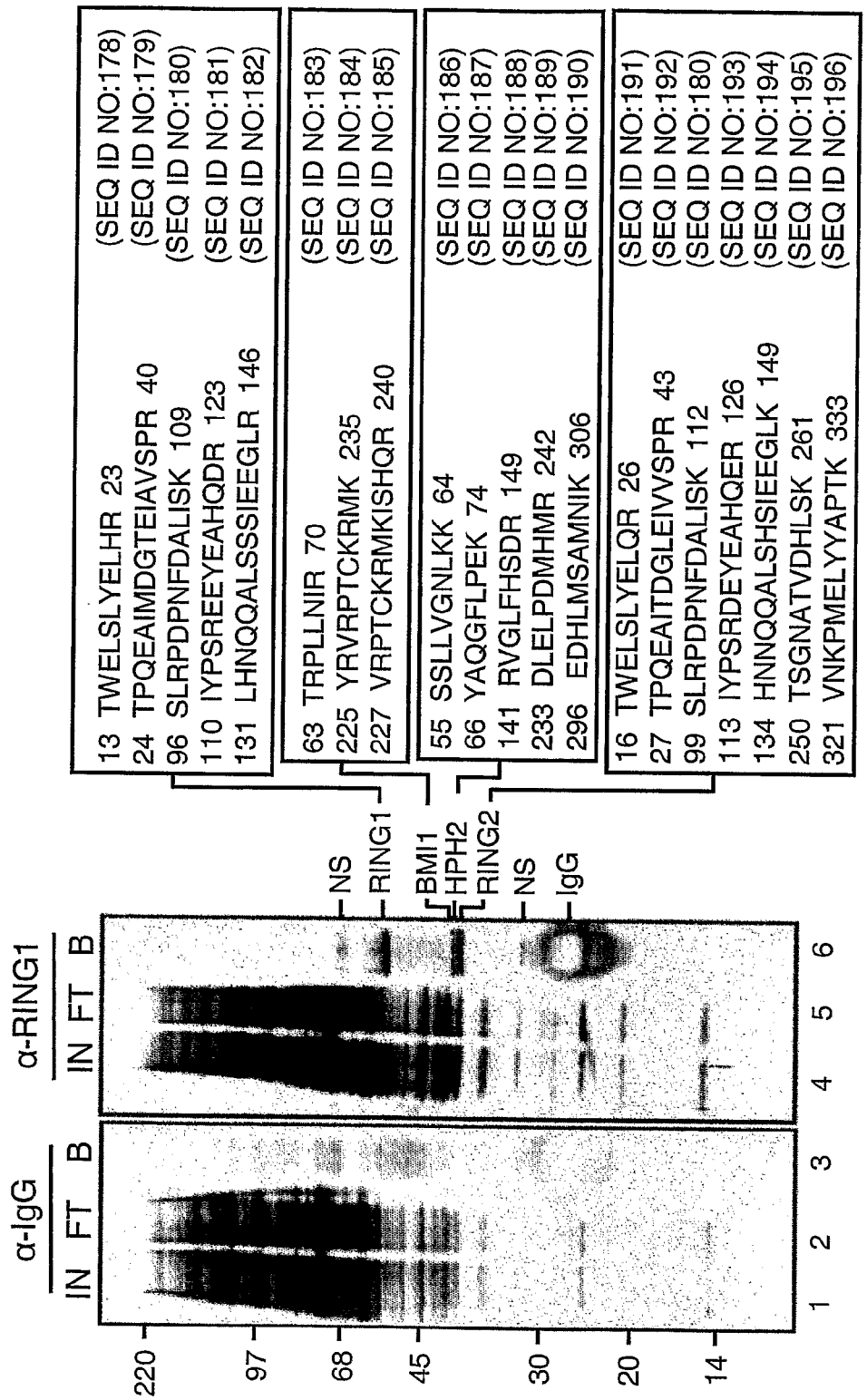
Figure 2E:
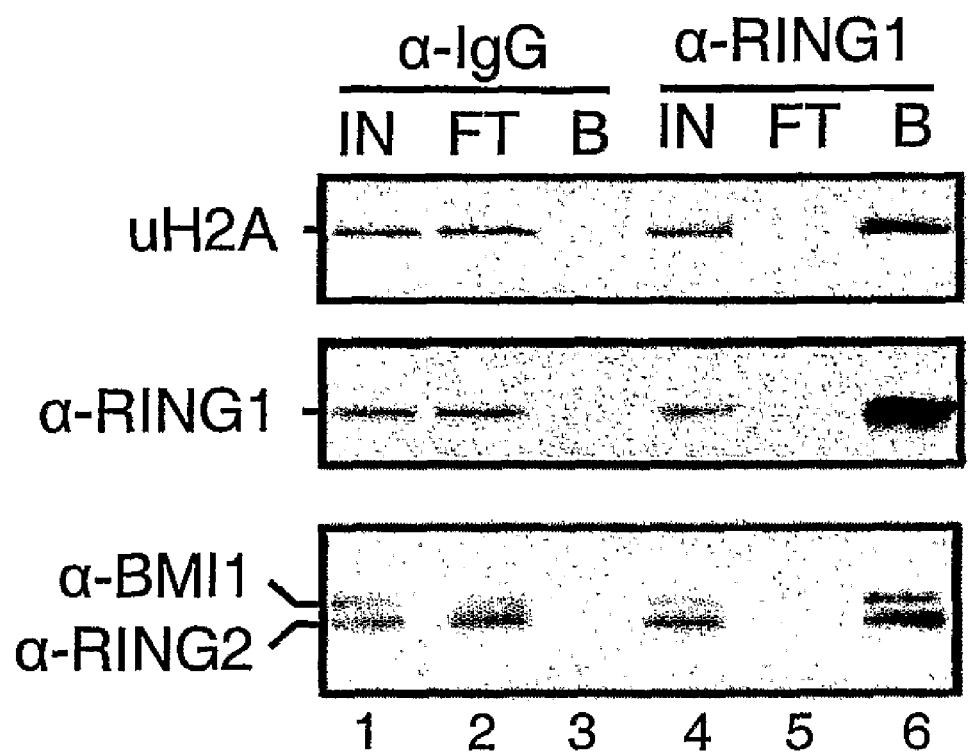

Results. Silver stain analysis revealed that anti-Ring1 antibodies specifically immunoprecipitated four protein bands (FIG. 2D, compare lanes 6 to 3). Mass spectrometry analysis identified these proteins as Ring1, Bmi1, HPH2 (human Polyhomeotic 2), and Ring2 (FIG. 2D). The identities of these proteins were also verified by western blot analysis (FIG. 2E, bottom two panels). The protein complex was apparently responsible for the ligase activity as the activity was depleted in the flow-through (FIG. 2E, top panel, compare lanes 5 and 2). Collectively, these results indicated that the H2A ubiquitin E3 ligase complex was composed of four PcG proteins including Ring1, Bmi1, HPH2, and Ring2. Given that a human Polycomb repressive complex containing Ring1, Ring2, Bmi1, HPH1, HPH2, HPH3, M33, SNF2H, SCMH1, HSP70, and tubulin has been previously purified from HeLa cell lines expressing FLAG®-tagged Bmi1 or M33 and named hPRC1 (Levine, et al. (2002) *Mol. Cell Biol.* 22:6070-8), the instant complex was named hPRC1L (human PRC1-like).

EXAMPLE 4

Identification of the Catalytic Subunit

Constructs and Antibodies. Plasmids encoding GST-Ring2 and GST-Ring2 (His69Tyr) have been described (Lee, et al. (2001) *FEBS Lett.* 503:61-4). The GST-Ring2 (Arg70Cys) mutant was generated by PCR-based mutagenesis and confirmed by DNA sequence analysis. Plasmids encoding GST-Ring1 and GST-Bim1 were constructed by PCR amplification of EST clones (CS0DI076YE14 and CL0BB004ZD04) and the inserts cloned into EcoRI and XhoI sites of pGEX-KG vector. A plasmid encoding $His_6$-dRing was constructed by RT-PCR amplification of the RNA from *Drosophila* embryos and the full-length coding sequence inserted into the pQE30 vector. The $His_6$-dRing (Arg65Cys) mutant was generated by replacing a PstI fragment of wild-type dRing with a corresponding fragment from the mutant $Sce^{33M2}$ allele. All the sequences were verified by DNA sequence analysis. Plasmid for $His_6$-Ubc5c was a gift from Y. Xiong. Antibodies against uH2A and Bmi1 were purchased from UPSTATE® (Waltham, Mass.). Antibodies against PC, H3-3mK27, Ring1 and Ring2 have been previously described (Cao, et al. (2002) *Science* 298:1039-43; Plath, et al. (2003) *Science* 300:131-5; Schoorlemmer, et al. (1997) *EMBO J.* 16:5930-42). Antibody against dRing was generated in rabbits by injection of a $His_6$-dRing fusion protein.

Figure 3B:
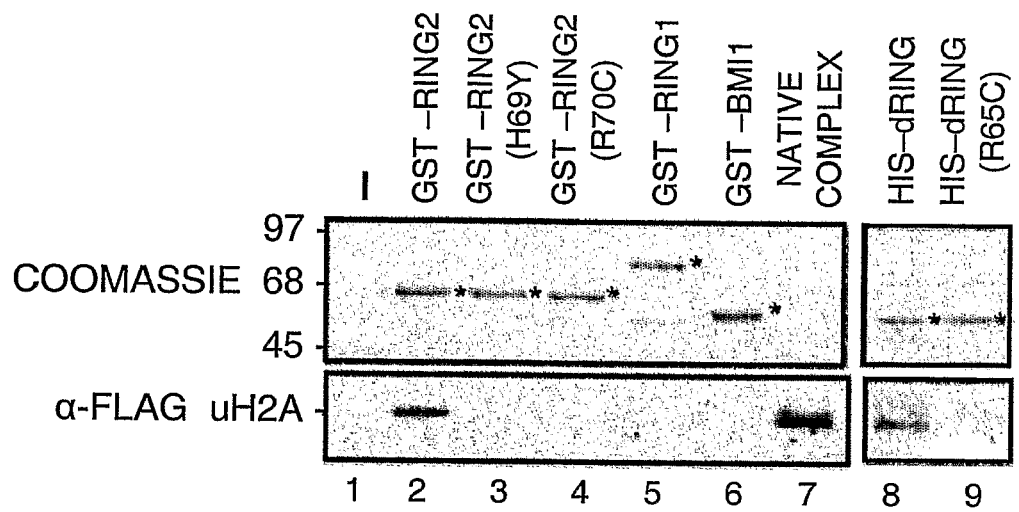

Results. Ring finger has been identified as a signature motif for ubiquitin E3 ligase (Joazeiro & Weissman (2000) *Cell* 102:549-52). Of the four PcG proteins in the H2A ubiquitin E3 ligase complex, three contain ring fingers (FIG. 3A). To determine the catalytic subunit of the E3 ligase complex, each of the ring-containing proteins was expressed as a GST fusion protein (FIG. 3B) and their potential ubiquitin ligase activity analyzed using equal amounts of oligonucleosomal substrates. Results shown in FIG. 3B indicate that only recombinant Ring2 was active (bottom panel, compare lanes 2, 5, and 6). To determine whether the ring finger domain of Ring2 was responsible for the enzymatic activity, a conserved His residue involved in zinc binding was mutated to Tyr (His69Tyr). This change completely abrogated the E3 ligase activity (FIG. 3B, compare lanes 2 and 3), indicating that the ring finger domain of Ring2 was critical for its ubiquitin ligase activity. Previous studies in *Drosophila* have identified a loss of function dRing/Sce allele, $Sce^{33M2}$, that contains a single amino acid substitution (Arg65Cys) in the ring finger domain (Fritsch, et al. (2003) *Mech. Dev.* 120:949-54). To analyze the effect of this mutation on the E3 ligase activity, a Ring2 mutant (Arg70Cys) that mimics the $Sce^{33M2}$ mutation was generated (FIG. 3A). This mutation also abrogated the Ring2 enzymatic activity (FIG. 3B, compare lanes 2 and 4), indicating that the phenotypes associated with $Sce^{33M2}$ may be linked to defective H2A ubiquitination. To verify this possibility, wild-type and a mutant dRing (Arg65Cys) that has the same mutation as that of the $Sce^{33M2}$ allele were made and tested for E3 activity. Results shown in FIG. 3B (lanes 8 and 9) demonstrate that wild-type dRing, but not the mutant, had H2A ubiquitin ligase activity. Therefore, both Ring2 and dRing contain intrinsic E3 ligase activity and the conserved Arg70 (Arg65 in dRing) in the ring domain is critical for the enzymatic activity.

EXAMPLE 5

Ring2 Activity In Vivo

Methodology. To access the role of Ring2 in H2A ubiquitination in vivo, two independent, stable Ring2 knock-down cell lines, KD1 and KD2, were generated. Two different regions of human Ring2 mRNA were targeted for degradation using a vector-based siRNA approach (Wang, et al. (2003) *Mol. Cell* 12:475-87). Briefly, vectors expressing the following hairpin RNAs were transfected into HeLa cells by EFFECTENE™ (INVITROGEN™, Carlsbad, Calif.). Transfected cells were selected in the presence of 2 μg/mL puromycin. Selected clones were amplified and the efficiency of Ring2 knock-down as well as its effect on H2A ubiquitination were analyzed. Total cell lysates used for Ring2 western blot analysis were prepared according to established methods (Wang, et al. (2003) *Mol. Cell* 12:475-87). To prepare samples for evaluation of H2A ubiquitination, cells from a 100-mm plate were collected, washed twice with cold phosphate-buffered saline (PBS), suspended in 200 μL PBS and adjusted to 0.2 N HCl by the addition of 2 N HCl. The suspension was kept on ice for 30 minutes and centrifuged for 10 minutes at 13,000 rpm. The supernatant was mixed with 200 μL 25% trichloroacetic acid (TCA) and kept on ice for another 30 minutes. The precipitated proteins were collected and washed with acetone. Proteins were then dissolved in SDS loading buffer and analyzed by western blot. The two siRNAs targeted to Ring2 mRNA were: 5'-AGAACACCATGACTACAAATT CAA GAG A TTTGTAGTCATGGTGTTCT-3' (SEQ ID NO:3) and 5'-GGCTAGAGCTTGATAATAATT CAA GAG A TTATTATCAAGCTCTAGCC-3' (SEQ ID NO:4). Knock-down cell line 1 (KD1) was established from the first siRNA targeting amino acid 58-65, while knock-down cell line 2 (KD2) was established from the second siRNA targeting amino acid 204-210. The effect of Ring2 knock-down on cell growth was analyzed in accordance with standard methods (Cao & Zhang (2004) *Mol. Cell* 15:57-67).

Figure 3C:
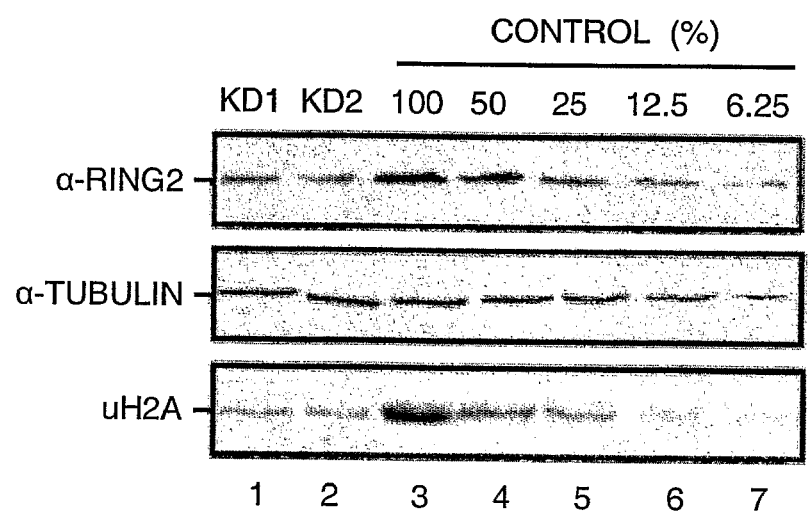
Figure 3D:
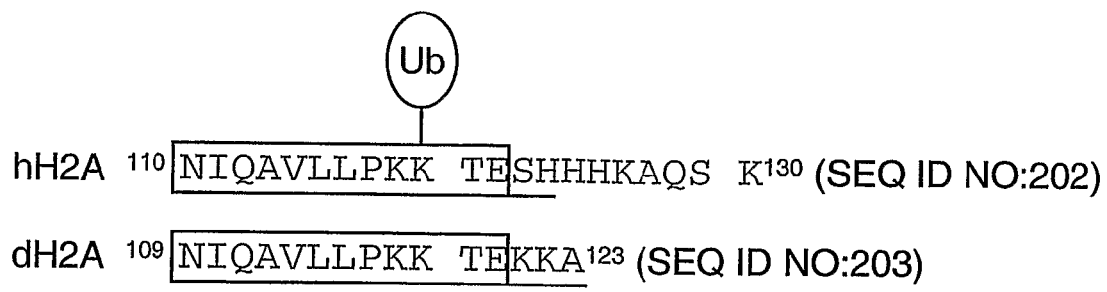
Figure 3E:
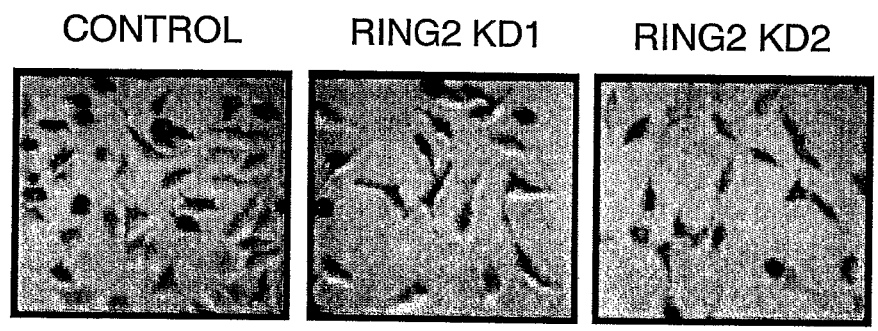
Figure 3E:
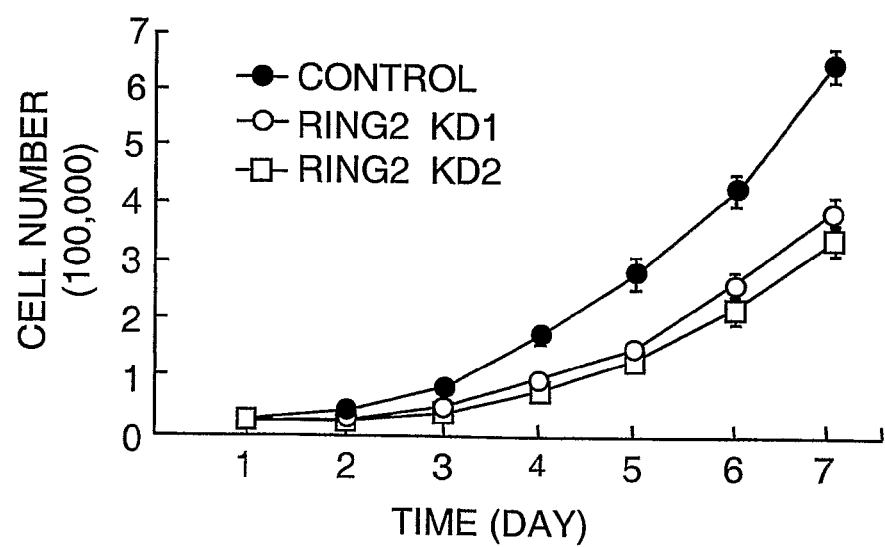

Results. Western blot analysis indicated that about 75% knock-down was achieved at the protein level in both cell lines (FIG. 3C, top panel, compare lanes 1 and 2 with 5). To evaluate the effect of Ring2 knock-down on H2A ubiquitination in vivo, western blot analysis was performed using a previously well-characterized uH2A-specific monoclonal antibody, E6C5 (Vassilev, et al. (1995) *J. Cell Sci.* 108(Pt 3):1205-15), which can also recognize ubiquitinated H2A from *Drosophila* (FIG. 3D). Results shown in FIG. 3C indicated a roughly 75% decrease in the uH2A level in the knock-down cells when compared with that of control knock-down cells (bottom panel, compare lanes 1 and 2 with 5). These data indicate that Ring2 is required for H2A ubiquitination in vivo. Similar to knock-down of SUZ12 (Cao & Zhang (2004) *Mol. Cell* 15:57-67), an EED-EZH2 HMTase component, Ring2 knock-down resulted in changes in cellular morphology and slower growth (FIG. 3E), consistent with a role of Ring2 in regulating cellular differentiation and proliferation Voncken, et al. (2003) *Proc. Natl. Acad. Sci. USA* 100:2468-73).

EXAMPLE 6

Figure 4A:
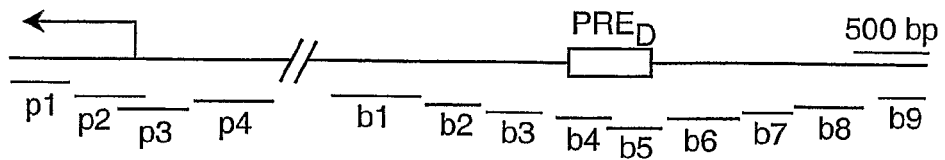
FIGS. 4A-4G show dRing-dependent H2A ubiquitination at Ubx PRE and promoter regions.

Characterization of Functional Relationship between dRing-Mediated H2A Ubiquitination and Hox Gene Silencing Methodology. To determine the functional relationship between dRing-mediated H2A ubiquitination and Hox gene silencing, analysis of the well-characterized *Drosophila* PcG target gene, Ubx, was conducted. Culture of SL2 cells and transfection with double-stranded RNA, chromatin immunoprecipitation (ChIP) assays, and RT-PCR analysis of Ubx transcripts from SL2 cells were performed according to standard methods (Wang, et al. (2004) *Mol. Cell* 14:637-46), with the exception that ChIP assays were performed on cells harvested 72 hours following a single transfection with double-stranded RNA. dRing double-stranded RNA including exonic sequences extending from 167 to 1154 bp downstream of the ATG (FIG. 4A) was synthesized by bi-directional transcription of RT-PCR products containing T7 promoter sequences at both ends. Isolation of wing imaginal discs and ChIP assays were performed using established methods (Wang, et al. (2004) *Mol. Cell* 14:637-46).

Figure 4B:
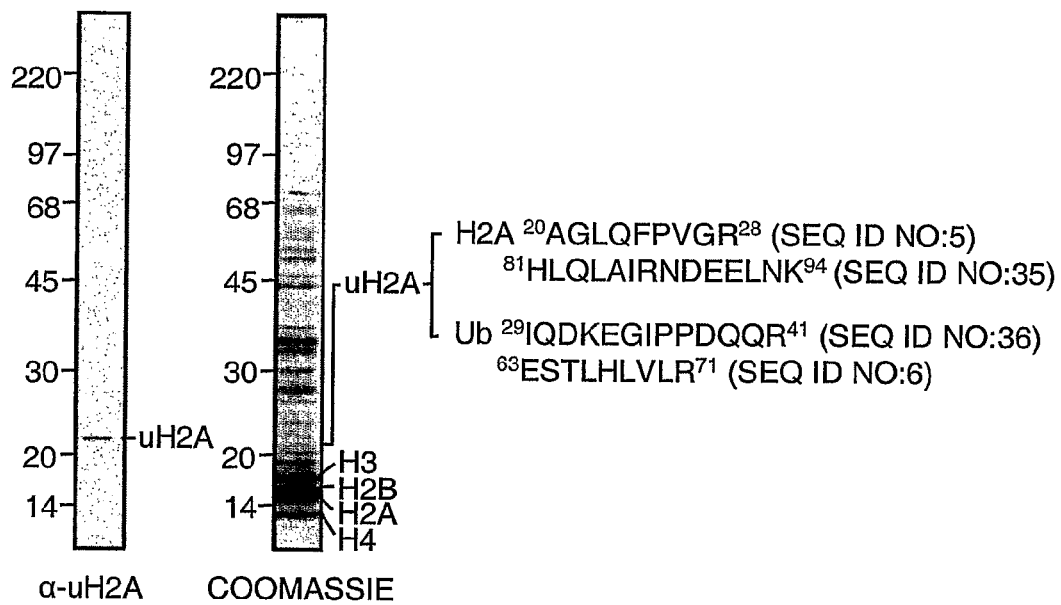

Ubiquitinated histone from SL2 cells was extracted according to established methods with minor modifications (Levinger & Varshavsky (1982) *Cell* 28:375-85). Briefly, 50 mL of SL2 cells ($6-8 \times 10^6$ cells/mL) was collected and lysed in 5 mL buffer A [0.25 M sucrose, 10 mM sodium HEPES (pH 7.5), 3 mM $CaCl_2$, 10 mM NaCl, 1 mM PMSF, 1 mM DTT, 0.25% NONIDET™ 40] on ice for 30 minutes. The lysate was then centrifuged at 3000 rpm for 10 minutes to pellet the nuclei. The nuclei were then washed with buffer A one more time before being suspended in 800 μL buffer B [0.25 M sucrose, 10 mM sodium HEPES (pH 7.5), 3 mM $CaCl_2$, 10 mM NaCl, 1 mM PMSF, 1 mM DTT]. HCl (2 N) was then added to a final concentration of 0.2 N. The suspension was extracted at 4° C. overnight and was then centrifuged for 10 minutes at 13,000 rpm. The supernatant was mixed with equal volume of 50% TCA and kept on ice for 1 hour. The precipitated proteins were collected and washed with acetone. Proteins were then dissolved in SDS loading buffer and analyzed by western blot (FIG. 4B).

Figure 4C:
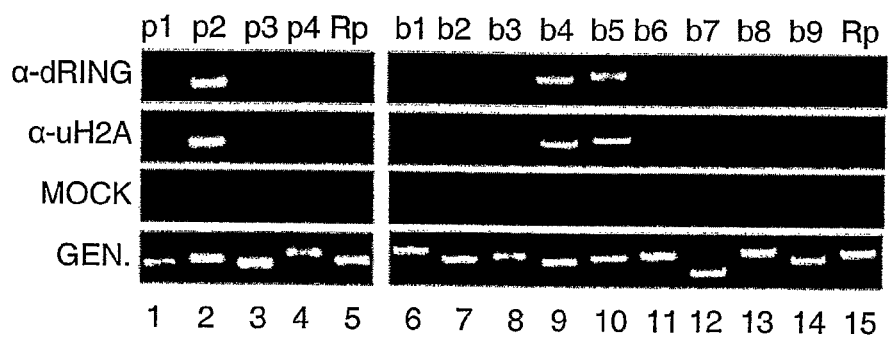
Figures 4D, 4E:
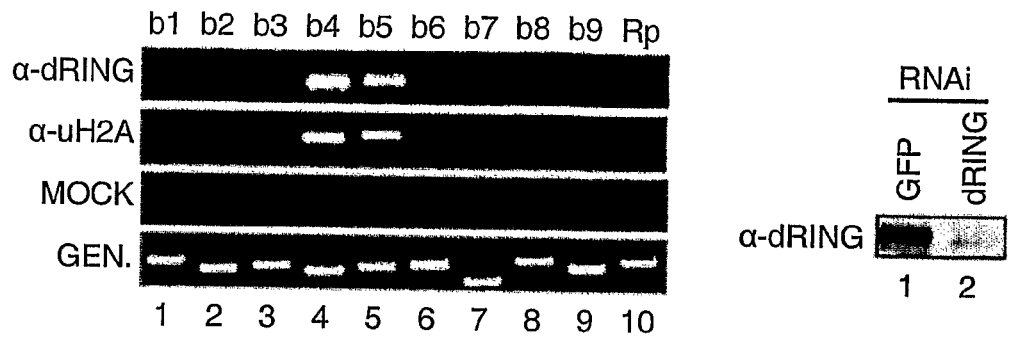
Figure 4F:
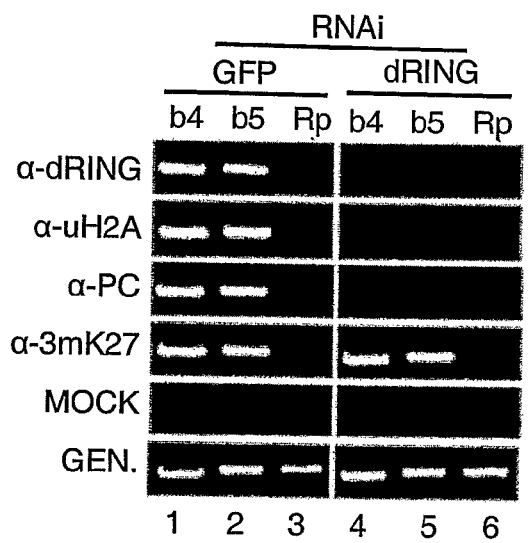
Figure 4G:
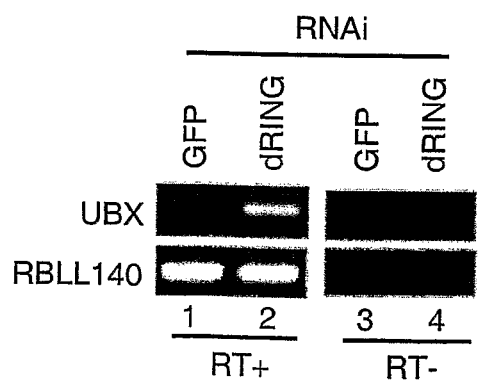

Results. Silencing of Ubx transcription in wing imaginal discs requires both the ESC-E(Z) and PRC1 complexes, in addition to the major PRE (Polycomb response element) within the bxd regulatory region ($PRE_D$) to which the two complexes bind. Having demonstrated the specificity of the E6C5 monoclonal anti-uH2A antibody for *Drosophila* uH2A (FIG. 3D), ChIP assays of wing imaginal discs cells were performed which revealed co-localization of dRing and ubiquitinated H2A at $PRE_D$ and immediately downstream of the Ubx transcription start site (FIG. 4C), sites at which E(Z) and PC, another PRC1 core component, previously have been shown to be located (Cao, et al. (2002) *Science* 298:1039-43; Wang, et al. (2004) *Mol. Cell* 14:637-46). Homozygous Sce/dRing mutants die early in development, precluding ChIP analysis of mutant wing imaginal discs (Fritsch, et al. (2003) *Mech. Dev.* 120:949-54). Therefore, dependence of H2A ubiquitination at $PRE_D$ on dRing was tested using SL2 tissue culture cells. Previous studies have shown that PC, E(Z) and E(Z)-dependent H3-K27 methylation co-localize at the $PRE_D$ region in SL2 cells (Cao, et al. (2002) *Science* 298:1039-43; Wang, et al. (2004) *Mol. Cell* 14:637-46). As in wing imaginal discs, dRing and ubiquitinated H2A also co-localized at $PRE_D$ (FIG. 4D). Depletion of dRing by RNAi (FIG. 4E) resulted in a loss of ubiquitinated H2A, as well as PC from the PRE (FIG. 4F, right panels). E(Z)-dependent trimethylation on H3-K27 was not affected (FIG. 4F, right panels). Loss of dRing, PC and uH2A was accompanied by derepression of Ubx gene expression (FIG. 4G) similar to that previously observed upon RNAi-mediated depletion of PC (Wang, et al. (2004) *Mol. Cell* 14:637-46). Because the PRC1 complex appears to be lost along with dRing, the roles of H2A ubiquitination and other potential functions of the PRC1 complex in Ubx repression could not be distinguished. However, somatic clones that are homozygous for the $Sce^{33M2}$ allele, which contain the Arg65Cys substitution within the ring domain, exhibit Ubx derepression in wing imaginal discs (Fritsch, et al. (2003) *Mech. Dev.* 120:949-54). Together with the fact that the Arg65Cys mutation abolishes dRing ubiquitin ligase activity, (FIG. 3B), these observations collectively indicate that dRing-mediated H2A ubiquitination plays an important role in Ubx gene silencing.

EXAMPLE 7

Figure 5A:
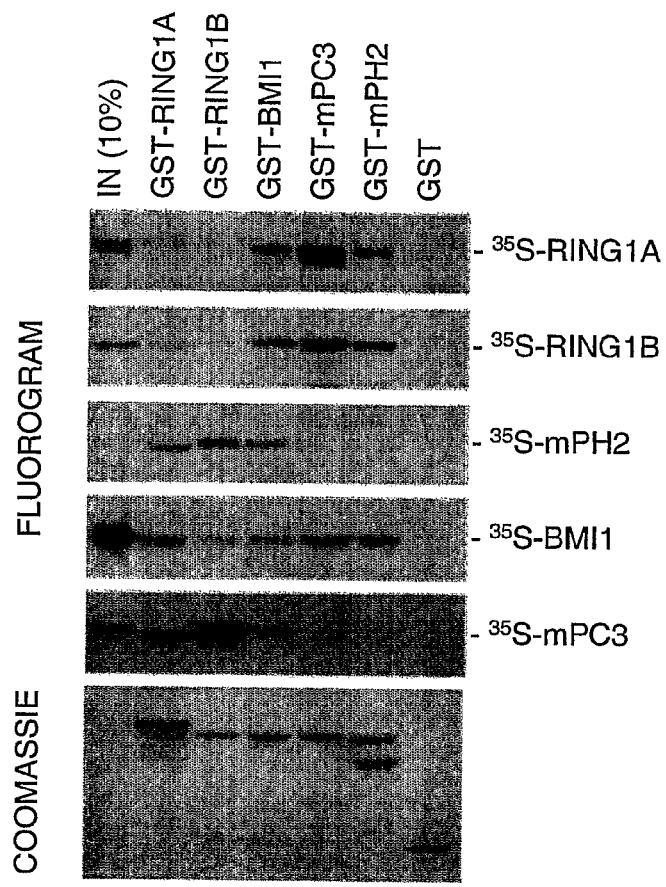
FIGS. 5A-5B show protein-protein interactions among components of the PRC1 complex.
Figure 5B:
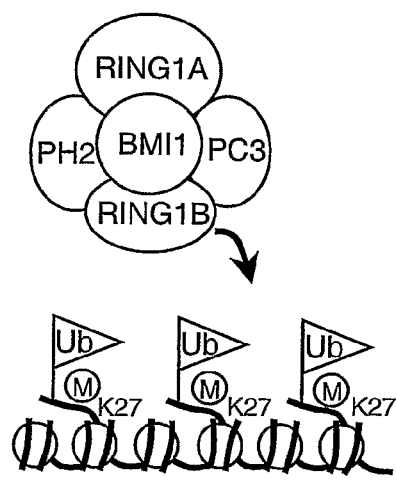

Protein-Protein Interactions in the PRC1 Complex, Reconstitution of the Complex and Characterization of Individual Components Studies were carried out to evaluate protein-protein interactions among components of the PRC1 complex. FIG. 5A shows the results of GST pull-down assays using equal amounts of GST-fusion proteins and in vitro translated $S^{35}$-labeled proteins indicated on right. "In" represents 10% of the total Input. FIG. 5B is a schematic representation of the interactions detected in FIG. 5A. Bmi1 is the core component to bring others together to form the complex. This study demonstrates that Ring1A (i.e., Ring1) and Ring1B (i.e., Ring2) do not interact each other, but can form a complex through association with Bmi1.

Figure 6A:
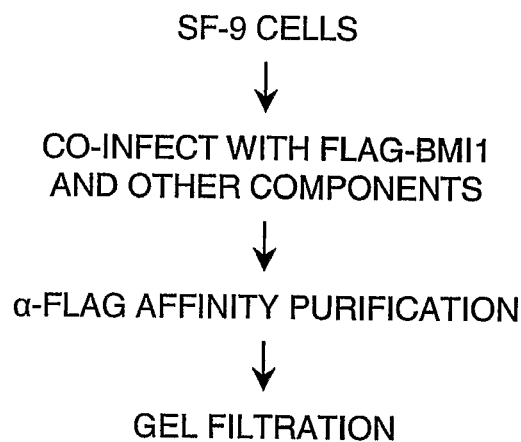
FIGS. 6A-6B show reconstitution of the four-component PRC1 complex.
Figure 6B:
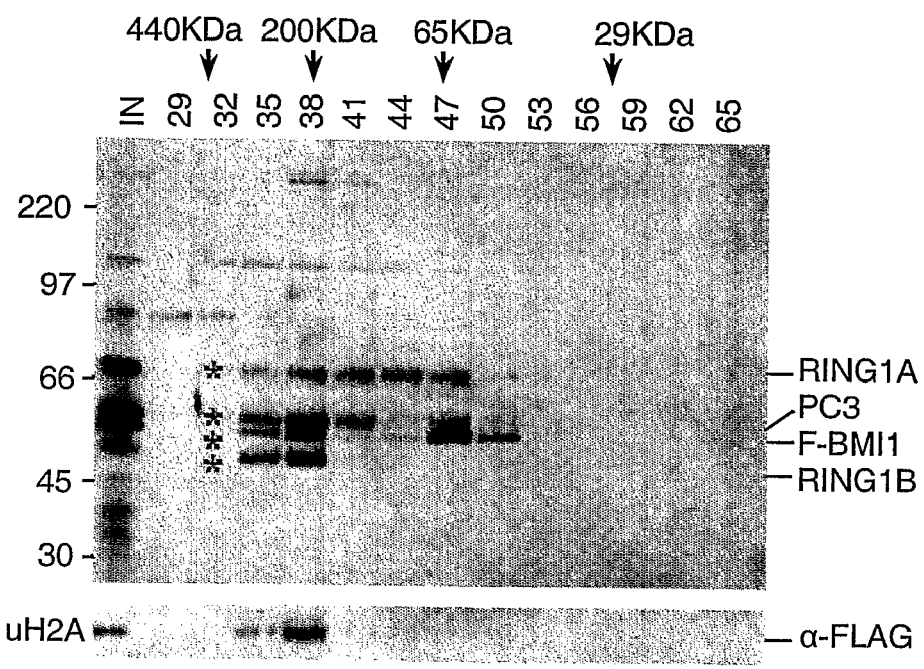

Experiments were performed to reconstitute the four-component PRC1 complex. FIG. 6A is a schematic representation of the steps involved in PRC1 reconstitution. FIG. 6B shows silver staining of a polyacrylamide-SDS gel (top panel), and ubiquitin ligase activity assay (bottom panel) of the fractions derived from the S6 gel-filtration column. The positions of the protein size markers are indicated to the left of the panel. The four components of the recombinant PRC1 complex are indicated by "*". Consistent with the interaction study, the four components can form a stable and very active complex.

Figure 7A:
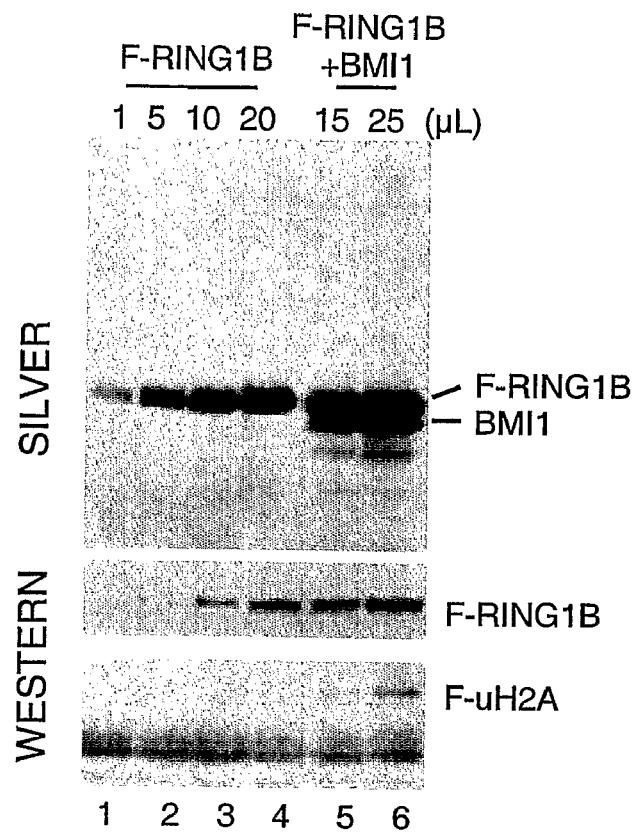
FIG. 7A, Bmi1 can stimulate the ubiquitin ligase activity in vitro. Silver staining of a polyacrylamide-SDS gel of Flag-Ring1B alone (lane 1-3) and F-Ring1B/Bmi1 sub-complex (lane 4-5) in top panel. The amount of F-Ring1B has been further verified by western blot using anti-Flag antibody (middle panel).

Studies were also performed to characterize the individual components in the PRC1 complex. Bmi1 can stimulate the ubiquitin ligase activity in vitro. FIG. 7A shows silver staining of a polyacrylamide-SDS gel of Flag-Ring1B alone (lane 1-3) and F-Ring1B/Bmi1 sub-complex (lane 4-5) in top panel. The amount of F-Ring1B has been further verified by western blot using anti-Flag antibody (middle panel). The data in FIG. 7B demonstrates that Ring1A can also stimulate the ubiquitin ligase activity in vitro. The 2-component complex of F-Ring1B/Bmi1 (lane 1-4) has been compared to 3-component complex of Ring1B/F-Bmi1/Ring1A (lane 5-6). The amount of Ring1B has been verified by western blot using anti-Ring1B antibody (top panel). The ubiquitinated H2A was detected by western blot with an anti-Flag antibody (bottom panel).

Bmi1 and Ring1A are both important for H2A ubiquitination in vivo, and knock-out of individual components results in derepression of several Hox genes. FIG. 8A shows Western blot analysis of ubiquitinated H2A extracted from wild-type and Ring1A knock-out MEF cells with an antibody specific for ubiquitinated H2A. Equal loading was confirmed by western blot using anti-H3 and anti-tubulin antibodies. FIG. 8B shows Western blot analysis of ubiquitinated H2A extracted from wild-type and Bmi1 knock-out MEF cells with antibody specific for ubiquitinated H2A. Equal loading was confirmed by western blot using anti-H3 and anti-tubulin antibodies. FIG. 8C shows RT-PCR analysis of Hox genes expression in Ring1A knock-out and wild-type MEF cells. GAPDH was used as a control. For each gene, "−RT" serves as control to exclude the genomic DNA amplification. HoxA7 shows no change, while C12, A13 and Meis1 show increased expression in Ring1A −/− cells.

EXAMPLE 8

Role of Bmi-1 and Ring1A in H2A Ubiquitylation and Hox Gene Silencing Experimental Procedures Purification of Recombinant PRC1 Complex and Subcomplexes Ring1B cDNA was PCR-amplified from I.M.A.G.E cDNA clone (4021046) and inserted into BamHI and HindIII sites of a pFASTBAC (GIBCO-BRL) vector with or without a N-terminal FLAG®-tag. Pc3 cDNA was amplified from I.M.A.G.E cDNA clone (4456896) and inserted into HindIII and NcoI sites of pFASTBAC (GIBCO-BRL) without FLAG®. Ph2 cDNA was amplified from I.M.A.G.E cDNA clone (6410302) and inserted into BamHI and HindIII sites of pFASTBAC (GIBCO-BRL) without FLAG®. All the sequences have been verified by DNA sequencing. Baculovirus expression vectors for Bmi-1, Mel-18, and Ring1A were provided by Dr. Kingston and were previously described (Lavigne et al. (2004) *Mol Cell* 13:415-425). All the baculoviruses were generated and amplified following the manufacturer's protocol. To purify the recombinant PRC1 complex and sub-complexes, different baculoviruses were used to co-infect SF9 cells. After two days of infection, cells were collected and resuspended in F lysis buffer [20 mM Tris (pH 7.9), 500 mM NaCl, 4 mM $MgCl_2$, 0.4 mM EDTA, 2 mM DTT, 20% glycerol, 0.1% NP40] with proteinase inhibitors. Then cells were homogenized with pestle A three times (10 strokes each) in a period of 30 minutes. The supernatant was recovered by centrifuging at 11,000 rpm for 10 minutes. The supernatant was adjusted to 300 mM NaCl by adding Dilution buffer [20 mM Tris (pH 7.9), 10% glycerol], then incubated with the M2 α-FLAG® agarose (Sigma, St. Louis, Mo.) equilibrated with F lysis buffer for 4 hours at 4° C. After washing with F washing buffer [20 mM Tris (pH 7.9), 150 mM NaCl, 2 mM $MgCl_2$, 0.2 mM EDTA, 1 mM DTT, 15% glycerol, 0.01% NP40] until no protein came out, bound proteins were eluted with 0.2 mg/ml FLAG® peptide (DYKDDDDK; SEQ ID NO:5) in F washing buffer for 20 minutes each time at room temperature. The eluted complexes were further purified through a gel-filtration SEPHADEX 200 or SUPEROSE 6 column.

Ubiquitin E3 Ligase Assay, Endogenous ubH2A Analysis, and Antibodies

Oligonucleosomes (5 μg) were incubated with 30 μL protein fractions or recombinant proteins in a 40 μL reaction containing 50 mM Tris-HCl (pH 7.9), 5 mM $MgCl_2$, 2 mM NaF, 0.6 mM DTT, 2 mM ATP, 10 μM Okada acid, 0.1 μg ubiquitin activating enzyme E1 (Calbiochem), 0.6 μg ubiquitin conjugating enzyme Ubc5c, 1 μg FLAG®-ubiquitin (Sigma, St. Louis, Mo.). After incubation at 37 C for 1 hour, the reaction was terminated by the addition of SDS-PAGE loading buffer. The proteins were resolved in 8-15% SDS-PAGE and blotted with anti-FLAG® antibody. To evaluate H2A ubiquitylation in vivo, cells were collected from a 100 mm plate, washed with cold PBS twice, and then suspended in 200 μL PBS with 0.2 N HCl. The suspension was kept on ice for 30 minutes and centrifuged for 10 minutes at 13,000 rpm. The extracted supernatant was mixed with 200 μL 25% TCA and kept on ice for another 10 minutes. The precipitated proteins were collected by centrifugation and washed by acetone. After air drying, proteins were dissolved in 1×SDS loading buffer and analyzed by western blotting. Antibodies against uH2A, tubulin and Bmi-1 were purchased from Upstate and Sigma. Antibodies against Ring1A, Ring1B, SUZ12 and trimethyl-H3 K27 have been previously described (Example 4; Cao and Zhang, (2004) *Mol Cell* 15:57-67). Antibodies against H3 were kindly provided by Dr. Verrault.

Plasmids and GST Pull-Down Assay

Full-length cDNAs for Ring1B, Ring1A, Bmi-1, Pc3 and Ph2 were inserted into pCITE vector for in vitro translation using the rabbit reticulocyte lysate kit according to the manufacturer's instructions (PROMEGA, Madison, Wis.). Full-length cDNAs for Ring1B, Ring1A, Bmi-1, Pc3 and Ph2 were also cloned into pGEX-KG vector for the production of GST-fusion proteins. About 3 μg of GST or GST fusion proteins were bound to 10 μL of glutathione-immobilized agarose beads (Sigma) and incubated with in vitro-translated products in 500 μL buffer A (50 mM Tris-HCl [pH 7.9], 0.5 mM EDTA, 1 mM dithiothreitol, 0.2 mM phenylmethylsulfonyl fluoride, 10% glycerol) containing 150 mM KCl and 0.05% NP-40. After incubation at 4° C. for 2 hours, the beads were washed three times with buffer A containing 300 mM KCl and 0.05% NP-40 and then washed once in buffer A containing 50 mM KCl before being subjected to SDS-PAGE and autoradiogram.

Cell Lines and RT-PCR Analysis of Hox Gene Expression

Ring1A −/− and +/+ MEFs were provided by Dr. Vidal and were previously described (del Mar Lorente et al. (2000) *Development* 127:5093-5100). Immortalized Bmi-1−/− and +/+ MEFs were provided by Dr. Lohuizen. Total RNAs were isolated from both −/− and +/+ MEFs using RNEASY® (QIAGEN, Vilencia, Calif.) and treated with RNase-free DNase I (PROMEGA). For each sample, 1 μg RNA was used for a 20 μL reverse transcription reaction using IMPROM-II (PROMEGA). For Hox gene expression analysis, 1 μL cDNA was used as template for PCR. For control, 1/20 μL of cDNA was used for GAPDH amplification. The primer sequences for all the Hox genes and GAPDH are available in Table 1.

ChIP Assay

For ChIP assays, approximately $5\times10^6$ HeLa cells or $2\times10^6$ MEF cells in 150 mm dishes were treated with DMEM containing 1% formaldehyde for 10 minutes at room temperature. The cross-linking was stopped by the addition of 125 mM glycine and incubation for 10 minutes. After washing twice with PBS, the cells were resuspended in 300 μL of cell lysis buffer (10 mM HEPES [pH 7.9], 0.5% NP-40, 1.5 mM $MgCl_2$, 10 mM KCl, 0.5 mM DTT) by pipetting and kept on ice for 10 minutes. After centrifugation at 4,000 rpm for 5 minutes, the cell pellets were resuspended in nuclear lysis buffer (20 mM HEPES [pH 7.9], 25% glycerol, 0.5% NP-40, 0.42 M NaCl, 1.5 mM $MgCl_2$, 0.2 mM EDTA) containing protease inhibitors to extract nuclear proteins at 4° C. for 20 minutes. Then the chromatin was sonicated into fragments with an average length of 0.5-3 kb. After centrifugation at 13,000 rpm for 10 minutes, the supernatants were diluted in equal volume of dilution buffer containing 1% TRITON X-100, 2 mM EDTA, 20 mM Tris-HCl [pH 7.9], 50 mM NaCl, and protease inhibitors. The extracts were pre-cleaned by incubating with 60 μL Protein A-SEPHAROSE beads for at least one hour. ChIP assays were then performed with indicated antibodies as previously described (Cao and Zhang, (2004) *Mol Cell* 15:57-67). ChIP DNA was detected by standard PCR using PLATINUM Taq polymerase (INVITROGEN). The primer pairs covering the mouse HoxC13 genome locus are designed by Array Designer from Premierbiosoft and available in Table 2. The following primer pairs are for the two regions of the human HOXC13: A-TGC AGC GGA GCG AGC CCC (SEQ ID NO:6) and TCA ACA GGG ATG AGC GCG TCG TG (SEQ ID NO:7), B-GGA TTC CGG TCT AGG GAG TC (SEQ ID NO:8) and CAG CCA ATA CAG GGT AGG TGA (SEQ ID NO:9).

TABLE 1

| mHox | Sequence | SEQ ID NO |
|---|---|---|
| mHoxA1 | F-ATGAACTCCTTTCTGGAATA | SEQ ID NO: 10 |
| | R-CGTACTCTCCAACTTTCC | SEQ ID NO: 11 |
| mHoxA2 | F-AGAACTGTGGAGCTGGCCTA | SEQ ID NO: 12 |
| | R-GGTCGATTGTGGTGAGTGTG | SEQ ID NO: 13 |
| mHoxA3 | F-ATGCCAGTCAGCAGCCATA | SEQ ID NO: 14 |
| | R-TGTACTTCATGCGGCGGT | SEQ ID NO: 15 |
| mHoxA4 | F-TCCAGTTATAACGGAGGCGAAC | SEQ ID NO: 16 |
| | R-GAATGGGTGTGGAAGCACCAG | SEQ ID NO: 17 |
| mHoxA5 | F-CGCAAGCTGCACATTAGTCAC | SEQ ID NO: 18 |
| | R-GCCATACTCATGCTTTTCAGC | SEQ ID NO: 19 |
| mHoxA6 | F-CTGATAAAGACCTCAGTG | SEQ ID NO: 20 |
| | R-TCAGGTAGCGGTTGAAGTG | SEQ ID NO: 21 |
| mHoxA7 | F-CTCTGCAGTGACCTCGCCAAAG | SEQ ID NO: 22 |
| | R-CTTGTCAGCAGCTGTGGATTC | SEQ ID NO: 23 |
| mHoxA9 | F-ACGGCAGGTATATGCGCT | SEQ ID NO: 24 |
| | R-GAACCAGATCTTGACCTGC | SEQ ID NO: 25 |
| mHoxA10 | F-GTGAGTTCTGGGGCAGAGGC | SEQ ID NO: 26 |
| | R-AGTTCCAAAGGCGAAAATGC | SEQ ID NO: 27 |
| mHoxA11 | F-CATATCCCTACTCCTCAACCTGC | SEQ ID NO: 28 |
| | R-CCCACCGTGCTATAGAAATTGG | SEQ ID NO: 29 |
| mHoxA13 | F-CCGACAAGTACATGGACAC | SEQ ID NO: 30 |
| | R-TATAGGAGCTGGCGTCTGA | SEQ ID NO: 31 |
| mHoxB1 | F-CCTTTTTAGAGTACCCACTTTG | SEQ ID NO: 32 |
| | R-GCATCTCCAGCGGCTTCCTT | SEQ ID NO: 33 |
| mHoxB2 | F-CGGCGCCTCCACCCTTCAGAGACC | SEQ ID NO: 34 |
| | R-CTTTCGGTGAGGTCCAGCAAGGC | SEQ ID NO: 35 |
| mHoxB3 | F-CCGCACCTACCAGTACCACT | SEQ ID NO: 36 |
| | R-GGAGCTGTTTTCAGCTTGG | SEQ ID NO: 37 |
| mHoxB4 | F-TTCACGTGAGCACGGTAAAC | SEQ ID NO: 38 |
| | R-GTTGGGCAACTTGTGGTCTT | SEQ ID NO: 39 |
| mHoxB5 | F-GCTCTTACGGCTACAATTACAATG | SEQ ID NO: 40 |
| | R-GCTGTAGCCAGACTCATACT | SEQ ID NO: 41 |
| mHoxB6 | F-CGTCCTCCTATTACCCACCA | SEQ ID NO: 42 |
| | R-CACTTCTGCTCCTCGGTCTC | SEQ ID NO: 43 |

TABLE 1-continued

| mHox | Sequence | SEQ ID NO |
|---|---|---|
| mHoxB7 | F-AACCGAGTTCCTTCAACATG | SEQ ID NO: 44 |
| | R-CGAGTCAGGTAGCGATTGTA | SEQ ID NO: 45 |
| mHoxB8 | F-TTCTACGGCTACGACCCTCT | SEQ ID NO: 46 |
| | R-CGTGCGATACCTCGATCCTC | SEQ ID NO: 47 |
| mHoxB9 | F-CGATCATAAGTCACGAGAGCG | SEQ ID NO: 48 |
| | R-TCCTTCTCTAGCTCCAGCGT | SEQ ID NO: 49 |
| mHoxC4 | F-CGATCATAAGTCACGAGAGCG | SEQ ID NO: 50 |
| | R-TCCTTCTCTAGCTCCAGCGT | SEQ ID NO: 51 |
| mHoxC5 | F-TGGATGACCAAACTGCACATGAGC | SEQ ID NO: 52 |
| | R-CAAGTTGTTGGCAATCTCTATGCG | SEQ ID NO: 53 |
| mHoxC6 | F-ACCTTAGGACATAACACACAGA | SEQ ID NO: 54 |
| | R-ACTTCATGCGGCGGTTCTGGAA | SEQ ID NO: 55 |
| mHoxC8 | F-CCACGTCCAAGACTTCTTCCACCACGGC | SEQ ID NO: 56 |
| | R-CACTTCATCCTTGATTCTGGAACC | SEQ ID NO: 57 |
| mHoxC9 | F-ACGTGGACTCGCTCATCTCT | SEQ ID NO: 58 |
| | R-GCCGTAAGGGTGATAGACCA | SEQ ID NO: 59 |
| mHoxC10 | F-TGTTGGCAGGCCTCTGTCCT | SEQ ID NO: 60 |
| | R-CTCCAATTCCAGCGTCTGGTGT | SEQ ID NO: 61 |
| mHoxC11 | F-CTTCGACAACGCCTACTGCG | SEQ ID NO: 62 |
| | R-GTCTGTCAGGTTCAGCATCC | SEQ ID NO: 63 |
| mHoxC12 | F-TGCGCTCGGCTTCAAGTACG | SEQ ID NO: 64 |
| | R-TGGCGTGTGATGAACTCGTTGAC | SEQ ID NO: 65 |
| mHoxC13 | F-TGTCGCACAACGTGAACCTG | SEQ ID NO: 66 |
| | R-CTTCAGGTGCACCTTGGTATAG | SEQ ID NO: 67 |
| mHoxD1 | F-CACAGCACTTTCGAGTGGAT | SEQ ID NO: 68 |
| | R-TGGGTGTCATTCAGCTGTAA | SEQ ID NO: 69 |
| mHoxD3 | F-CAGATCTTCCCCTGGATGAA | SEQ ID NO: 70 |
| | R-TACTTCATGCGACGGTTCTG | SEQ ID NO: 71 |
| mHoxD4 | F-CGATGAGGGAACTCATTGCT | SEQ ID NO: 72 |
| | R-TGCCCTCCTTACTCACCATC | SEQ ID NO: 73 |
| mHoxD8 | F-GGATACGATAACTTACAGAGAC | SEQ ID NO: 74 |
| | R-TAGGGTTTGGAAGCGACTGT | SEQ ID NO: 75 |
| mHoxD9 | F-CACTACGGGATTAAGCCTGAAACC | SEQ ID NO: 76 |
| | R-TTTGGGTCAAGTTGCTGCTG | SEQ ID NO: 77 |
| mHoxD10 | F-CCTATGGAATGCAAACCTGTGG | SEQ ID NO: 78 |
| | R-ATATCCAGGGACAGGAACCTCG | SEQ ID NO: 79 |
| mHoxD11 | F-CTTTGATCAGTTCTACGAG | SEQ ID NO: 80 |
| | R-CAGACGGTCCCTGTTCAGT | SEQ ID NO: 81 |
| mHoxD12 | F-ACCAGGTCAAGTTCTATACG | SEQ ID NO: 82 |
| | R-CAATCTGCTGCTTTGTGTAG | SEQ ID NO: 83 |
| mHoxD13 | F-AGAAGTACATGGACGTGTCG | SEQ ID NO: 84 |
| | R-GTTACTTGTCTCTCCGAAAG | SEQ ID NO: 85 |

TABLE 2

| No | Sequence | SEQ ID NO |
|---|---|---|
| 1 | F-TTATTACAGTAGGTGAGGAGTTGAAC | SEQ ID NO: 86 |
| | R-TTTTCTTCTAGCTCCTTCCCCATAC | SEQ ID NO: 87 |
| 2 | F-CCATTAAAGAAGGGAGTTTGCTTGAC | SEQ ID NO: 88 |
| | R-TGATGTGGGAACTTGAGTTTGGTG | SEQ ID NO: 89 |

TABLE 2-continued

| No | Sequence | SEQ ID NO |
|---|---|---|
| 3 | F-TATACATTGATTTGGAAGAAAGTTGC<br>R-CAAGTTAGACAAGAGGACTGAGG | SEQ ID NO: 90<br>SEQ ID NO: 91 |
| 4 | F-ACTTGGACTTCCCTCTCAGACAG<br>R-GCAGTACAAGTGTAGGCTATCTCC | SEQ ID NO: 92<br>SEQ ID NO: 93 |
| 5 | F-CCAGTCCTAGTTAGGCAACAGAGAG<br>R-TGCTTTTGAGACAGGAGACCCATAC | SEQ ID NO: 94<br>SEQ ID NO: 95 |
| 6 | F-ACAGGATACCCOTTTCTGACCC<br>R-AAGTCACAGCATTTGTAGCAGGAG | SEQ ID NO: 96<br>SEQ ID NO: 97 |
| 7 | F-CCATACCACCCTAGCTCAGAAAG<br>R-CGGGGAAACCCAGCAGAGTC | SEQ ID NO: 98<br>SEQ ID NO: 99 |
| 8 | F-TTCCTTCAGTTCAGTTAAATGATTCC<br>R-CGGGCGATGGTCACACTC | SEQ ID NO: 100<br>SEQ ID NO: 101 |
| 9 | F-CCTACATCTTCATCTGGTCCTTTGC<br>R-GGCTGGCTGAGAGGGTTGG | SEQ ID NO: 102<br>SEQ ID NO: 103 |
| 10 | F-GGCCAAGTTCACCGGACCC<br>R-GTGCTGATGTTCACACAGACTCTC | SEQ ID NO: 104<br>SEQ ID NO: 105 |
| 11 | F-AGAGAGACACCGCAGCCC<br>R-GATTCTGACTGAGCAAAAGGAAAGG | SEQ ID NO: 106<br>SEQ ID NO: 107 |
| 12 | F-GGTATCCCTTTTGTATGCTGAAATGG<br>R-GCTTAATTTGGCCGACGCAAAG | SEQ ID NO: 108<br>SEQ ID NO: 109 |
| 13 | F-CGTTGCCCGTCCCTTTAAATCTCC<br>R-CCGCCGCTGCCGCTCTC | SEQ ID NO: 110<br>SEQ ID NO: 111 |
| 14 | F-TGCAGCGGAGCGAGCCC<br>R-TCAACAGGGATGAGCGCGTCGTG | SEQ ID NO: 112<br>SEQ ID NO: 113 |
| 15 | F-AGTCAGGTGTACTGCTCCAAGG<br>R-AGGTTCTTATACTTCCCCAAATCCC | SEQ ID NO: 114<br>SEQ ID NO: 115 |
| 16 | F-CAGGAGCTGTCAACCACCAGATAC<br>R-TCAGATCAGAGTGGAACCCAAAGC | SEQ ID NO: 116<br>SEQ ID NO: 117 |
| 17 | F-AGCATTGGGTCTACTCTTCCTG<br>R-ATGGAATGCCTACATATGAACAGTC | SEQ ID NO: 118<br>SEQ ID NO: 119 |
| 18 | F-CTTCACTTCTCTAGCTCATAAGACAG<br>R-ACGCCAGCCAGAATCTACTTC | SEQ ID NO: 120<br>SEQ ID NO: 121 |
| 19 | F-TTCTCAGTGCCTGAAGAAGTCC<br>R-CATCTAATTGTCTCCTGGGATTTCTG | SEQ ID NO: 122<br>SEQ ID NO: 123 |
| 20 | F-TTTGGAGCCCGTATATTGACG<br>R-AAAGATTGACTCCACCAAGGTTTC | SEQ ID NO: 124<br>SEQ ID NO: 125 |
| 21 | F-TAGAGCAGATACCTACCTTTTAACC<br>R-TAACTGGTCTTCAATTTGTTTTACTC | SEQ ID NO: 126<br>SEQ ID NO: 127 |
| 22 | F-GTGGCTGGTTTGTTTGTTTGTTTG<br>R-AGGAATTCACAATAGGATGGCACTC | SEQ ID NO: 128<br>SEQ ID NO: 129 |

EXAMPLE 9

The PRC1 Complex is Significantly More Active than Ring1B Alone in H2A Ubiquitylation As described above, a multi-subunit PRC1-like complex from HeLa cells has been purified that possesses H2A-K119 ubiquitin E3 ligase activity. Components of the complex include three ring domain-containing proteins Ring2/Ring1B, Ring1/Ring1A, and BMI-1/Bmi-1, in addition to hPH2 and PC3 (present in some batches of purification). Analysis of the three ring domain-containing proteins indicated that Ring2/Ring1B is the catalytic subunit. To dissect the function of individual subunits and to obtain large amounts of purified enzyme complex for detailed functional analysis, an attempt was made to reconstitute the enzymatic activity using recombinant proteins encoded by mouse cDNAs. To this end, Sf9 cells were co-infected with baculoviruses expressing FLAG®-Bmi-1, Ring1A, Ring1B, and Pc3. FLAG®-Bmi-1 and associated proteins were purified by affinity chromatography followed by gel filtration to separate the four-component complex from free FLAG®-Bmi-1 and partial complex (FIG. 6A). Silver staining and ubiquitin E3 ligase assays of the gel filtration column fractions indicate that the four-component complex co-purified with the enzymatic activity as a protein complex of about 250 kDa (FIG. 6B). It should be noted that under these purification conditions, Ph2 appears to be easily dissociated from the four-component complex in a gel-filtration column when it is co-expressed with other components (data not shown). Therefore, a stable five-component protein complex was not formed under these purification conditions.

To determine whether other components of the complex contribute to the enzymatic activity of Ring1B, FLAG®-Ring1B was purified from infected Sf9 cells and its E3 ligase activity compared with GST-Ring1B expressed in $E.\ coli$ and the four-component complex described above. Results shown in FIG. 9 indicate that FLAG®-Ring1B is an active ubiquitin E3 ligase for H2A (compare lanes 2 and 3) and its activity is comparable with that of GST-Ring1B (compare lanes 1 and 2). Surprisingly, the four-component complex is significantly more active as much less enzyme is required to achieve a similar level of H2A ubiquitylation (compare lanes 2 and 4). It is estimated that an equal molar amount of Ring1B in the complex is about 200-fold more active than Ring1B alone (date not shown). These results indicate that one or more than one of the other three subunits in the complex can stimulate the E3 ligase activity of Ring1B.

EXAMPLE 10

Physical Relationship among Components of the PRC1 Complex

Of the five components present in the PRC1 complex, Ring1B is the only subunit demonstrated to have E3 ligase activity by itself (Example 4). To address the effect of other subunits on Ring1B enzymatic activity, an attempt was made to reconstitute Ring1B-containing subcomplexes. Toward this end, the precise spatial relationship among components of the complex were first defined using GST full-down assays. Individual components were expressed as GST fusion proteins and equal amounts of the fusion proteins, as well as GST alone (FIG. 5A, last panel), were immobilized onto beads and incubated with $^{35}$S-labeled proteins. After washing and electrophoresis, the pair-wise protein-protein interactions were revealed by fluorography. Results shown in FIG. 5A indicate that Ring1B can interact with Bmi-1, Pc3, and Ph2 (second panel). Similar interaction patterns were also observed for Ring1A (first panel), consistent with the high similarity of the two proteins. Interestingly, Bmi-1 appears to be capable of interacting with each of the components (fourth panel) indicating that Bmi-1 could be an essential component for maintaining the complex integrity. Both Pc3 and Ph2 appear to be capable of interacting with all the three ring domain-containing proteins, but they do not seem to interact with each other (panels 3 and 5). This pair-wise interaction data is best summarized in FIG. 5B which shows Ring1B making multiple contacts with other components and occupying a central position in this complex.

EXAMPLE 11

Ring1B Associated Proteins Stimulate its E3 Ligase Activity

Figure 7B:
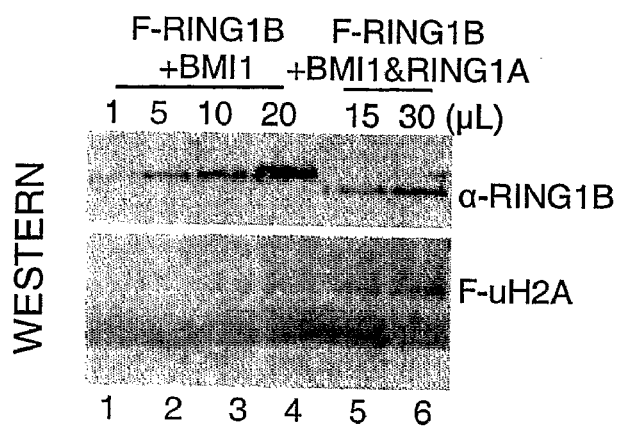
FIG. 7B, Ring1A can also stimulate the ubiquitin ligase activity in vitro. The 2-component complex of F-Ring1B/Bmi1 (lane 1-4) has been compared to 3-component complex of Ring1B/F-Bmi1/Ring1A (lane 5-6). The amount of Ring1B has been verified by western blot using anti-Ring1B antibody (top panel). The ubiquitinated H2A was detected by western blot with anti-Flag antibody (bottom panel).
Figures 9, 10A:
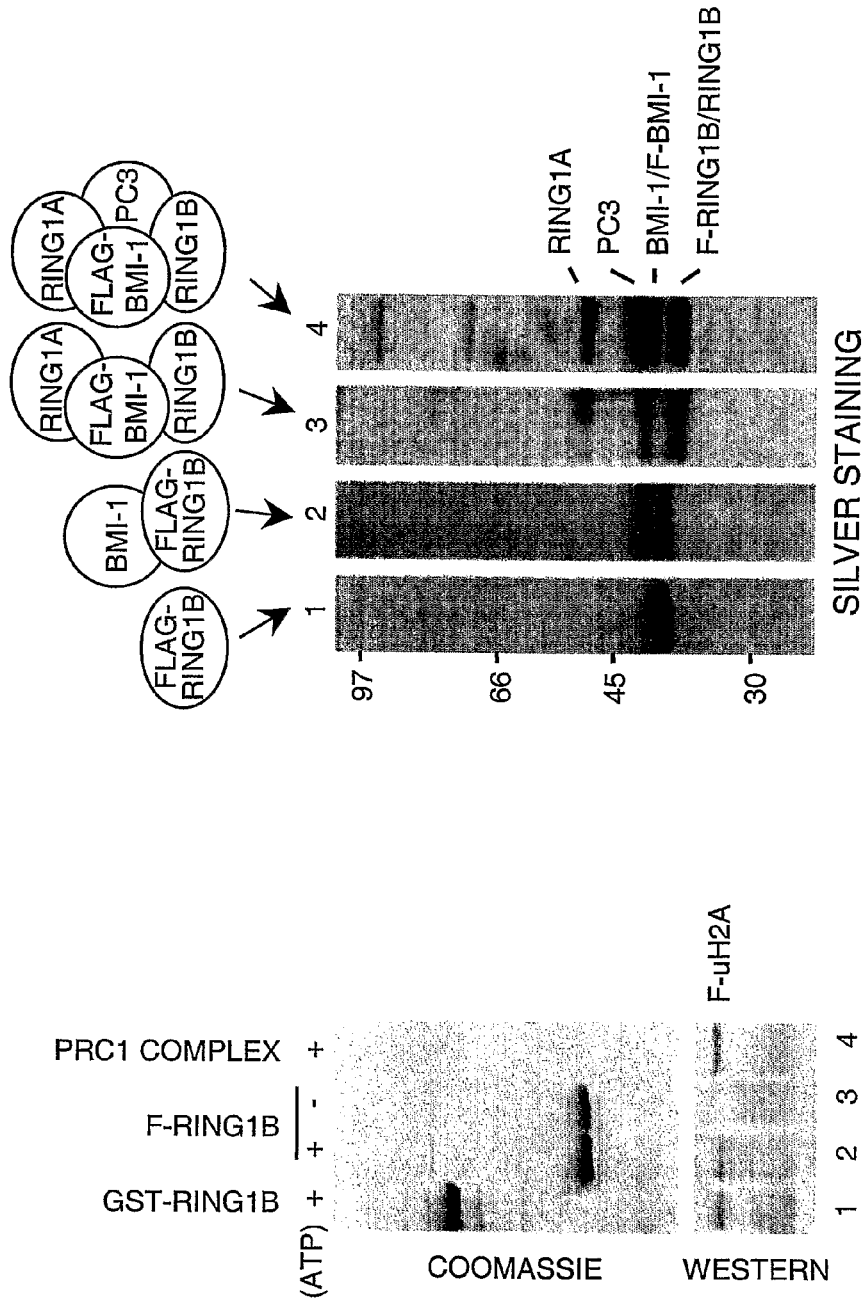
FIG. 9 demonstrates that the reconstituted PRC1 complex is significantly more active than Ring1B alone. Comparison of the E3 ligase activity (bottom panel) of the recombinant Ring1B made in *E. coli* (lane 1), and in Sf9 cells (lanes 2, 3) either alone or in the context of the 4-component complex (lane 4). The amount of enzymes required for equal activity is dramatically different as revealed by COOMASSIE staining (top panel).
FIGS. 10A-10B demonstrate that Bmi-1 and Ring1A stimulate the E3 ligase activity of Ring1B in vitro and in vivo.
Figure 10B:
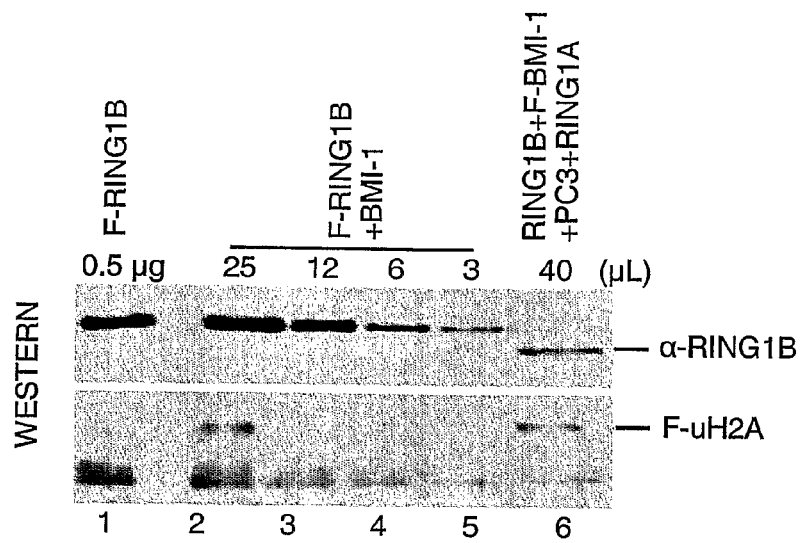

After defining the spatial relationship among the five components, a similar two-step purification procedure was used to reconstitute Ring1B-containing subcomplexes with 2 (FLAG®-Ring1B and Bmi-1), 3 (Ring1B, FLAG®-Bmi-1, and Ring1A), and 4 (Ring1B, FLAG®-Bmi-1, Ring1A, and Pc3) subunits. Silver staining revealed that these reconstituted sub-complexes are near homogeneity (FIG. 10A). To evaluate the relative activities of these purified complexes, various amounts of the different subcomplexes, as indicated by western blot analysis of Ring1B (FIG. 10B, top panel), were used to ubiquitylate equal amounts of nucleosomal substrates. Results shown in FIG. 10B (bottom panel) indicate that association of Bmi-1 with Ring1B stimulated its E3 ligase activity (compare lanes 1 and 2). However, the enzymatic activity of the two-component complex is apparently not comparable to that of the four-component complex (FIG. 10B, compare lanes 4 and 6). Incorporation of Ring1A into the two-component subcomplex (F-Ring1B+Bmi-1) also stimulated the ubiquitin ligase activity (FIG. 7B, compare lanes 3 and 6). These data indicate that Bmi-1, Ring1A, and Pc3 all contribute to optimal activity of Ring1B in vitro.

To substantiate the above observations in vivo, the availability of the Bmi-1 and Ring1A null mouse embryonic fibroblast (MEF) cells was used to advantage and the effects of knockout of these two genes on the level of H2A ubiquitylation was analyzed. Equal amounts of histone extracts prepared from wild-type and Bmi-1 or Ring1A knockout MEFs were subjected to western blot analysis using antibodies specific for ubiquitinated H2A. Results shown in FIGS. 8A and 8B indicate that knockout of either of the two genes greatly reduced the H2A ubiquitylation level. Together, these data indicate that Bmi-1 and Ring1A contribute to H2A ubiquitylation in vivo.

EXAMPLE 12

Knockout of Ring1A and Bmi-1 Results in Alterations in Hox Gene Expression

Figure 11A:
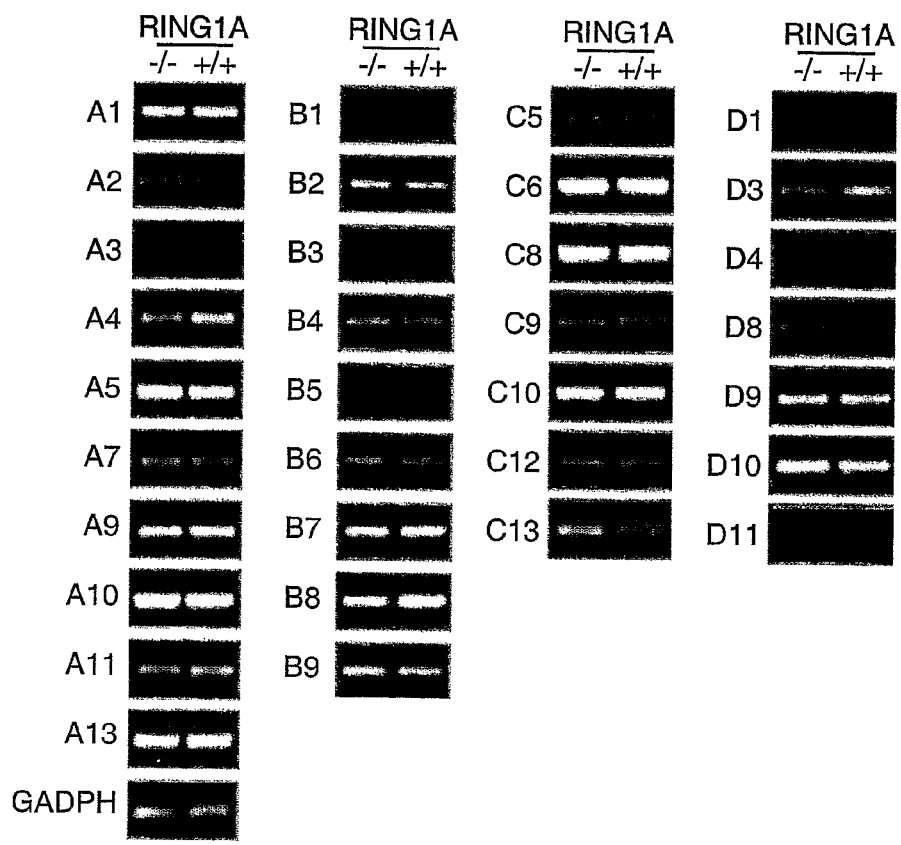
FIGS. 11A-11B show the effects of Ring1A and Bmi-1 knockout on Hox gene expression. Hox gene expression was analyzed by RT-PCR using total RNA isolated from Ring1A null (FIG. 11A), or Bmi-1 null (FIG. 11B) MEFs and compared with that isolated from wild-type MEFs. GAPDH was a control for equal RNA input in RT-PCR. In the absence of reverse transcriptase (RT), no PCR product was detected in any of the reactions (data not shown) showing that the signals observed were not from amplification of genomic DNA. Up-regulated genes in Bmi-1 null cells are underlined, down-regulated genes in Bmi-1 null cells are indicated by *.
Figure 11B:
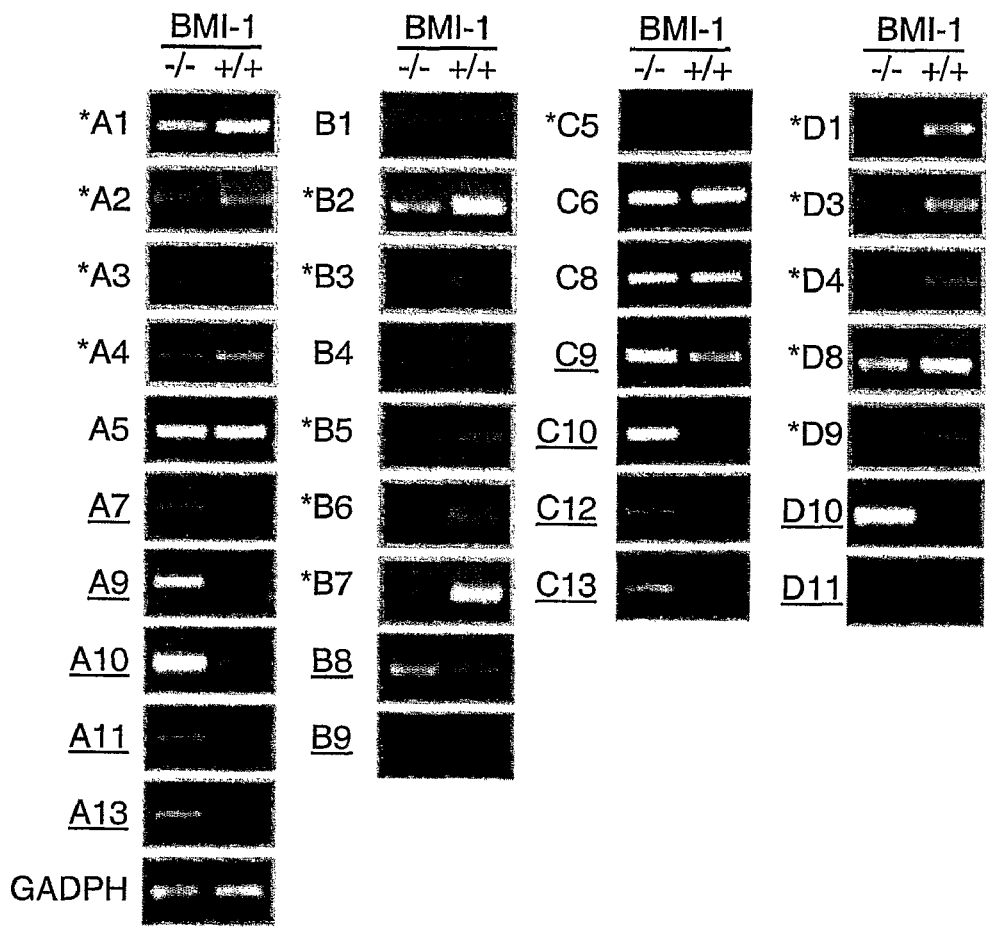

Having demonstrated that knockout of Ring1A and Bmi-1 results in a significant decrease in the H2A ubiquitylation level, their role in Hox gene expression was investigated. Previous studies in mice indicate that loss of Ring1A and Bmi-1 function resulted in anterior and posterior transformations, respectively (del Mar Lorente et al. (2000) *Development* 127:5093-5100; van der Lugt et al. (1996) *Genes Dev.* 8:757-769). Analysis of the expression patterns of selected Hox genes by RNA in situ hybridization revealed a shift in their expression boundaries. The shift is subtle in Ring1A$^{-/-}$ mice while the shift is more significant in Bmi-1$^{-/-}$ mice (del Mar Lorente et al. (2000) *Development* 127:5093-5100; van der Lugt et al. (1996) *Genes Dev* 8:757-769). These studies, however, did not analyze changes in levels of Hox gene expression. To analyze the potential effects of Ring1A and Bmi-1 knockout on Hox gene expression levels, expression of 33 out of the 39 Hox genes was analyzed by RT-PCR using RNAs isolated from MEFs of wild-type and mutant littermates as templates. It is not clear whether failure of amplifying the other six Hox genes is due to a low expression level of these Hox genes or to primer problems. Results shown in FIG. 11A indicate that Ring1A knockout only modestly affected HoxC13, HoxD3, and HoxD10 expression. In contrast to the subtle changes in the Ring1A knockout, knockout of Bmi-1 resulted in significant changes in the expression of most of the Hox genes (FIG. 11B). Of the 33 Hox genes analyzed, 12 (underlined) are significantly upregulated, and 13 (indicated by a *) are significantly down-regulated. It is interesting to note that most late Hox genes are up-regulated while most early Hox genes are down-regulated. Given that the PcG proteins are believed to be involved in gene silencing, down regulation in response to loss of Bmi-1 function might not represent a direct effect. Therefore, further analysis has focused on up-regulated genes, particularly HoxC13 because up-regulation of this gene was observed in MEFs of both Bmi-1 and Ring1A knockouts.

EXAMPLE 13

Derepression of HoxC13 Correlates with Decreased H2A Ubiquitylation at Promoter

Figures 12A, 12B:
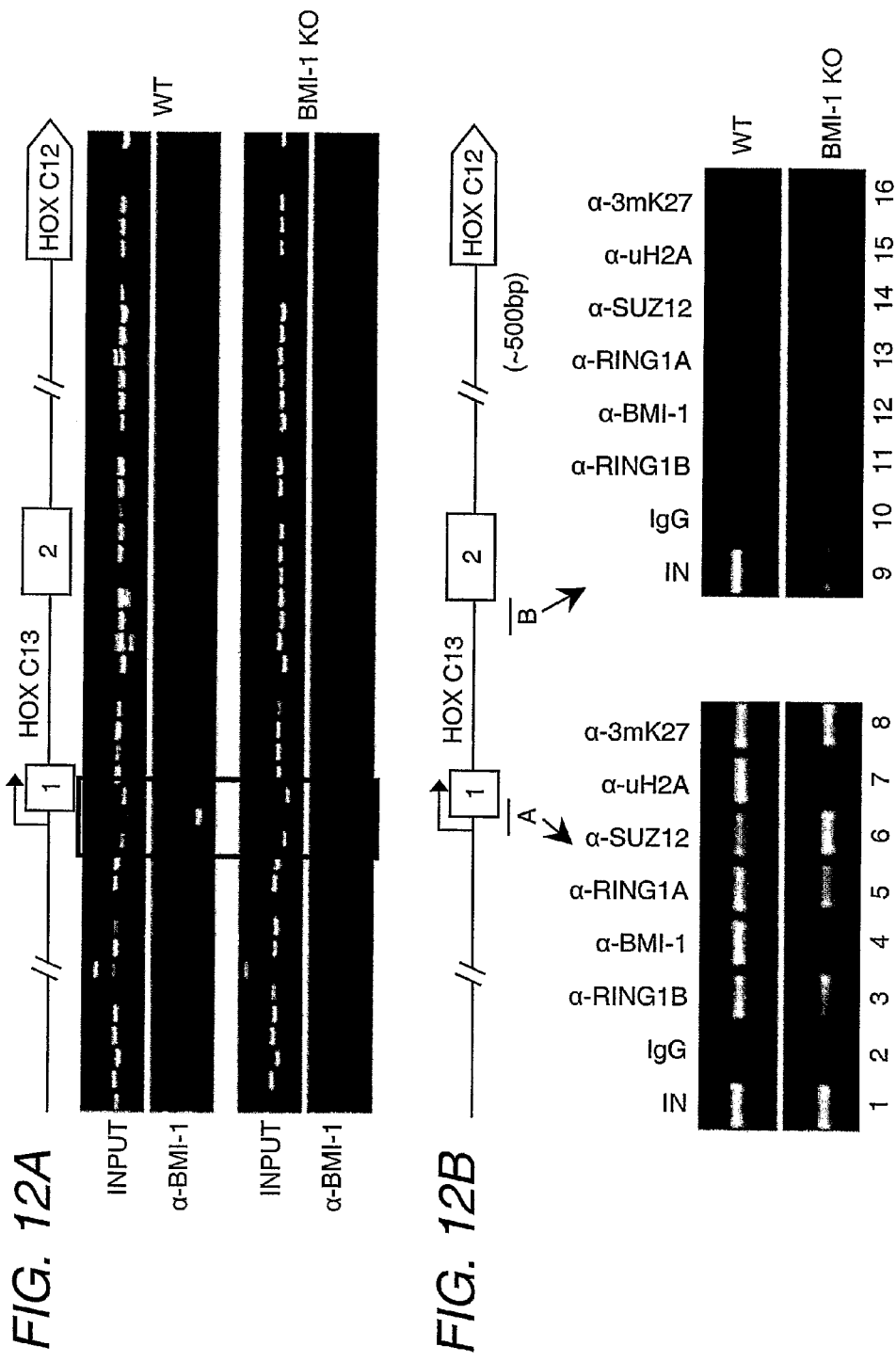
FIGS. 12A-12B show derepression of HoxC13 in Bmi-1 knockout MEFs correlates with a decreased level of promoter H2A ubiquitylation.

To understand the relationship between Bmi-1, H2A ubiquitylation, and HoxC13 derepression, Bmi-1 binding across the entire HoxC13 gene locus was first evaluated by chromatin immunoprecipitation (ChIP) assays. Results shown in FIG. 12A indicate that Bmi-1 is highly enriched in a 500 bp region that encompasses the transcription start site. The observed binding is specific as a similar signal is not observed in a parallel ChIP experiment using the Bmi-1$^{-/-}$ cells. Since Bmi-1 is part of the PRC1 H2A ubiquitin E3 ligase complex, and PRC1 functions together with the EZH2 H3-K27 methyltransferase complex in Hox gene silencing (Ringrose and Paro (2004) *Annu Rev Genet* 38:413-443), the presence in this region of other PcG proteins belonging to the two protein complexes as well as H3-K27 methylation and H2A ubiquitylation was analyzed. It was found that all the components of the two complexes analyzed are present (FIG. 12B, region A). Consistent with the two protein complexes respectively mediating H3-K27 methylation and H2A ubiquitylation, both histone modifications are observed in the region. Protein binding and histone modifications are restricted to the promoter region as a parallel analysis of a region in the intron between exon1 and exon2 did not detect their presence (region B). Consistent with an important role for Bmi-1 in H2A ubiquitylation, knockout of Bmi-1 resulted in significant decrease of H2A ubiquitylation in the promoter region (FIG. 12B, lane 7). Interestingly, loss of Bmi-1 binding or H2A ubiquitylation does not affect the binding of Suz12, a component of the Ezh2 complex, or H3-K27 methylation (lanes 6 and 8). This is consistent with the notion that PRC1 recruitment and H2A ubiquitylation are downstream events of Ezh2-mediated H3-K27 methylation. Collectively, the above results support a critical role for Bmi-1 in H2A ubiquitylation and Hox gene silencing.

EXAMPLE 14

Figure 13A:
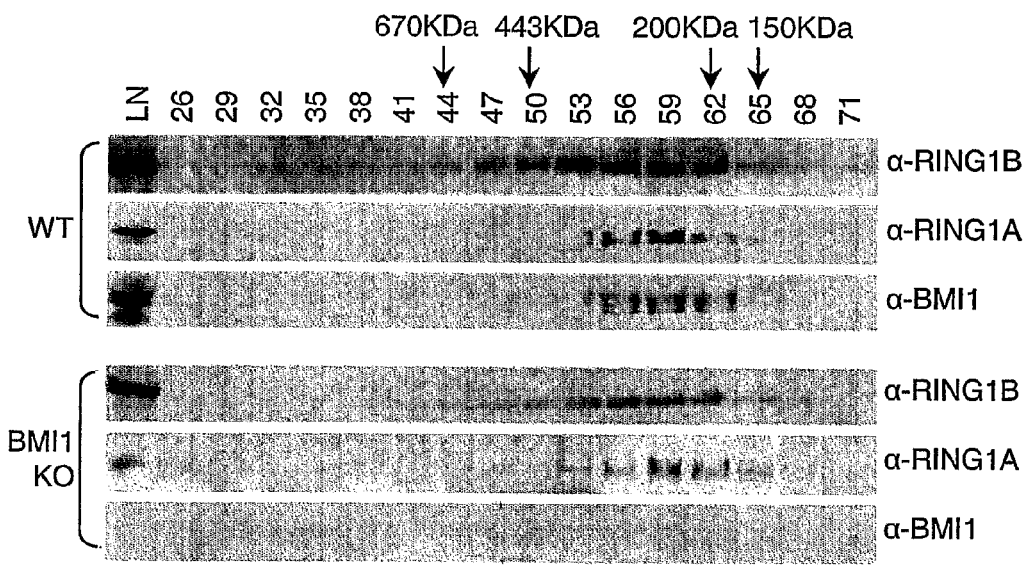
FIGS. 13A-13D demonstrate that replacement of Bmi-1 with Mel-18 maintains the complex integrity, but not its E3 ligase activity.
Figure 13B:
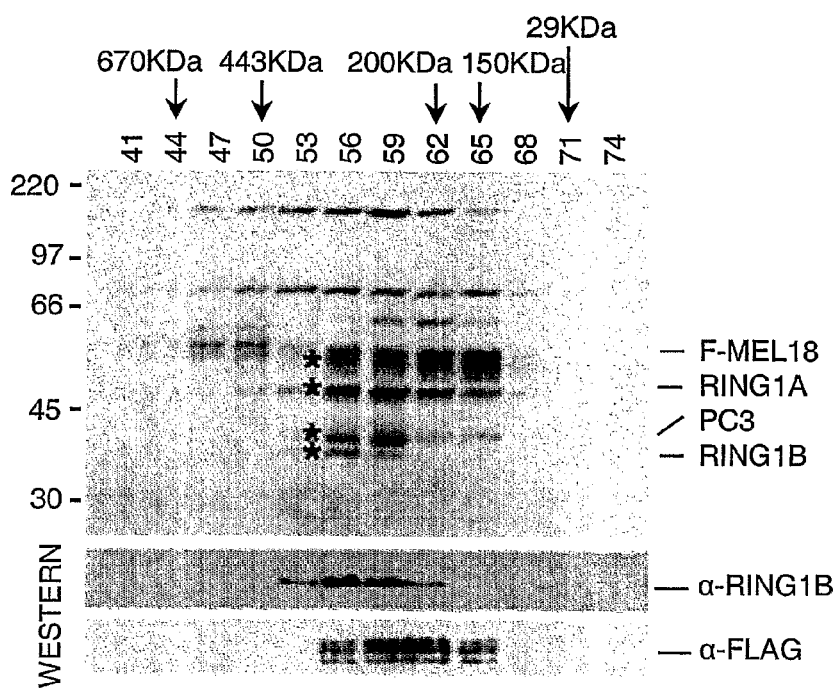

Mel-18 can Substitute for Bmi-1 to Stabilize PRC1, but is not Functionally Redundant It is interesting to note that both Ring1A and Ring1B are present in the promoter region in the absence of Bmi-1 (FIG. 12B, lanes 3 and 5, left panels). This appears to be inconsistent with the finding that Bmi-1 mediates Ring1A and Ring1B interactions (FIG. 5B). To determine whether knockout of Bmi-1 affects the integrity of the PRC1 complex, the elution profile of the PRC1 components over a gel-filtration column using protein extracts derived from wild-type and Bmi-1$^{-/-}$ MEFs were compared. Results shown in FIG. 13A indicate that the Ring1A and Ring1B elution profile is not altered by Bmi-1 knockout indicating that the integrity of the PRC1 complex is not affected by loss of Bmi-1. One possible explanation is that Mel-18, a protein that is 70% identical to Bmi-1, may replace Bmi-1 to maintain complex integrity. To address this possibility directly, Sf9 cells were co-infected with baculoviruses that express Ring1A, Ring1B, Pc3, and Flag-Mel-18. After affinity purification using FLAG®-antibody coated beads, the bound proteins were eluted and separated on a gel-filtration column. Results shown in FIG. 13B indicate that Mel-18 co-purified with the other components as a protein complex.

Figure 13C:
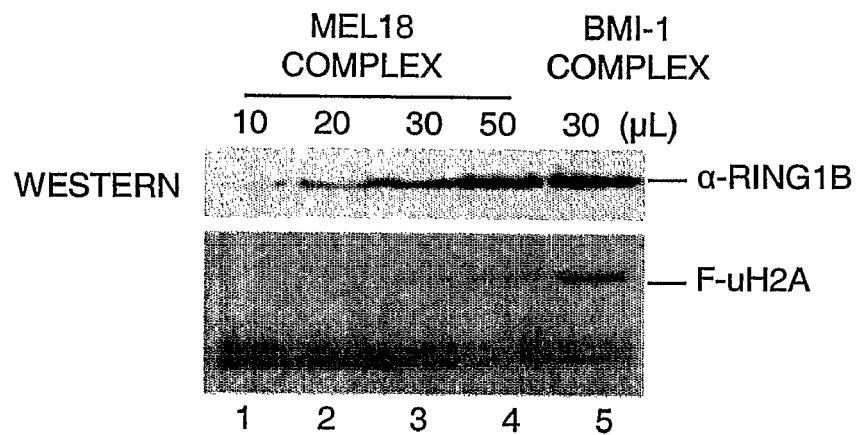
Figure 13D:
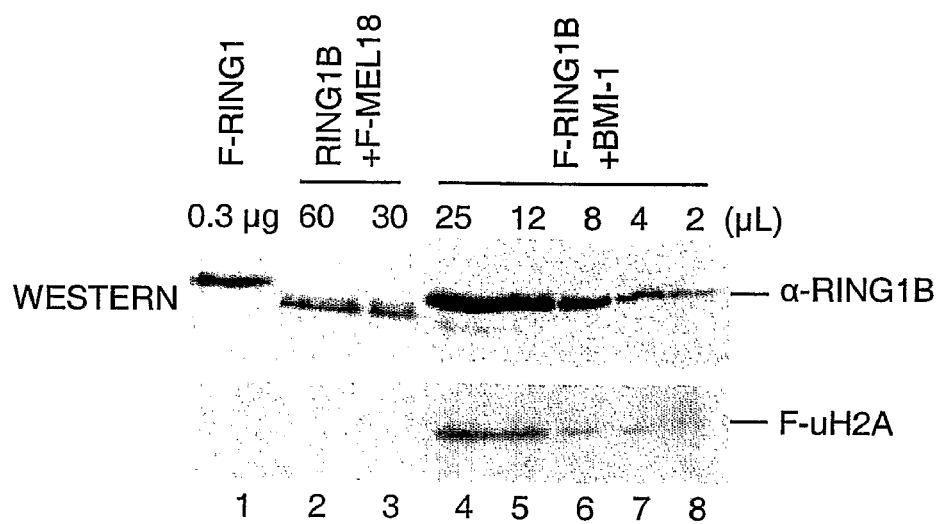

Having demonstrated that Mel-18 can replace Bmi-1 in forming the PRC1 complex, the question arose whether the Mel-18-containing complex is functionally similar to the Bmi-1-containing complex with regard to H2A ubiquitylation. After quantifying the two protein complexes through western analysis of the Ring1B component, their E3 ligase activities were directly compared. Results shown in FIG. 13C indicate that the Bmi-1 containing complex is significantly more active than the Mel-18 containing complex (compare lanes 4 and 5). To further evaluate the capability of Bmi-1 and Mel-18 to stimulate Ring1B E3 ligase activity, Ring1B alone, and Ring1B in complex with Bmi-1 or Mel-18 from infected insect cells were purified and their E3 ligase activity directly compared. Results shown in FIG. 13D demonstrate that Bmi-1 greatly stimulated the Ring1B E3 ligase activity, while Mel-18 does not have a detectable effect (compare lanes 2 and 6). These results collectively support that Mel-18 can be incorporated into the PRC1 complex like Bmi-1, but it has little effect on the E3 ligase activity of Ring1B. These results further support a non-redundant function for Bmi-1 and Mel-18 and are consistent with the fact that Bmi-1 and Mel-18 knockout mice exhibited different phenotypes (Akasaka et al. (1996) *Development* 122:1513-1522; van der Lugt et al. (1994) *Genes Dev* 8:757-769).

EXAMPLE 15

Figure 14A:
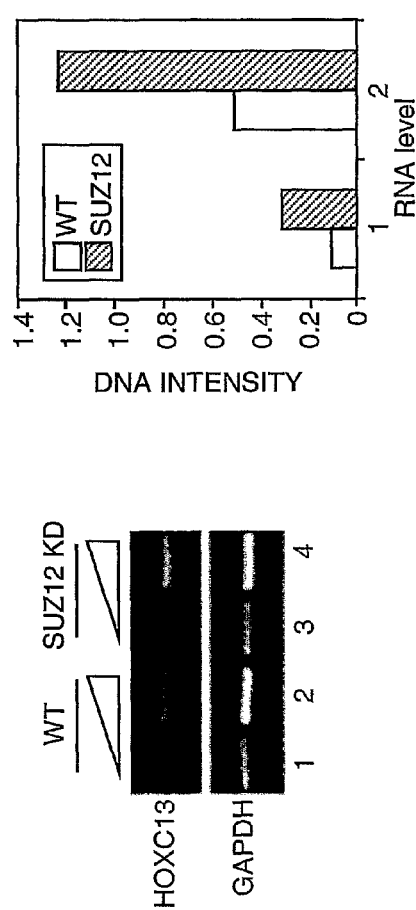
FIGS. 14A-14B show that SUZ12 knock-down affects PRC1 recruitment and H2A ubiquitylation concomitant with HoxC13 derepression.
Figure 14B:
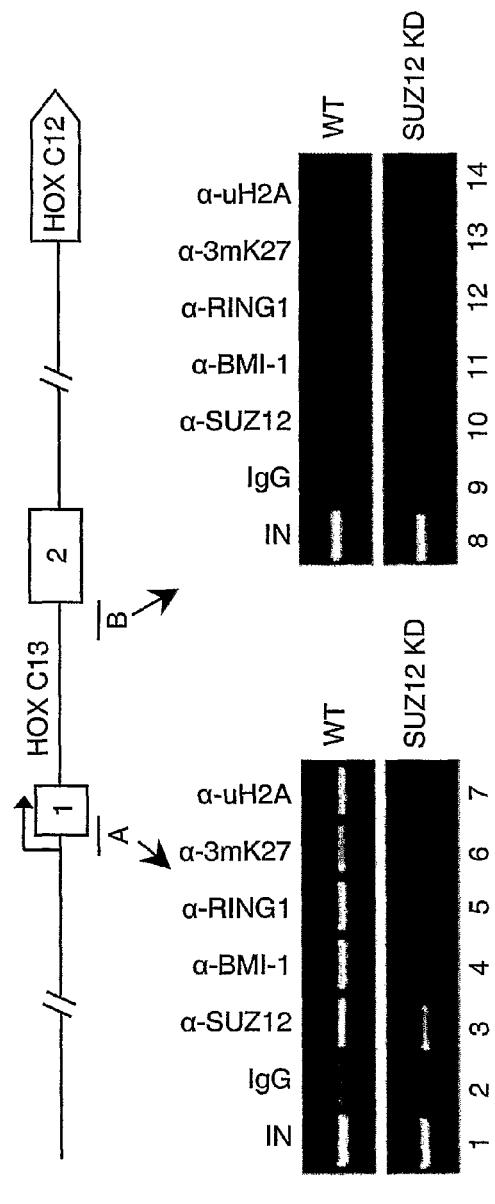

SUZ12 Knockdown Affects Chromatin Binding by the PRC1 and H2A Ubiquitylation Studies in *Drosophila* have suggested a hierarchical PcG protein recruitment pathway in Ubx gene silencing (Wang et al., (2004) *Mol. Cell* 14:637-646). Data presented in FIG. 12 is consistent with the notion that EZH2-mediated H3-K27 methylation precedes H2A ubiquitylation. To analyze the relationship between H3-K27 methylation and H2A-K119 ubiquitylation further, it was determined whether impaired H3-K27 methylation affects PRC1 recruitment and H2A ubiquitylation. It was previously demonstrated that SUZ12 knockdown resulted in reduced H3-K27 methylation and HoxA9 upregulation (Cao and Zhang (2004) *Mol Cell* 15:47-67). Analysis of the same SUZ12 knockdown cell line indicated that HOXC13 is also upregulated when compared with the mock knockdown (FIG. 14A). Thus, binding of SUZ12, and two different components of the PRC1 complex, Bmi-1 and Ring1A were analyzed. In addition, H3-K27 methylation and H2A ubiquitylation in the promoter and intron of the corresponding regions analyzed in FIG. 12 were also analyzed. Results shown in FIG. 14B indicated enrichment of SUZ12, BMI-1, RING1 and the corresponding histone modifications in the promoter region (region A), but not in the intron (region B). However, knockdown of SUZ12 not only affected H3-K27 methylation (lane 6), but also affected BMI-1 and RING1 binding and consequently, H2A ubiquitylation (lanes 4, 5, and 7). This data is consistent with the notion that H3-K27 methylation provides a binding site for Pc (Fischle et al. (2003) *Genes Dev* 17:1870-1881; Min et al. (2003) *Genes Dev* 17:1823-1828), and thus contributes to PRC1 recruitment and H2A ubiquitylation. Collectively, the above results indicate that the sequential PcG protein recruitment model, demonstrated in *Drosophila* (Wang et al. (2004) *Mol. Cell* 14:637-646), is also conserved in mammals.

EXAMPLE 16

Bmi1 has E3 Ligase Catalytic Activity

The inventors have further discovered that Bmi-1 has E3 ligase activity. E3 ligase activity was observed for recombinant mouse Bmi-1 produced in Sf9 cells, but not *E. coli*, which raised the possibility that a post-translational modification(s) is required for E3 ligase activity. The inventors have now determined by mass spectrometry that recombinant mouse Bmi-1 made in Sf9 cells is methylated on K88 and K92. Consistent with methylation of these residues being important for enzymatic activity, mutation of K88 and K92 abrogated the E3 ligase activity of a recombinant Bmi-1 with mutations at K88 and K92.

The foregoing is illustrative of the present invention, and is not to be construed as limiting thereof. The invention is defined by the following claims, with equivalents of the claims to be included therein.

That which is claimed is:

1. A method of identifying a compound that modulates ubiquitin E3 ligase activity of Ring2, the method comprising:
   contacting Ring2 with a protein substrate in the presence of a test compound; and
   detecting the level of ubiquitination of the protein substrate under conditions sufficient to provide ubiquitination of the protein substrate, wherein a change in ubiquitination of the protein substrate as compared with the level of ubiquitination of the protein substrate in the absence of the test compound indicates that the test compound is a modulator of the ubiquitin E3 ligase activity of Ring2.

2. The method of claim 1, wherein the method is a method of identifying a compound that modulates histone ubiquitin E3 ligase activity of Ring2.

3. The method of claim 2, wherein the method is a method of identifying a compound that modulates histone H2A ubiquitin E3 ligase activity of Ring2.

4. The method of claim 3, wherein the method is a method of identifying a compound that modulates histone H2A-K119 ubiquitin E3 ligase activity of Ring2.

5. The method of claim 2, wherein the histone substrate is a core histone, a mononucleosome, a dinucleosome or an oligonucleosome.

6. The method of claim 1, wherein the Ring2 is a recombinant protein.

7. The method of claim 1, wherein a reduction in ubiquitination of the protein substrate as compared with the level of ubiquitination of the protein substrate in the absence of the test compound indicates that the test compound is an inhibitor of the ubiquitin E3 ligase activity of Ring2.

8. The method of claim 1, wherein an increase in ubiquitination of the protein substrate as compared with the level of ubiquitination of the protein substrate in the absence of the test compound indicates that the test compound is an activator of the ubiquitin E3 ligase activity of Ring2.

9. The method of claim 1, wherein the method is a cell-free method.

10. A method of identifying a compound that modulates ubiquitin E3 ligase activity of a complex comprising Ring2, the method comprising:
    contacting the complex with a protein substrate in the presence of a test compound; and
    detecting the level of ubiquitination of the protein substrate under conditions sufficient to provide ubiquitination of the protein substrate, wherein a change in ubiquitination of the protein substrate as compared with the level of ubiquitination of the protein substrate in the absence of the test compound indicates that the test compound is a modulator of the ubiquitin E3 ligase activity of the complex.

11. The method of claim 10, wherein the complex comprises Ring2, Ring1, Bmi1 and HPH2.

12. The method of claim 10, wherein the complex comprises dRing1, Psc and ph.

13. The method of claim 10, wherein the method is a method of identifying a compound that modulates histone ubiquitin E3 ligase activity of the complex.

14. The method of claim 13, wherein the method is a method of identifying a compound that modulates histone H2A ubiquitin E3 ligase activity of the complex.

15. The method of claim 14, wherein the method comprises detecting the level of H2A-K119 ubiquitination.

16. The method of claim 10, wherein the complex is a recombinant complex.

17. The method of claim 10, wherein a reduction in ubiquitination of the protein substrate as compared with the level of ubiquitination of the protein substrate in the absence of the test compound indicates that the test compound is an inhibitor of the ubiquitin E3 ligase activity of the complex.

18. The method of claim 10, wherein an increase in ubiquitination of the protein substrate as compared with the level of ubiquitination of the protein substrate in the absence of the test compound indicates that the test compound is an activator of the ubiquitin E3 ligase activity of the complex.

19. A method of identifying a candidate compound for treating cancer, the method comprising:
  contacting Ring2 with a histone H2A substrate in the presence of a test compound; and
  detecting the level of ubiquitination of the histone H2A substrate under conditions sufficient to provide histone H2A ubiquitination, wherein a reduction in histone H2A ubiquitination as compared with the level of histone H2A ubiquitination in the absence of the test compound indicates that the test compound is a candidate compound for the treatment of cancer.

* * * * *